US010922774B2

(12) United States Patent
Ryan et al.

(10) Patent No.: US 10,922,774 B2
(45) Date of Patent: Feb. 16, 2021

(54) COMPREHENSIVE MEDICATION ADVISOR

(71) Applicant: CERNER INNOVATION, INC., Kansas City, MO (US)

(72) Inventors: Hugh H. Ryan, Lee's Summit, MO (US); Kelly Michelle Luden, Kansas City, MO (US); Amanda Kathleen Sullins, Lee's Summit, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 976 days.

(21) Appl. No.: 14/586,344

(22) Filed: Dec. 30, 2014

(65) Prior Publication Data

US 2015/0227717 A1 Aug. 13, 2015

Related U.S. Application Data

(63) Continuation of application No. 14/502,316, filed on Sep. 30, 2014, now abandoned.
(Continued)

(51) Int. Cl.
*G06Q 50/22* (2018.01)
*G06F 16/28* (2019.01)
(Continued)

(52) U.S. Cl.
CPC ........... *G06Q 50/22* (2013.01); *G06F 16/285* (2019.01); *G06Q 50/24* (2013.01); *G16H 50/70* (2018.01);
(Continued)

(58) Field of Classification Search
None
See application file for complete search history.

(56) References Cited

U.S. PATENT DOCUMENTS

| | | | |
|---|---|---|---|
| 6,587,829 B1 | 7/2003 | Camarda et al. |
| 2002/0123906 A1 | 9/2002 | Goetzke et al. |

(Continued)

OTHER PUBLICATIONS

Evans & Pestotnik, Applications of Medical Informatics in Antibiotic Therapy, Antimicrobial Susceptibility Testing, Edited by J.A. Poupard et al., Plenum Press, New York, 1994, pp. 87-96 (Year: 1994).*

(Continued)

*Primary Examiner* — Rachelle L Reichert
(74) *Attorney, Agent, or Firm* — Shook, Hardy & Bacon L.L.P.

(57) ABSTRACT

Methods, systems, computer storage media, and graphical user interfaces for population health management are disclosed. The population health management system may allow for cross-continuum tracking and subsequent interactions with transactional systems, providers, and/or patients. The population health management system may include utilizing clinically relevant algorithms to populate registries to enable healthcare providers to better facilitate care for a population of patients. The population health management system may consolidate and provide comprehensive condition-specific and/or patient situation specific information that is accessible and updatable across venues. The population health management system may create cross venue antibiograms based on medications information and susceptibility results which can be filtered for selected demographics. The population health management system may be utilized to provide multiple medication options including dosing, generic alternatives, cost, availability, and susceptibility information. Inappropriate trends may be flagged and monitored and medication stewards may be alerted or notified to intervene.

20 Claims, 39 Drawing Sheets

Related U.S. Application Data

(60) Provisional application No. 61/888,313, filed on Oct. 8, 2013, provisional application No. 61/885,359, filed on Oct. 1, 2013.

(51) Int. Cl.

| | |
|---|---|
| ***G16H 50/70*** | (2018.01) |
| ***G06Q 50/24*** | (2012.01) |
| ***G16H 10/60*** | (2018.01) |
| ***G06F 19/00*** | (2018.01) |
| *G06Q 30/02* | (2012.01) |

(52) U.S. Cl.
CPC ......... *G06F 19/3456* (2013.01); *G16H 10/60* (2018.01)

(56) References Cited

U.S. PATENT DOCUMENTS

| | | | | |
|---|---|---|---|---|
| 2003/0055531 | A1* | 3/2003 | Liff | G06F 19/3462 700/235 |
| 2003/0204419 | A1 | 10/2003 | Wilkes et al. | |
| 2004/0059607 | A1 | 3/2004 | Ball et al. | |
| 2004/0260666 | A1* | 12/2004 | Pestotnik | G06F 19/3481 706/46 |
| 2005/0209880 | A1 | 9/2005 | Drelicharz et al. | |
| 2006/0288095 | A1 | 12/2006 | Torok et al. | |
| 2007/0055545 | A1 | 3/2007 | Maughan et al. | |
| 2007/0106536 | A1 | 5/2007 | Moore | |
| 2007/0299694 | A1 | 12/2007 | Merck | |
| 2008/0046292 | A1* | 2/2008 | Myers | G06Q 50/24 705/3 |
| 2008/0208618 | A1 | 8/2008 | Schoenberg et al. | |
| 2008/0208631 | A1 | 8/2008 | Morita et al. | |
| 2008/0221923 | A1 | 9/2008 | Shogan | |
| 2009/0054735 | A1 | 2/2009 | Higgins et al. | |
| 2009/0132280 | A1 | 5/2009 | Morita et al. | |
| 2009/0210252 | A1* | 8/2009 | Silver | G06Q 10/10 705/3 |
| 2010/0094658 | A1 | 4/2010 | Mok et al. | |
| 2010/0131293 | A1 | 5/2010 | Linthicum et al. | |
| 2010/0131482 | A1 | 5/2010 | Linthicum et al. | |
| 2010/0312581 | A1 | 12/2010 | Wachtell et al. | |
| 2011/0077973 | A1 | 3/2011 | Breitenstein et al. | |
| 2011/0295616 | A1 | 12/2011 | Vesto | |
| 2011/0301977 | A1 | 12/2011 | Belcher et al. | |
| 2011/0301982 | A1 | 12/2011 | Green, Jr. et al. | |
| 2012/0065987 | A1 | 3/2012 | Farooq et al. | |
| 2012/0129139 | A1 | 5/2012 | Partovi | |
| 2012/0203573 | A1 | 8/2012 | Mayer et al. | |
| 2012/0304054 | A1 | 11/2012 | Orf et al. | |
| 2012/0323595 | A1 | 12/2012 | Hawkins et al. | |
| 2013/0035946 | A1 | 2/2013 | Ratan et al. | |
| 2013/0217063 | A1 | 8/2013 | Metzger et al. | |
| 2013/0226608 | A1 | 8/2013 | Di Lascia et al. | |
| 2013/0290005 | A1 | 10/2013 | Vesto et al. | |
| 2013/0325502 | A1* | 12/2013 | Robicsek | G06Q 10/04 705/3 |
| 2013/0325505 | A1 | 12/2013 | Vengco | |
| 2014/0058754 | A1 | 2/2014 | Wild | |
| 2015/0058030 | A1 | 2/2015 | Scantland et al. | |
| 2015/0381414 | A1 | 12/2015 | Xu et al. | |

OTHER PUBLICATIONS

First Action Interview Preinterview Communication dated Jun. 15, 2016 in U.S. Appl. No. 14/502,286, 4 pages.
First Action Interview Preinterview Communication dated Jun. 16, 2016 in U.S. Appl. No. 14/502,226, 5 pages.
First Action Interview Preinterview Communication dated Jun. 29, 2016 in U.S. Appl. No. 14/502,349, 6 pages.
First Action Interview Preinterview Communication dated Jul. 14, 2016 in U.S. Appl. No. 14/502,316, 6 pages.
Ross, David B., "An antibiogram data model and implementation schema" (2012). Scholar Archive. Paper 783. (Obtained from http://digitalcommons.ohsu.edu/etd). 79 pages.
First Action Interview Office Action dated Oct. 17, 2016 in U.S. Appl. No. 14/502,349, 9 pages.
First Action Interview Office Action dated Oct. 17, 2016 in U.S. Appl. No. 14/502,336, 9 pages.
First Action Interview Office Action dated Oct. 17, 2016 in U.S. Appl. No. 14/502,316, 9 pages.
First Action Interview Office Action dated Oct. 17, 2016 in U.S. Appl. No. 14/502,286, 9 pages.
Final Office Action dated Mar. 22, 2017 in U.S. Appl. No. 14/502,336, 37 pages.
Final Office Action dated Apr. 5, 2017 in U.S. Appl. No. 14/502,286, 28 pages.
Final Office Action dated Apr. 10, 2017 in U.S. Appl. No. 14/502,336, 37 pages.
First Action Interview Pilot Program Pre-Interview Communication dated Feb. 14, 2018 in U.S. Appl. No. 14/586,295, 29 pages.
First Action Interview Office Action dated Mar. 5, 2018 in U.S. Appl. No. 14/583,308, 5 pages.
First Action Interview Pre-Interview Communication dated Oct. 26, 2017 in U.S. Appl. No. 14/586,338, 5 pages.
Non-Final Office Action dated Nov. 17, 2017 in U.S. Appl. No. 14/502,286, 26 pages.
Non-Final Office Action dated Nov. 17, 2017 in U.S. Appl. No. 14/502,336, 39 pages.
Non-Final Office Action dated Dec. 1, 2017 in U.S. Appl. No. 14/502,316, 39 pages.
First Action Interview Office Action dated Dec. 6, 2017 in U.S. Appl. No. 14/586,329, 6 pages.
First Action Interview Office Action dated Dec. 14, 2017 in U.S. Appl. No. 14/586,340, 7 pages.
Preinterview First Office Action dated Dec. 15 ,2017 in U.S. Appl. No. 14/586,308, 5 pages.
First Action Interview Office Action dated Dec. 21, 2017 in U.S. Appl. No. 14/586,338, 6 pages.
Non-Final Office Action dated Dec. 26, 2017 in U.S. Appl. No. 14/502,349, 30 pages.
Final Office Action dated Jun. 28, 2017 in U.S. Appl. No. 14/502,349, 32 pages.
First Action Interview Pre-Interview Communication dated Sep. 14, 2017 in U.S. Appl. No. 14/586,329, 5 pages.
First Action Interview Pre-Interview Communication dated Sep. 21, 2017 in U.S. Appl. No. 14/586,340, 5 pages.
Final Office Action received for U.S. Appl. No. 14/502,286, dated Aug. 10, 2018, 23 Pages.
Final Office Action received for U.S. Appl. No. 14/586,329, dated Aug. 10, 2018, 24 Pages.
Final Office Action received for U.S. Appl. No. 14/586,338, dated Aug. 14, 2018, 27 Pages.
Final Office Action received for U.S. Appl. No. 14/586,340, dated Jul. 27, 2018, 26 Pages.
Non Final Office Action received for U.S. Appl. No. 14/502,286, dated Apr. 5, 2019, 18 pages.
Non-Final Office Action received for U.S. Appl. No. 14/586,329, dated Mar. 8, 2019, 20 pages.
Non-Final Office Action received for U.S. Appl. No. 14/586,338, dated Mar. 22, 2019, 27 pages.
Non-Final Office Action received for U.S. Appl. No. 14/586,340, dated Jan. 9, 2020, 10 pages.
Final Office Action received for U.S. Appl. No. 14/502,336, dated Oct. 1, 2019, 19 pages.
Final Office Action received for U.S. Appl. No. 14/1586,340, dated Aug. 22, 2019, 25 pages.
Non-Final Office Action received for U.S. Appl. No. 14/586,329, dated Sep. 5, 2019, 21 pages.

* cited by examiner

1700

| | Home | Worklist | Outreach | Population | Connections | | Analytics | 🔍 Cindy Miller ▾ | 1710

Worklist Alert 1720  /—1748

Sort by: Worklist
New Persons

Smith, Janet
45yrs F DOB: 4/10/1968

Reineke, Myra
65yrs F DOB: 8/28/1948

Willings, Jack
72yrs M DOB: 10/15/1941

Montenez, Manuel
47yrs M DOB: 1/23/1966

▾ Smith, Janet    45yrs   Female   DOB: 4/10/1968    Quality Score: [57]   Risk Score: [1.2]

Phone: 808-555-5555                                  Payer Member ID: Payer 123456789, Payer 987654321
Address: 1234 Main St
         Springfield, MO 64531                       MRN: Source 937702761       ~1738

| Overview | CM Tracking | Documentation | Registries | Provider Relationships | Clinical Information |

Vitals and Measurements ~1732

| Weight: | Height: | BMI: | Temperature: | Heart Rate: |
| 83 kg | 166 cm | 30.0 | 99.3 °F | 82 bpm |
| Oct 1, 2013 | Oct 1, 2013 | Oct 1, 2013 | Oct 1, 2013 | Oct 1, 2013 |

Respiratory Rate: | Blood Pressure:
18                | 140/84
Oct 1, 2013       | Oct 1, 2013

▾ Home Device Use

Blood Pressure Cuff    Status: Connected     Weight Scale

1730

Alerts   ~1740

Newly Added: Diabetes Registry
Date: 10/16/2013

Mammogram due Nov 30, 2013

Longitudinal Record  ~1742

▾ Conditions
  Diabetes  ~1744
  Heart Failure
  Hypertension

▾ Medications
  Lipitor           10 mg Daily
  Start Date: 6/20/2012
  Lisinopril        10 mg Daily
  Start Date: 6/20/2012
  Metoprolol        25 mg Daily
  Start Date: 6/20/2012
  Aspirin           81 mg Daily
  Start Date: 6/20/2012
  Plavix            75 mg Daily
  Start Date: 6/20/2012

▸ Procedures
▸ Allergies
▸ Labs

Appointments ~1734                         [Collapse All]

▾ Appointments
Date         Provider            Time      Appointment reason
Nov 2, 2013  Baseline Imaging    4:15 pm   Mammogram ▾ Previous Encounters
Date         Provider         Activity    Location              Reason
Jul 15, 2013 Dr. Tim Williams Discharge   Baseline Hospital     Dx HF exac...
Jan 21, 2013 Dr. Larry Thomas Encounter   Northland Practice    Blood Pres...

Care Team   ~1746

Dr. Larry Thomas
Primary Care Physician

Dr. Julia Harris
Cardiologist

Cindy Miller
Care Manger

Care Plan ~1736                             [Expand All]

▾ Activity
  Physical Activity 30 min x 5 days/week

▾ Diet
  DASH Diet (2000 calories)
  Reduce sodium intake (<2.4 gm/day)

▾ Appointments
  Recommended follow up with PCP - PENDING -

▸ Education

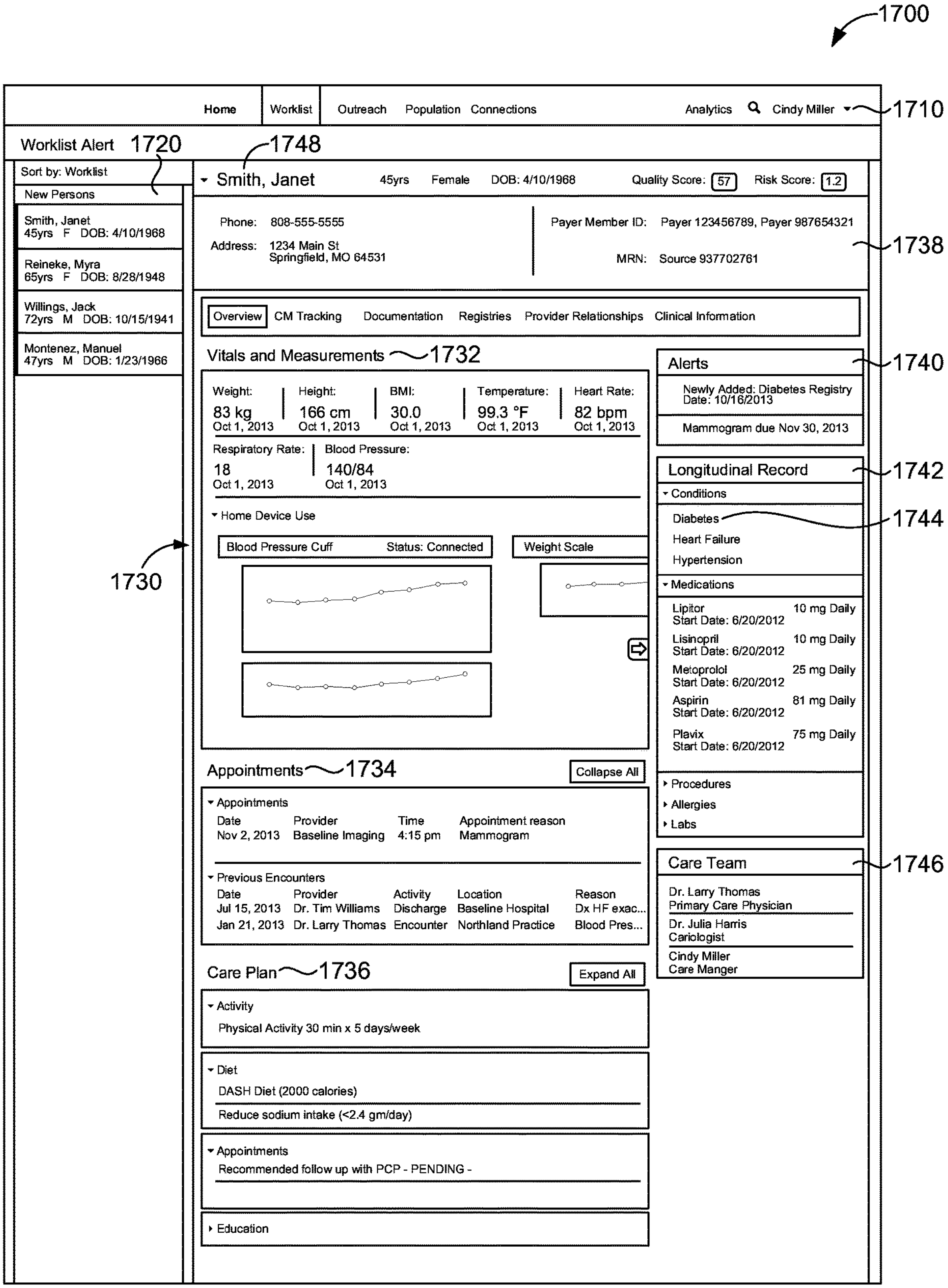

FIG. 17

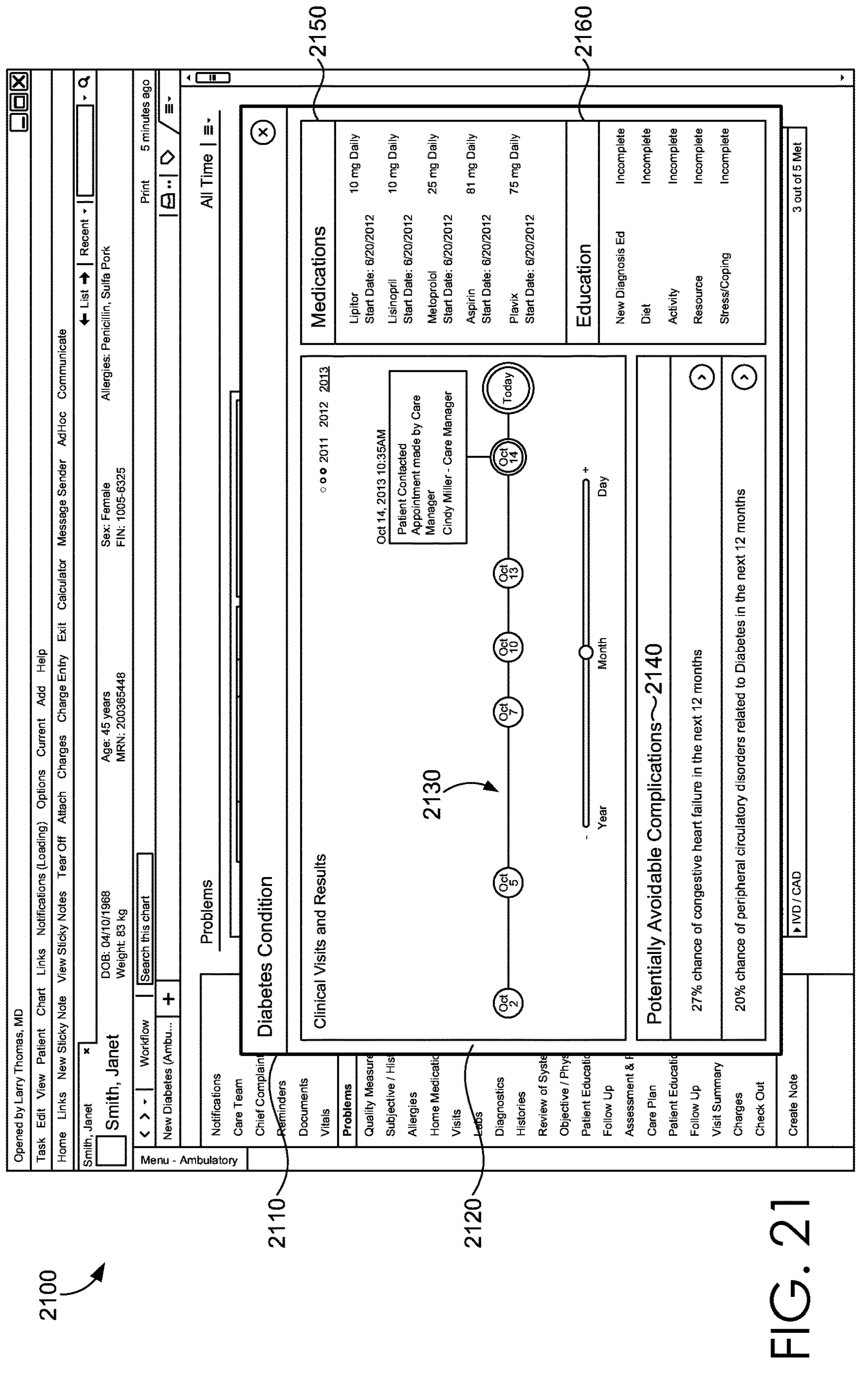

Opened by Larry Thomas, MD
Task  Edit  View  Patient  Chart  Links  Notifications (Loading)  Options  Current  Add  Help
Home  Links  New Sticky Note  View Sticky Notes  Tear Off  Attach  Charges  Charge Entry  Exit  Calculator  Message Sender  AdHoc  Communicate Smith, Janet  x
Smith, Janet   DOB: 04/10/1968   Age: 45 years   Sex: Female   Allergies: Penicillin, Sulfa Pork
Weight: 83 kg   MRN: 200365448   FIN: 1005-6325

← > ▾ | Workflow   Search this chart                                              ← List ↑ | Recent ▾ |
New Diabetes (Ambu... +                                                            Print   5 minutes ago Menu - Ambulatory Notifications
Care Team
Chief Complaint      Diabetes Condition                                    All Time | ≡ ▾
Reminders            ─────────────────                                    ⊗
Documents            Problems
Vitals
Problems         Clinical Visits and Results                          Medications
Quality Measure                                                           Lipitor              10 mg Daily
Subjective / Hist                                                         Start Date: 6/20/2012
Allergies                                         Oct 14, 2013 10:35AM    Lisinopril           10 mg Daily
Home Medicatio                                    Patient Contacted       Start Date: 6/20/2012
Visits                                            Appointment made by Care Metoprolol           25 mg Daily
Labs                                          Manager                 Start Date: 6/20/2012
Diagnostics                                       Cindy Miller - Care Manager Aspirin           81 mg Daily
Histories             ○○● 2011  2012  2013                                Start Date: 6/20/2012
Review of Syste                                                           Plavix               75 mg Daily
Objective / Phys      ⊙   ⊙   ⊙   ⊙   ⊙   ⊙   ⓞ   ⊙                      Start Date: 6/20/2012
Patient Educatio      Oct  Oct  Oct  Oct  Oct  Oct  Oct  Today
Follow Up             2    5    7    10   13   14                         Education
Assessment & F              2130                                          New Diagnosis Ed     Incomplete
Care Plan                                                                 Diet                 Incomplete
Patient Educatio            -───○───────────+                             Activity             Incomplete
Follow Up                  Year    Month    Day                           Resource             Incomplete
Visit Summary                                                             Stress/Coping        Incomplete
Charges              Potentially Avoidable Complications ~2140
Check Out            27% chance of congestive heart failure in the next 12 months
                     20% chance of peripheral circulatory disorders related to Diabetes in the next 12 months   3 out of 5 Met
Create Note          ▶ IVD / CAD 2110
2120
2130
2140
2150
2160

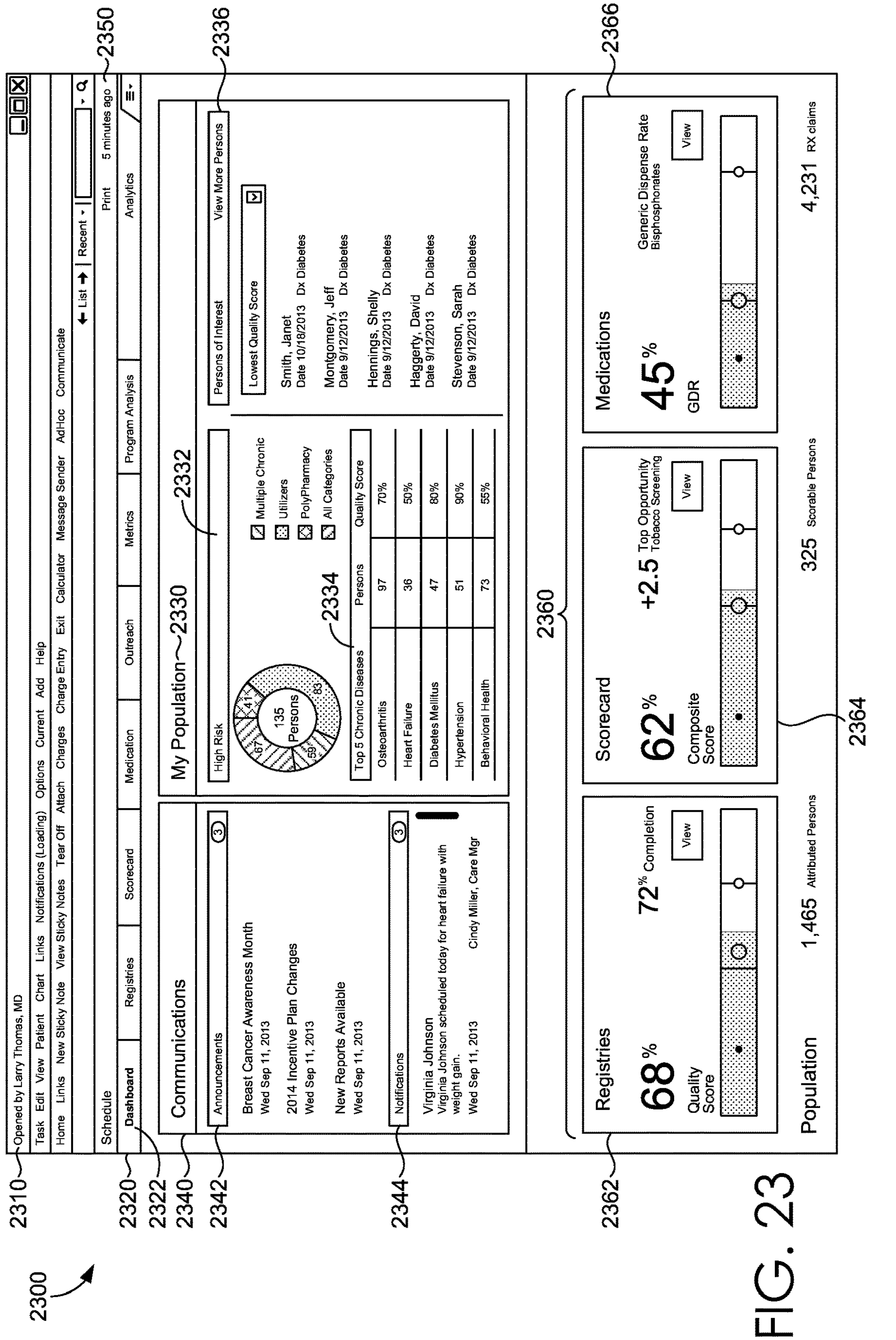

2310 — Opened by Larry Thomas, MD

Task Edit View Patient Chart Links Notifications (Loading) Options Current Add Help
Home Links New Sticky Note View Sticky Notes Tear Off Attach Charges Charge Entry Exit Calculator Message Sender AdHoc Communicate Schedule | List ↑ | Recent ▼ |

2320 — Dashboard | Registries | Scorecard | Medication | Outreach | Metrics | Program Analysis Print  5 minutes ago
Analytics 2322
2340 — Communications 2342 — Announcements ③
- Breast Cancer Awareness Month
  Wed Sep 11, 2013
- 2014 Incentive Plan Changes
  Wed Sep 11, 2013
- New Reports Available
  Wed Sep 11, 2013

2344 — Notifications ③
- Virginia Johnson
  Virginia Johnson scheduled today for heart failure with weight gain.
  Wed Sep 11, 2013                    Cindy Miller, Care Mgr 2336 — My Population ~ 2330

High Risk
(donut chart: 41, 135 Persons, 83, 59, 67)

☒ Multiple Chronic
☒ Utilizers
☒ PolyPharmacy
☒ All Categories

2334
Top 5 Chronic Diseases | Persons | Quality Score
Osteoarthritis | 97 | 70%
Heart Failure | 36 | 50%
Diabetes Mellitus | 47 | 80%
Hypertension | 51 | 90%
Behavioral Health | 73 | 55%

2332
Persons of Interest                 View More Persons ▷
Lowest Quality Score
Smith, Janet
Date 10/18/2013   Dx Diabetes
Montgomery, Jeff
Date 9/12/2013   Dx Diabetes
Hennings, Shelly
Date 9/12/2013   Dx Diabetes
Haggerty, David
Date 9/12/2013   Dx Diabetes
Stevenson, Sarah
Date 9/12/2013   Dx Diabetes

2360

2362 — Registries
68%
Quality Score
(slider)      72% Completion  [View]
1,465 Attributed Persons 2364 — Scorecard
62%
Composite Score
(slider)      +2.5 Top Opportunity
                   Tobacco Screening  [View]
325 Scorable Persons 2366 — Medications
45%
GDR
(slider)      4,231 RX claims
Generic Dispense Rate
Bisphosphonates  [View]

Population

COMPREHENSIVE MEDICATION ADVISOR

CROSS-REFERENCE TO RELATED APPLICATIONS

This Application is a continuation of U.S. patent application Ser. No. 14/502,316, filed Sep. 30, 2014, which claims priority to U.S. Provisional Application Ser. No. 61/885,359, filed Oct. 1, 2013, and U.S. Provisional Application Ser. No. 61/888,313, filed Oct. 8, 2013, herein incorporated by reference in their entireties, and is related to commonly assigned U.S. patent application Ser. No. 14/586,340, filed Dec. 30, 2014, entitled "Population-Based Medication Stewardship"; U.S. patent application Ser. No. 14/586,295, filed Dec. 30, 2014, entitled "Population Health Condition Worklist"; U.S. patent application Ser. No. 14/586,329, filed Dec. 30, 2014, entitled "Population Health Care Transition"; U.S. patent application Ser. No. 14/586,308, filed Dec. 30, 2014, entitled "Population Health Condition Management"; and U.S. patent application Ser. No. 14/586,338, filed Dec. 30, 2014, entitled "Population Health Situational Awareness," filed concurrently herewith on the same date.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Embodiments of the present invention generally relate to designing and utilizing population health programs to allow for cross-continuum tracking and subsequent interactions with transactional systems, providers, patients, etc. Clinically relevant algorithms may be utilized to populate registries, which can enable healthcare providers to better facilitate care for a population of patients. Comprehensive condition-specific and/or patient situation specific information may be consolidated and provided that is accessible and updatable by multiple providers and venues. Cross venue care related information (e.g., antibiograms based on culture, medications information, and/or susceptibility results) may be created which can be filtered for selected demographics. Multiple medication and/or treatment options including dosing, generic alternatives, cost, availability, and susceptibility information may be provided and inappropriate trends may be flagged and monitored so medication stewards can be alerted or notified to intervene.

Accordingly, in one aspect, an embodiment of the present invention is directed to one or more computer storage media storing computer-executable instructions that, when executed by one or more computing devices, cause the one or more computing devices to perform a method that facilitates designing and utilizing population health programs. The method includes receiving, at a population health server, healthcare data from disparate sources. The method further includes utilizing the population health server to identify a population of patients based on a set of criteria. The method also includes utilizing the population health server to stratify the population of patients based on one or more algorithms to create one or more groups of patients. At least one group of the one or more groups of patients comprises a plurality of patients having at least one substantially similar attribute. The method further includes utilizing the population health server to create at least one registry, the at least one registry comprising at least a portion of the one or more groups.

A further embodiment is directed to a system that includes one or more processors; and a non-transitory computer storage medium storing computer-useable instructions that, when used by the one or more processors, cause the one or more processors to: receive healthcare data from disparate sources; identify a population of patients based on a set of criteria; stratify the population of patients based on one or more algorithms; and create a registry for at least a portion of the population of patients, wherein the registry accounts for one or more of: resources available to a patient; lifestyle and prognostic assets that can be used for prediction; and assets necessary for attribution, allocation, or measurement.

In another embodiment of the invention, an aspect is directed to one or more computer storage media storing computer-executable instructions that, when executed by one or more computing devices, cause the one or more computing devices to perform a method that facilitates designing and utilizing population health programs. The method includes receiving, at a population health server, healthcare data from disparate sources. The healthcare data may comprise one or more of clinical data, healthcare-related financial data, and patient sensor and/or patient device data. The method further includes utilizing the population health server to identify a population of patients based on one or more medical conditions. The method also includes utilizing the population health server to stratify the population of patients into one or more groups based on at least one algorithm. Each group of the one or more groups may comprise one or more patients having a substantially similar medical condition. The method further includes providing an opportunity for a clinician to confirm an output of the at least one algorithm. The method also includes utilizing the population health server to create at least one registry for the population of patients based on at least a portion of the output of the at least one algorithm.

In another aspect, an embodiment of the present invention is directed to one or more computer storage media storing computer-executable instructions that, when executed by one or more computing devices, cause the one or more computing devices to perform a method for providing a cross venue antibiogram. The method comprises receiving medications information from disparate sources including information from multiple venues, multiple providers, and across multiple conditions. The method further comprises receiving susceptibility results based on testing associated with patient information from the disparate sources. The method also comprises creating a cross venue antibiogram based on the medications information and the susceptibility results. The method further comprises communicating the cross venue antibiogram to a clinician device.

In another embodiment of the invention, an aspect is directed to a computer-implemented method. The method includes receiving, from a clinician device, a selection of a disease state for a patient. The method further includes receiving patient information, from an Electronic Medical Record (EMR). The patient information includes related conditions, laboratory results, and allergy information for the patient. The method also includes utilizing susceptibility data, based on a cross venue antibiogram, to provide one or more medication options for the disease state. The antibiogram is based on medications information from disparate sources including multiple venues, multiple providers, and across multiple conditions. The method further includes providing the one or more medication options to the clinician device. The one or more medication options includes one or more of dosing, generic alternatives, cost, and availability.

A further embodiment is directed to a system that includes one or more processors; and a non-transitory computer storage medium storing computer-useable instructions that, when used by the one or more processors, cause the one or more processors to: receive medications information from disparate data sources, the data sources including multiple venues, multiple providers, and across multiple conditions; receive susceptibility results based on testing associated with patient information provided by the disparate sources; create a cross venue antibiogram based on the medications information and the susceptibility results; provide the cross venue antibiogram to a device associated with a clinician; and enable filtering of the cross venue antibiogram based on selected demographics, the selected demographics including an institution, a practice associated with a clinician, a zip code, a county, a city, a state, a region, or a country.

In another aspect, an embodiment of the present invention is directed to one or more computer storage media storing computer-executable instructions that, when executed by one or more computing devices, cause the one or more computing devices to perform a method for stratifying one or more patients into one or more groups. The method includes receiving, at a population health server, healthcare data, where the healthcare data includes clinical impressions and/or clinical narratives from one or more healthcare providers. The method further includes utilizing the population health server for natural language processing to extract one or more clinical indicators from the healthcare data. In addition, the method includes utilizing the population health server to stratify one or more patients into one or more groups based on at least a portion of the one or more clinical indicators. Furthermore, the method includes utilizing the population health server to create at least one registry including the one or more groups. The at least one registry accounts for one or more of: resources available to a patient; lifestyle and prognostic assets that can be used for prediction; and assets necessary for attribution, allocation, or measurement.

In another aspect, a further embodiment is directed to a computer system that stratifies one or more patients into one or more groups, the computer system including a processor coupled to a computer storage medium, the computer storage medium having stored thereon a plurality of computer software components executable by the processor. The computer software components include a receiving component that receives healthcare data, where the healthcare data includes clinical impressions and/or clinical narratives from one or more healthcare providers. The computer software components further include a natural language processing component that extracts one or more clinical indicators from the healthcare data, and a stratifying component that utilizes one or more algorithms to stratify one or more patients into one or more groups based on at least a portion of the one or more clinical indicators. In addition, the computer software components include a creating component that creates at least on registry. The at least one registry includes at least a portion of the one or more groups, where the at least one registry accounts for one or more of: resources available to a patient; lifestyle and prognostic assets that can be used for prediction; and assets necessary for attribution, allocation, or measurement.

In another aspect, an embodiment of the present invention is directed to one or more computer storage media storing computer-executable instructions that, when executed by one or more computing devices, cause the one or more computing devices to perform a method for stratifying one or more patients into one or more groups. The method includes receiving, at a population health server, healthcare data from disparate sources, where the healthcare data includes clinical impressions and/or clinical narratives from one or more healthcare providers. The method further includes utilizing the population health server for natural language processing to extract one or more clinical indicators from the healthcare data, where the one or more clinical indicators are associated with one or more chronic conditions. In addition, the method includes providing a relevance rating to each of the one or more clinical indicators, and utilizing the population health server to stratify one or more patients into one or more groups based on at least a portion of the one or more clinical indicators. Further, the method includes utilizing the population health server to create at least one registry including the one or more groups, where the at least one registry accounts for one or more of: resources available to a patient; lifestyle and prognostic assets that can be used for prediction; and assets necessary for attribution, allocation, or measurement.

In another aspect, an embodiment of the present invention is directed to one or more computer storage media storing computer-executable instructions that, when executed by one or more computing devices, cause the one or more computing devices to perform a method that facilitates using at least one clinically relevant algorithm in population health programs. The method includes receiving, at a population health server, healthcare data from disparate sources. The method further includes utilizing the population health server to stratify a population of patients based on one or more algorithms to create one or more groups of patients, where at least one group of the one or more groups of patients comprises a plurality of patients having at least one substantially similar attribute. The one or more algorithms include at least one clinically relevant algorithm utilizing clinical data. In addition, the method includes utilizing the population health server to create at least one registry, the at least one registry including at least a portion of the one or more groups.

In another aspect, a further embodiment is directed to a computer system that facilitates designing and utilizing population health programs, the computer system including a processor coupled to a computer storage medium, the computer storage medium having stored thereon a plurality of computer software components executable by the processor. The computer software components include a receiving component that receives healthcare data from disparate sources, and a stratifying component that stratifies a population of patients based on one or more algorithms. The one or more algorithms comprising at least one clinically relevant algorithm. The computer software components further include a creating component that creates a registry for at least a portion of the population of patients. The registry accounts for one or more of: resources available to a patient; lifestyle and prognostic assets that can be used for prediction; or assets necessary for attribution, allocation, or measurement.

In another aspect, an embodiment of the present invention is directed to one or more computer storage media storing computer-executable instructions that, when executed by one or more computing devices, cause the one or more computing devices to perform a method that facilitates utilizing clinically relevant algorithms for registry population. The method includes receiving, at a population health server, healthcare data from disparate sources, and utilizing the population health server to identify a population of patients based, at least partly, on one or more medical conditions. The method further includes utilizing the population health server to stratify the population of patients based on at least a clinically relevant algorithm. The clinically relevant algorithm utilizes clinical data, and the clinical data includes one or more of medication information, laboratory values, diagnostics, clinician narratives, and clinician assessments. In addition, the method includes utilizing the population health server to create at least one registry for the population of patients based on at least a portion of an output of the clinically relevant algorithm. The method further includes utilizing the population health server to update the at least one registry when additional clinical data is available for the clinically relevant algorithm to utilize.

BRIEF DESCRIPTION OF THE DRAWINGS

Embodiments are described in detail below with reference to the attached drawing figures, wherein:

FIGS. 14-27 depict illustrative screen displays, in accordance with exemplary embodiments of the present invention;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Currently there is not a comprehensive and convenient healthcare management system and/or method for a user, e.g., a healthcare provider, to understand populations of patients within their own transactional system, much less across a community or geographic area. Further, current population healthcare management systems are limited in that such systems do not effectively utilize various types of data associated with a population of patients, nor do such systems provide effective consistency across all venues and conditions.

Accordingly, various aspects of the technology described herein are generally directed to methods, systems, computer storage media, and graphical user interfaces for population health management. Various embodiments of the present invention are directed to facilitating the design and utilization of a population health management system to allow for cross-continuum tracking and subsequent interactions with transactional systems, providers, patients, etc. In embodiments, the population health management system can include utilizing clinically relevant algorithms to populate registries, which can enable healthcare providers to better facilitate care for a population of patients. In certain embodiments, the population health management system can consolidate and provide comprehensive condition-specific and/or patient situation specific information that is accessible and updatable by multiple providers and venues. In embodiments, the population health management system can create cross venue antibiograms based on medications information and susceptibility results which can be filtered for selected demographics. In embodiments, the population health management system can be utilized to provide multiple medication options including dosing, generic alternatives, cost, availability, and susceptibility information. In embodiments, inappropriate trends may be flagged and monitored and medication stewards may be alerted or notified to intervene.

Figure 1:
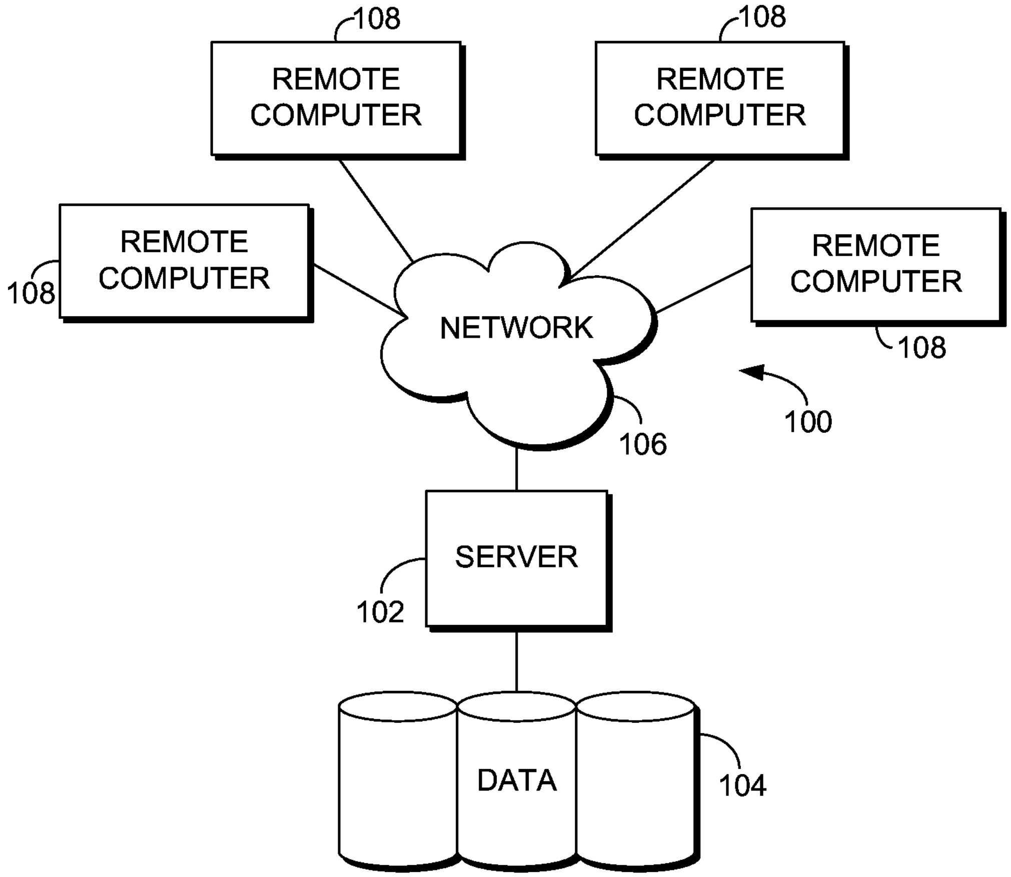
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians or healthcare providers may comprise a treating physician or physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
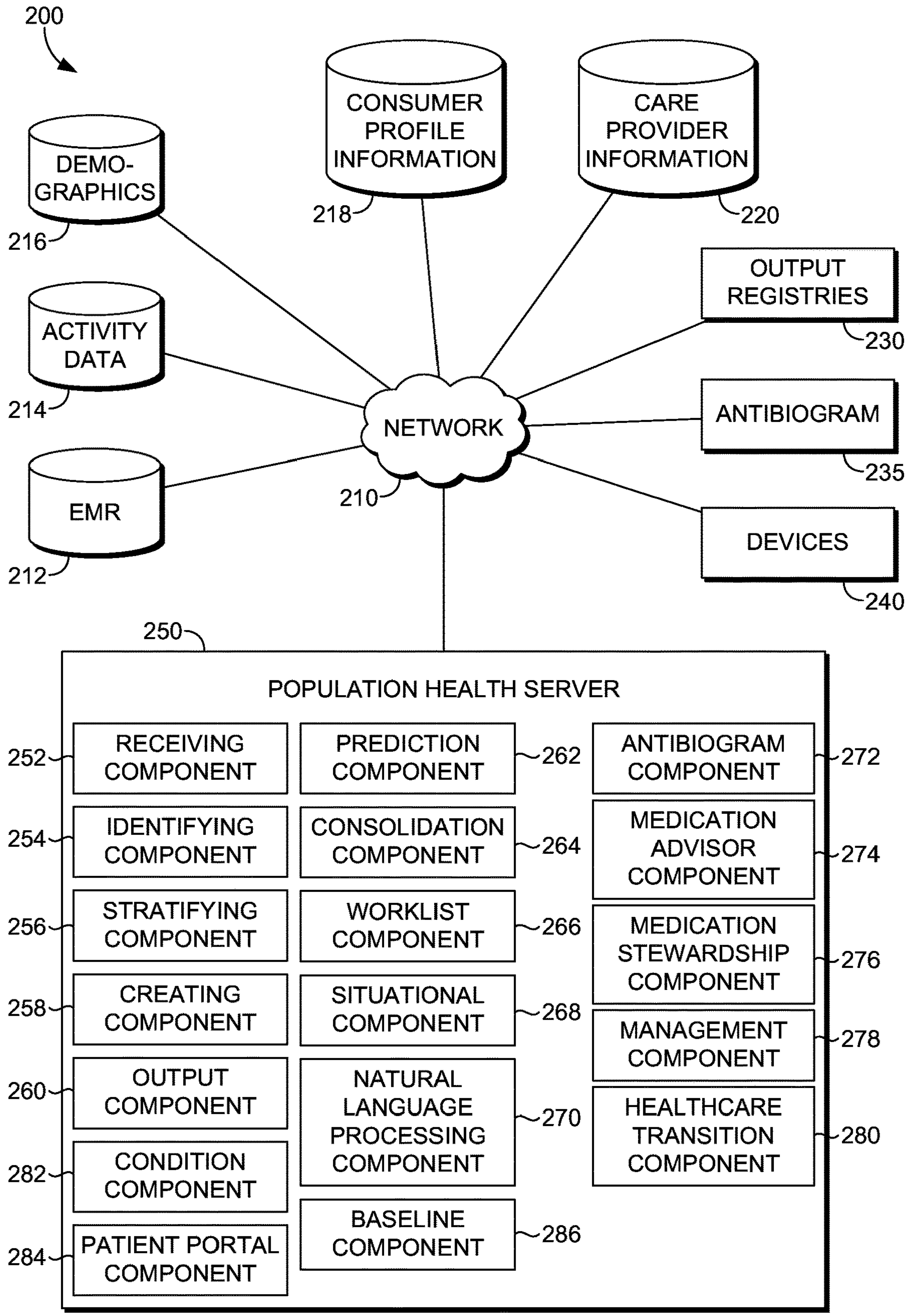
FIG. 2 is a block diagram of an exemplary population health management system to implement embodiments of the present invention.

Turning now to FIG. 2, an exemplary population health management system 200 suitable for use in implementing embodiments of the present invention is depicted. The population health management system 200 is merely an example of one suitable computing system environment and is not intended to suggest any limitation as to the scope of use or functionality of embodiments of the present invention. Neither should the population health management system 200 be interpreted as having any dependency or requirement related to any single module/service/component or combination of modules/services/components illustrated therein.

The population health management system 200 may include a population health server 250, electronic medical records 212 (EMRs), activity data 214 patient and/or population demographic information 216, consumer profile information 218, provider information 220, one or more output registry databases 230, and/or one or more computing devices 240, all in communication with each other through wired or wireless connections and/or through the network 210. The network 210 may include, without limitation, one or more local area networks (LANs) and/or wide area networks (WANs). Such networking environments are commonplace in offices, enterprise-wide computer networks, intranets and the Internet. Accordingly, the network is not further described herein.

In embodiments, the EMRs 212 may span multiple applications, multiple providers, multiple patients, multiple conditions, multiple venues, multiple facilities, multiple organizations, and/or multiple communities. Embodiments of the EMRs 212 may include one or more data stores of healthcare records, which may include one or more computers or servers that facilitate the storing and retrieval of the healthcare records. In some embodiments, one or more EMRs 212 may be implemented as a cloud-based platform or may be distributed across multiple physical locations. Example embodiments of the EMRs 212 may include hospital, ambulatory, clinic, health exchange, and health plan records systems. The EMRs 212 may further include record systems, which store real-time or near real-time patient (or user) information, such as wearable, bedside, or in-home patient monitors, for example. It is further contemplated that embodiments of the EMRs 212 may use distinct clinical ontologies, nomenclatures, vocabularies, or encoding schemes for clinical information, or clinical terms. Further, in some embodiments, the EMRs 212 may be affiliated with two or more separate health care entities and/or venues that use two or more distinct nomenclatures.

In embodiments, the EMRs 212 described herein may include healthcare data. As used herein, healthcare data refers to any healthcare or medical care data related or relevant to a patient. Healthcare data may include, but is not limited to, clinical data and healthcare-related financial data. Clinical data, as used herein, refers to any healthcare or medical data particular to a patient. In embodiments, clinical data can be medical care or healthcare data resulting from or associated with a health or medical service performed in association with a clinician in a healthcare environment (e.g., lab test, diagnostic test, clinical encounter, ecare, evisit, etc.). Clinical data may include, but is not limited to, a health history of a patient, a diagnosis, a clinician assessment, clinician narrative, a treatment, a family history (including family health history and/or family genetics), an immunization record, a medication, age, gender, date of birth, laboratory values, diagnostics, a test result, an allergy, a reaction, a procedure performed, a social history, an advanced directive, frequency and/or history of healthcare facility visits, current healthcare providers and/or current healthcare provider location, preferred pharmacy, prescription benefit management data, an alert, claims data, a vital, data traditionally captured at the point of care or during the care process, a combination thereof, and the like. In the same or alternative embodiments, the clinical data may include medical compliance information. In certain embodiments, medical compliance information refers to a level of compliance of a particular patient with one or more prescribed medical treatments, such as medications, diet, physical therapy, follow up healthcare visits, and the like. In one or more embodiments, the clinical data may include data obtained from the natural language processing of one or more clinical assessments and/or clinical narratives.

In certain embodiments, healthcare-related financial data can refer to any financial information relevant to a patient, such as insurance data, claims data, payer data, etc. Such healthcare data (e.g., clinical data and healthcare-related financial data) may be submitted by a patient, a care provider, a payer, etc. In certain embodiments where the healthcare data is being submitted by anyone other than the patient, the patient may be required to approve of such submission and/or may opt-in to or opt-out of having such healthcare data being submitted.

In embodiments, activity data 214 can refer to health actions or activities performed by a patient outside of, or remote from, a healthcare environment. Embodiments of activity data 214 may include one or more data stores of activity data 214, which may include one or more computers or servers that facilitate the storing and retrieval of the activity data 214. In some embodiments, the activity data 214 may be implemented as a cloud-based platform or may be distributed across multiple physical locations. Example embodiments of the activity data 214 may include nutrition information and/or exercise information for a patient. In certain embodiments, at least a portion of the activity data 214 may be recorded utilizing a personal fitness tracker, a smart phone, and/or an application provided by a smart phone. In various embodiments, the activity data 214 may include data obtained from a patient's car. For example, in such embodiments, the activity data 214 may include data on the amount of driving the patient does versus the amount of walking the patient does.

In one or more embodiments, the activity data 214 may be submitted by a patient, a third party associated with a personal fitness tracker and/or smart phone (such as a software developer or device manufacturer), a care provider, a payer, etc. In certain embodiments where the activity 214 is being submitted by anyone other than the patient, the patient may be required to approve of such submission and/or may opt-in to or opt-out of having such healthcare data being submitted.

The patient and/or population demographic information 216 may include age, gender, date of birth, address, phone number, contact preferences, primary spoken language, technology access (e.g., internet, phone, computer, etc.), transportation (e.g., common modes of transportation), education level, motivation level, work status (student, full-time, retired, unemployed, etc.), and/or income. In certain embodiments, the patient and/or population demographic information 216 may include community resource information, which may include, but is not limited to, fitness facility information, pharmacy information, food bank information, grocery store information, public assistance programs, homeless shelters, etc. In embodiments, the motivation level can include the level of motivation a particular patient has for maintaining their health, which may be derived from other information (e.g., data from personal fitness tracker, indication the patient regularly visits a clinician for check-ups, consumer profile information, etc.). Embodiments of the patient and/or population demographic information 216 may include one or more data stores of demographic information 216 which may include one or more computers or servers that facilitate the storing and retrieval of the demographic information 216. In some embodiments, the patient and/or population demographic information 216 may be implemented as a cloud-based platform or may be distributed across multiple physical locations. In embodiments, the patient and/or population demographics 216 may be obtained through any source known to one skilled in the art. For example, in certain embodiments, at least a portion of the patient and/or population demographic information 216 may be submitted by a third party that relies on census data. In various embodiments, the patient and/or population demographic information 216 may be obtained from more than one source. In one embodiment, the patient may submit any or all of the patient and/or population demographic information 216. In certain embodiments, all or a portion of the patient and/or population demographic information 216 may be anonymized using techniques known to one skilled in the art.

In one or more embodiments, the consumer profile information 218 may include any or all of the spending habits of one or more patients within a population. For instance, in certain embodiments, the consumer profile information 218 may include information associated with grocery store purchases, athletic or exercise equipment purchases, restaurant purchases, and/or purchases of vitamins and/or supplements. Embodiments of the consumer profile information 218 may include one or more data stores of consumer profile information 218 which may include one or more computers or servers that facilitate the storing and retrieval of the consumer profile information 218. In some embodiments, the consumer profile information 218 may be implemented as a cloud-based platform or may be distributed across multiple physical locations. In one embodiment, a patient may provide the consumer profile information 218, for example, by linking checking account and/or checking account purchase information to at least a portion of the population health management system 200 and/or to a health insurance carrier.

The care provider information 220 may include any information relating to a particular care provider or healthcare facility. In one embodiment, the care provider information 220 may include information relating to the number of healthcare providers and their specialties at a particular care provider location. In the same or alternative embodiments, the care provider information 220 may include information relating to non-personnel type resources at a particular care provider location, such as the amount and types of medications and/or the amount and types of surgical or other medical equipment. In one embodiment, the care provider information 220 may include one or more of address and contact information, accepted payer information, status on accepting new patients, transactional systems, primary spoken language, hospital affiliations, and/or care delivery models. In embodiments, the care provider information 220 may include information relating to the availability of any or all resources at a particular healthcare facility including personnel and/or non-personnel resources. Embodiments of the care provider information 220 may include one or more data stores of care provider information 220 which may include one or more computers or servers that facilitate the storing and retrieval of the care provider information 220. In some embodiments, the care provider information 220 may be implemented as a cloud-based platform or may be distributed across multiple physical locations. In one embodiment, the care provider information 220 can be provided by a healthcare provider, and/or a third party, such as an insurance provider or management entity.

In one or more embodiments, the output registry databases 230, which may include the output registries, may be networked storage or distributed storage including storage on servers located in the cloud. Thus, it is contemplated that for some embodiments, the information stored in the output registry databases 230 is not stored in the same physical location. The information within the output registry databases 230 may exist in a variety of standardized formats including, for example, narratives and other data. Information in the output registry databases 230 may be categorized or classified according to, for example, claims, diagnoses, wellness, satisfaction, population directories, and the like.

In various embodiments, each output registry may be used by, for example, a healthcare organization to manage the health of a population segment. In one or more embodiments, each output registry may be condition specific. By way of example, a healthcare organization or clinician may manage diabetic patients within a proscribed geographic area. The condition in this example is diabetes mellitus and the output registry may help the healthcare organization manage a population segment with this condition. The output registry may, in one aspect, include identified patients within a population segment who have this condition or have risk factors that may lead to the development of diabetes, such as those identified by the identifying component 254 of the population health server 250. The output registry may further include stratified patients within an identified segment by degree of severity or risk, such as those stratified by the stratifying component 256 of the population health server 250. The stratified patients in an output registry may facilitate the generation of interventions or action workflows designed to reduce disease severity or risk and to improve outcome. Additional uses for the output registries are to measure outcomes related to treatment interventions and also to attribute patients within the identified segment to appropriate healthcare providers (e.g., primary care physicians, care managers health coaches, specialists such as endocrinologists, podiatrists, and the like).

In embodiments, the devices 240 can include a remote computer, such as the remote computers 108 discussed above with reference to FIG. 1. In one or more embodiments, the devices 240 can include any or all of the properties and parameters of the remote computers 108 discussed above with reference to FIG. 1. In certain embodiments, any or all portions of output generated by the population health server, e.g., the output registries 230, the antibiogram database 235, etc., may be provided to or accessible via one or more of the devices 240.

The population health server 250 depicted in FIG. 2 is merely exemplary. While the population health server 250 is illustrated as a single unit, it will be appreciated that the population health server 250 may include one or more separate components, services, and/or modules. Further in embodiments, the population health server 250 may be scalable. For example, the population health server 250 may in actuality include a plurality of computing devices in communication with one another. Components of the population health server 250 may include a processing unit, internal system memory, and a suitable system bus for coupling various system components, including one or more data stores for storing information (e.g., files and metadata associated therewith). In embodiments, each of these components/services/modules typically includes, or has access to, a variety of computer-readable media.

In some embodiments, one or more of the illustrated components of the population health server 250 may be implemented as one or more stand-alone applications. Further, various components, services, and/or modules may be located on any number of servers. By way of example only, the population health server 250 might reside on a server, cluster of servers, a cloud-computing device or distributed computing architecture, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components and/or modules, and in any suitable combination and location. Various functions described herein as being performed by one or more entities may be carried out by hardware, firmware, and/or software. For instance, various functions described herein with reference to the population health server 250 may be carried out by a processor executing instructions stored in memory.

As discussed above, the population health server 250 may comprise one or more components, services, and/or modules. For example, as depicted in FIG. 2, the population health server 250 may include a receiving component 252, an identifying component 254, a stratifying component 256, a creating component 258, an output component 260, a prediction component 262, a consolidation component 264, a worklist component 266, a situational component 268, a natural language processing component 270, an antibiogram component 272, a medication advisor component 274, a medication stewardship component 276, a management component 278, a healthcare transition component 280, a condition component 282, a patient portal component 284, and a baseline component 286. In certain embodiments, one or more of the components 252, 254, 256, 258, 260, 262, 264, 266, 268, 270, 272, 274, 276, 278, 280, 282, 284, and 286 may be configured to provide or convey information that can populate a graphical user interface, which may be viewed on a device, such as one of the devices 240.

In one or more embodiments, one or more of the components 252, 254, 256, 258, 260, 262, 264, 266, 268, 270, 272, 274, 276, 278, 280, 282, 284, and 286 may be implemented as stand-alone applications. In other embodiments, one or more of the components 252, 254, 256, 258, 260, 262, 264, 266, 268, 270, 272, 274, 276, 278, 280, 282, 284, and 286 may be integrated directly into the operating system of a computing device, such as the remote computer 108 of FIG. 1 and/or the one or more computing devices 240 of FIG. 2. It will be understood that the components 252, 254, 256, 258, 260, 262, 264, 266, 268, 270, 272, 274, 276, 278, 280, 282, 284, and 286 illustrated in FIG. 2 are exemplary in nature and in number and should not be construed as limiting. Any number of components and/or modules may be employed to achieve the desired functionality within the scope of embodiments hereof.

In certain embodiments, the receiving component 252 can receive healthcare data from disparate sources. In one or more embodiments, the disparate sources may include one or more EMRs, e.g., the EMRs 212, each of which may be independent from one another. In certain embodiments, the disparate sources may include a plurality of EMRs, e.g., the EMRs 212. In embodiments, the plurality of EMRs may be associated with a plurality of healthcare providers, a plurality of patients, a plurality of medical conditions, a plurality of healthcare venues and/or facilities, a plurality of organizations, and/or a plurality of communities. In certain embodiments, at least a portion of the EMR's received by the receiving component 252 may be associated with the same patient.

In one or more embodiments, in addition to or in place of the healthcare data, the receiving component 252 can receive one or more of activity data, e.g., the activity data 214; demographic information, e.g., the patient and/or population demographic information 216; consumer information, e.g., the consumer profile information 218; and provider information, e.g., the care provider information 220. In such embodiments, the activity data, the demographic information, the consumer information, and/or the provider information may be provided by or obtained from one or more sources, e.g., the sources discussed above with reference to the activity data 214, the patient and/or population demographic information 216, the consumer profile information 218, and/or the care provider information 220.

In embodiments, the identifying component 254 can identify a population of patients based on a set of criteria, which may, in one example, be received from a clinician device 240. In one or more embodiments, the set of criteria may include one or more medical conditions. In the same or alternative embodiments, the set of criteria may include demographic information of one or more patients, such as age, gender, race, and/or location of residence. In one or more embodiments, the identifying component 254 may utilize any or all of the information and data received by the receiving component 252, such as: healthcare data, e.g., the healthcare data present in one or more EMRs 212; activity data, e.g., the activity data 214; demographic information, e.g., the patient and/or population demographic information 216; consumer information, e.g., the consumer profile information 218; and provider information, e.g., the care provider information 220.

In embodiments, the identifying component 254 can identify a subset of the healthcare data associated with an individual patient related to a particular medical condition of interest. In the same or alternative embodiments, the identifying component 254 can identify one or more patients in a population of patients having a medical condition of interest. In various embodiments, the identifying component 254 can identify healthcare data and/or a patient in a population of patients associated with any medical condition of interest. In various embodiments, data associated with one or more patients identified by the identifying component 254 may be provided to one or more output registries, such as the one or more output registry databases 230.

In certain embodiments, to identify as many people as possible in a population that may have or have a particular medical condition of interest, the identifying component 254 may utilize clinical data, such as lab test results, in combination with other healthcare data. In such embodiments, the particular medical condition can be any condition where specific types of clinical information, e.g., lab test results, may be used to identify one or more patients that have or may have that condition. Exemplary conditions may include, but are not limited to, diabetes and heart disease. For example, in embodiments, the identifying component 254 may utilize diagnostic information, medication information, and/or one or more lab test results to identify a patient as having or potentially having diabetes. In such embodiments, by having the identifying component 254 utilize information from one or more lab test results, the identifying component 254 may identify one or more patients that have diabetes or may have diabetes, even if they have not been formally diagnosed with diabetes or have not been prescribed diabetes medication. In the same or alternative embodiments, the identifying component 254 may utilize lab test results in combination with other healthcare data to identify precondition patients, which may allow early intervention to prevent a patient from developing a particular condition.

In one or more embodiments, the identifying component 254 can identify subsets of a population not based on a medical condition. For instance, in such embodiments, the identifying component 254 can identify subsets of a population based on aspects of one or more patients in a population of patients, e.g., age, gender, primary spoken language, income level, healthcare motivation level, education level, technology access (e.g., phone, computer, etc.), contact preferences, work status (student, full-time, unemployed, retired, etc.), healthcare facility visit history and frequency, advanced directives, and/or consumer profile information. In embodiments, the identifying component 254 can identify specific care provider information, such as address and contact information of a healthcare facility, primary spoken language of the healthcare facility, status on acceptance of new patients, etc. In one or more embodiments, the identifying component 254 can identify population and or community based resources, such as fitness centers, pharmacies, food banks, public assistance, homeless shelters, etc.

In various embodiments, the identifying component 254 can identify subsets of a population based on non-medical aspects of patients, specific care provider information, and/or population and/or community based resources in order to enable actions and care planning, measure compliance, improve care transitions, optimize utilization of resources, and contain costs. In such embodiments, the identifying component 254 can identify subsets of a population based on non-medical aspects of patients, specific care provider information, and/or population and/or community based resources and populate such subsets into an output registry 230. Further, in such embodiments, the identified subsets can be utilized by other components of the population health server 250, such as the stratifying component 256 and/or the prediction component 262. Exemplary identification processes that may be performed, at least in part, by the identifying component 254 are further discussed below with reference to FIGS. 3 and 9.

In embodiments, the stratifying component 256 can stratify a population of patients based on one or more algorithms. In certain embodiments, the population of patients may include at least a portion or all of the population of patients identified by the identifying component 254. In one or more embodiments, the stratifying component 256 may receive data (such as a listing of names or identification information) of at least a portion of the population of patients from the identifying component 254 via the network 210. In the same or alternative embodiments, the stratifying component 256 may receive data (such as a listing of names or identification information) of at least a portion of the population of patients from the output registry databases 230 via the network 210.

In one or more embodiments, the stratifying component 256 can stratify a population of patients based on a clinically relevant algorithm. In such embodiments, the clinically relevant algorithm may utilize clinical data. In one or more embodiments, the clinical data may be provided from one or more EMRs, such as the EMRs 212. For example, in embodiments, the clinical data may include one or more of medication information, laboratory values, diagnostics, clinical narratives, and clinician assessments. In the same or alternative embodiments, the clinical data may include data obtained from the natural language processing of one or more clinical assessments and/or clinical narratives. In certain embodiments, the stratifying component 256 can stratify a population of patients based on diagnostic codes, intervention codes, insurance claims, and/or medication information associated with each patient. In one or more embodiments, the output of one or more algorithms associated with the stratifying component 256 may be provided to an output registry that may be, for example, stored in one of the output registry databases 230. In certain embodiments, an output registry can be updated when additional healthcare data, e.g., clinical data, is available for an algorithm, e.g., a clinically relevant algorithm, to utilize. In such embodiments, the stratifying component 256 may re-stratify a population of patients when such additional clinical data is available for the clinically relevant algorithm to utilize.

In various embodiments, the stratifying component 256 can stratify a population of patients into one or more groups, where the one or more groups can include a plurality of patients having at least one substantially similar attribute. In such embodiments, the substantially similar attributes can include one or more of disease risk levels and/or scores, one or more disease stages, and/or one or more healthcare objectives. For example, in certain embodiments, the stratifying component 256 can stratify a population of patients, such as a population of patients identified as having or potentially having diabetes, into at least two groups corresponding to Type I and Type II diabetes. In certain embodiments, as discussed below with reference to the output component 260, a clinician may be provided an opportunity to confirm the output of one or more algorithms, such as an algorithm utilized with the stratifying component 256.

In one or more embodiments, the stratifying component 256 may stratify information unrelated to specific medical conditions. For example, in certain embodiments, the stratifying component 256 can stratify a subset of care providers based on venue location, specialty, spoken language, turnover rate, readmission rate, patient satisfaction, availability, etc. Further, in certain embodiments, the stratifying component 256 can stratify one or more patients based on medical and/or prescription compliance level, socioeconomic status, associated healthcare support system, and/or utilization level of healthcare facilities (including pharmacies).

In one embodiment, an exemplary stratification process to stratify one or more patients with respect to medication compliance, which may be at least partly performed by the stratification component 256, can include stratifying individual patients as having a low, medium, or high medication compliance risk based on information related to the ability to access a pharmacy, the ability to pay for medications, and/or the presence of medication gaps in the healthcare record.

In certain embodiments, another exemplary stratification process to stratify one or more patients with respect to visit compliance, which may be at least partly performed by the stratification component 256, can include stratifying patients as having a high, medium, or low visit compliance level for any or all of the various types of healthcare venues. In such embodiments, individual patients may be stratified based on the number of appointments made, the number of appointments scheduled, the number of appointments attended, the number of missed appointments, the type of appointment, the date and time of the appointment, the visit location, the venue, and whether or not the patient acknowledged the appointment (e.g., was the patient aware of the appointment).

In one or more embodiments, another exemplary stratification process to stratify one or more patients with respect to their compliance for filling prescriptions, which may be at least partly performed by the stratification component 256, can include stratifying patients as having a low, medium, or high level of compliance with filling prescriptions based, at least in part, on the number of prescriptions written, the number of prescriptions filled, and the date and time the prescriptions were filled.

In another embodiment, an exemplary stratification process to stratify one or more patients as having one or more specific socioeconomic barriers to healthcare, which may be at least partly performed by the stratification component 256, can include stratifying one or more patients based on socioeconomic indicators, such as address, employment status, marital status, education level, age, sex, dependents, race, ethnicity, insurance status, and primary spoken language.

In one embodiment, an exemplary stratification process to stratify one or more patients as having a low, medium, or high level of support outside of a healthcare facility, which may be at least partly performed by the stratification component 256, can include stratifying one or more patients based, at least in part, on a patient living situation, marital status, disposition, caregiver status, and/or likelihood of utilization of resources (family, personal, professional, community, etc.).

In another embodiment, an exemplary stratification process to stratify one or more patients as having a low, medium, or high level of healthcare services utilization, which may be at least partly performed by the stratification component 256, can include stratifying one or more patients based, at least in part, on the number of provider visits, claims data, facility visits, and medication usage. Additional exemplary stratification processes, which, in embodiments, may be at least partially performed by the stratification component 256, are described below with reference to FIGS. 4 and 10.

In embodiments, the creating component 258 can create one or more output registries for one or more groups of patients of a population of patients, e.g., one or more groups identified and/or created by the identifying component 254 and/or the stratifying component 256. The output registries may account for resources available to a patient, lifestyle and prognostic assets that can be used for prediction, and assets necessary for attribution, allocation, or measurement. The output registries may be stored in one or more output registry databases 230 and may be accessible via the network 210. In certain embodiments, the output registries may include patient data relevant to a population of patients.

As discussed above, the stratifying component 256 may re-stratify one or more patients when additional healthcare data is available for a stratification algorithm to utilize. In such embodiments, the creating component 258 may update one or more output registries based on such a re-stratification of one or more patients.

In certain embodiments, by having particular patients in a particular registry associated with a specific medical condition, e.g., a registry having patients with Type I diabetes, a health system may be able to provide proposed plans specific to at least a portion of the patients in a particular registry. For example, in one embodiment, a Type I diabetes registry may be utilized to provide a proposed plan of care for a Type I diabetic patient, and a Type II diabetes registry may be utilized to provide a proposed plan of care for a Type II diabetic patient. In such embodiments, the proposed plans of care for the Type I and Type II diabetic patients may be different.

In embodiments, the output component 260 can provide clinical qualification of algorithm output, such as an algorithm utilized with the stratifying component 256. For example, in embodiments, a clinician may be provided an opportunity to see the data utilized by the stratifying component 256 to confirm the output of one or more algorithms. In the same or alternative embodiments, a clinician may be provided an opportunity to change the stratification level assigned to one or more patients. For example, in one embodiment, a clinician may change the heart failure classification of one or more patients after an in-person examination and/or after looking at the healthcare records associated with the one or more patients. In certain embodiments, the clinician may also have the opportunity to comment on the output and/or make additional decisions (e.g., prescriptions, interventions, and the like) based on the output.

In embodiments, the prediction component 262 can provide a prediction of problems or avoidable complications and can trigger events and alerts associated with the patient. In certain embodiments, the healthcare provider may also be provided with a prediction of problems the patient may encounter. In the same or alternative embodiments, the healthcare provider can also trigger events to happen, send alerts to people, and identify the potential of having an avoidable complication within the next twelve months. For example, the prediction component 262 may indicate that a patient has a high risk of a heart related issue, and trigger events and/or alerts so that the patient is seen by a cardiologist, is checked more frequently, and is confirmed to be taking the appropriate prophylactic medication. In certain embodiments, the prediction component 262 can predict: patient compliance levels for various treatments or medications; the need for transition care; readmission rates, emergency department re-entry rates, future healthcare costs; future patient attrition; comorbidity trending; and/or the amount of care provider resources needed based on patient population information.

In embodiments, the consolidation component 264 can consolidate the healthcare data for a patient across all venues and healthcare facilities, e.g., for any or all of the EMRs 212 associated with a particular patient. In such embodiments, this can allow all clinical support decisions across all venues and programs to be consolidated for the patient. In other words, the consolidation component 264 may consolidate data without regard to a specific condition or venue. In embodiments, the consolidation component 264 can piece together information from all programs that have been alerted or notified or found something out about a patient and consolidate that information for use by a healthcare provider when treating the patient.

In embodiments, the worklist component 266 can provide a filterable worklist for at least a portion of information contained in one or more registries, such as a registry in the output registry database 230. In such embodiments, a worklist may include a patient's name, risk level, location, clinical issues and alerts, care planning, payer information, demographics, medication information, and/or appointments. In the same or alternative embodiments, the worklist can include a list of patients from a registry, such as a registry in the output registry database 230, where the patients may be associated with a substantially similar medical condition. Further, the worklist may support, across multiple venues, multiple providers, and/or multiple conditions, providing actionable decision support tools and interventions, linking between applications and enabling documentation for one or more healthcare providers.

In embodiments, a worklist can link or connect information and workflows from separate venues (and across a community). In such embodiments, the worklist may be a reference point for healthcare providers, including care managers, specialist providers, and primary care providers. In one or more embodiments, the worklist may be parsed by healthcare providers, venue, and/or condition.

In embodiments, the worklist can provide a manageable list of cross-continuum, cohort specific patients that may be available to a healthcare provider or administrative body. In certain embodiments, the worklist may include criteria specific to the condition of interest, such as demographic factors, type and severity of disease, risk factors, and locality. In such embodiments, the worklist can provide contextuality of the designated cohort to the end-user, e.g., the healthcare provider, and enable efficiencies for population surveillance and resource allocation. In certain embodiments, the worklist may enable cross-continuum monitoring of a variety of activities by providing for the end-user, e.g., the healthcare provider, the ability to monitor events that have occurred or are occurring in near real-time, e.g., within 1 minute, 10 minutes, 30 minutes, 60 minutes, 120 minutes, 240 minutes, or 480 minutes of the event, outside of any one particular transactional system or EMR domain. In embodiments, the worklist may support actionable decision support tools and linking between applications to assist healthcare providers in the care of condition specified populations.

In one or more embodiments, the worklist may be a near real-time dynamic list of patients from a cohort. As used herein, near real-time dynamic list can mean a dynamic list that contains updated information that is available for viewing within at least about 1 minute, 10 minutes, 30 minutes, 60 minutes, 120 minutes, 240 minutes, or 480 minutes of such information being inputted into an associated population health management system. In certain embodiments, a worklist can enable a healthcare provider to identify patients in a particular program and understand tasks that need to be performed by the healthcare provider or others, as well as identify the status of those tasks. For example, in a hypertension care program setting, a worklist may enable a healthcare provider managing a particular group of patients with hypertension to determine how often their blood pressure should be monitored. In embodiments, if data elements are missing on a particular patient, the healthcare provider may be provided details in a historical and/or longitudinal view. In such embodiments, the details in a historical and/or longitudinal view can enable the healthcare provider to determine: if an appointment was set; if a call to the patient is needed, if help scheduling an appointment is needed; if help getting a prescription filled is needed; if a prescription was not filled; and/or why a patient missed an appointment (e.g., no ride, no money, forgot, in hospital somewhere, etc.). A worklist may also enable one or more healthcare providers to send out group communications or announcements and filter such communications or announcements by venue. Further, in one or more embodiments, a worklist may facilitate interventions. In certain embodiments, a worklist may be dynamic and automatically repopulate as patients enter or are removed from a particular care program.

Figure 16:
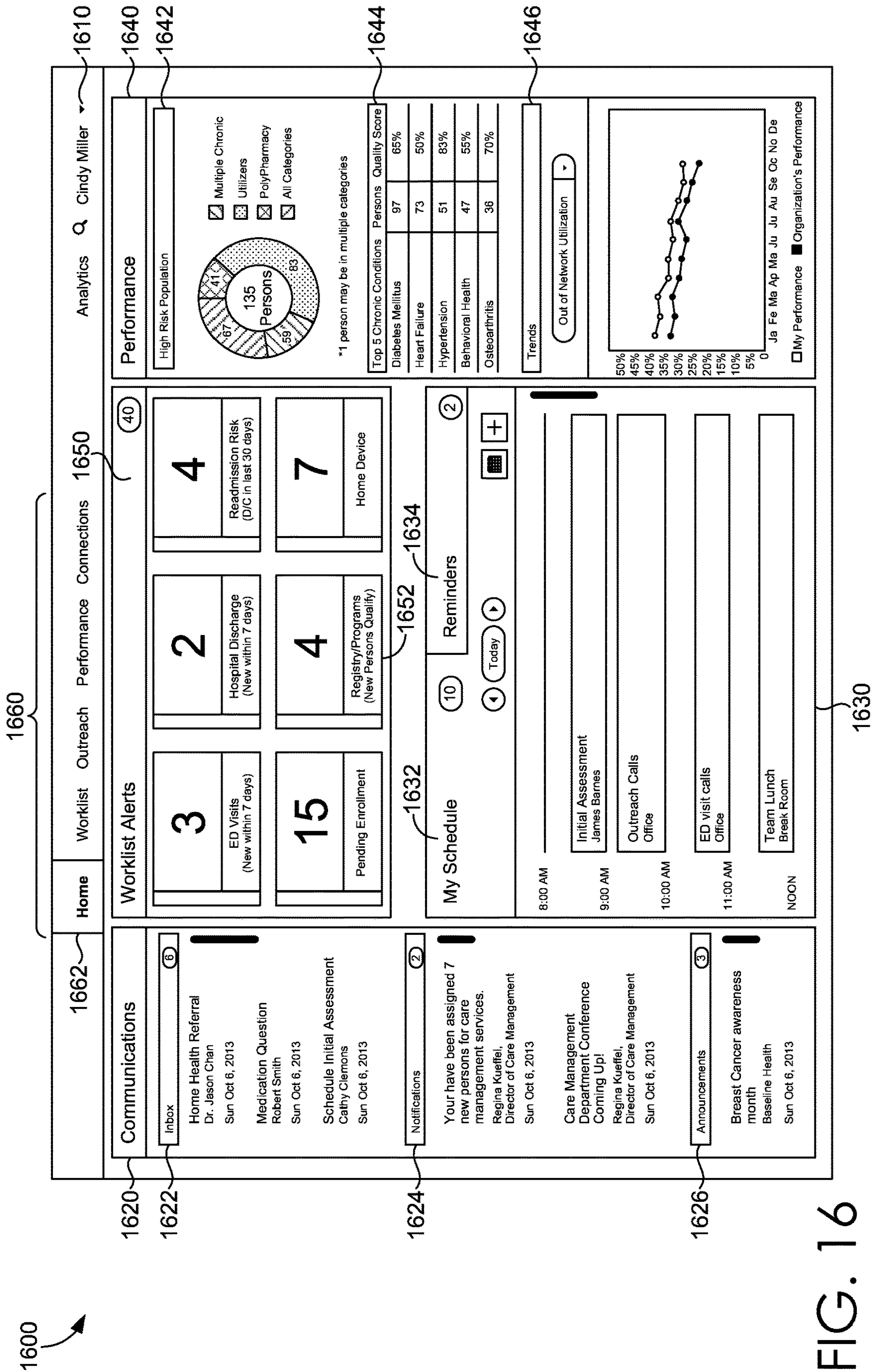
Figure 18:
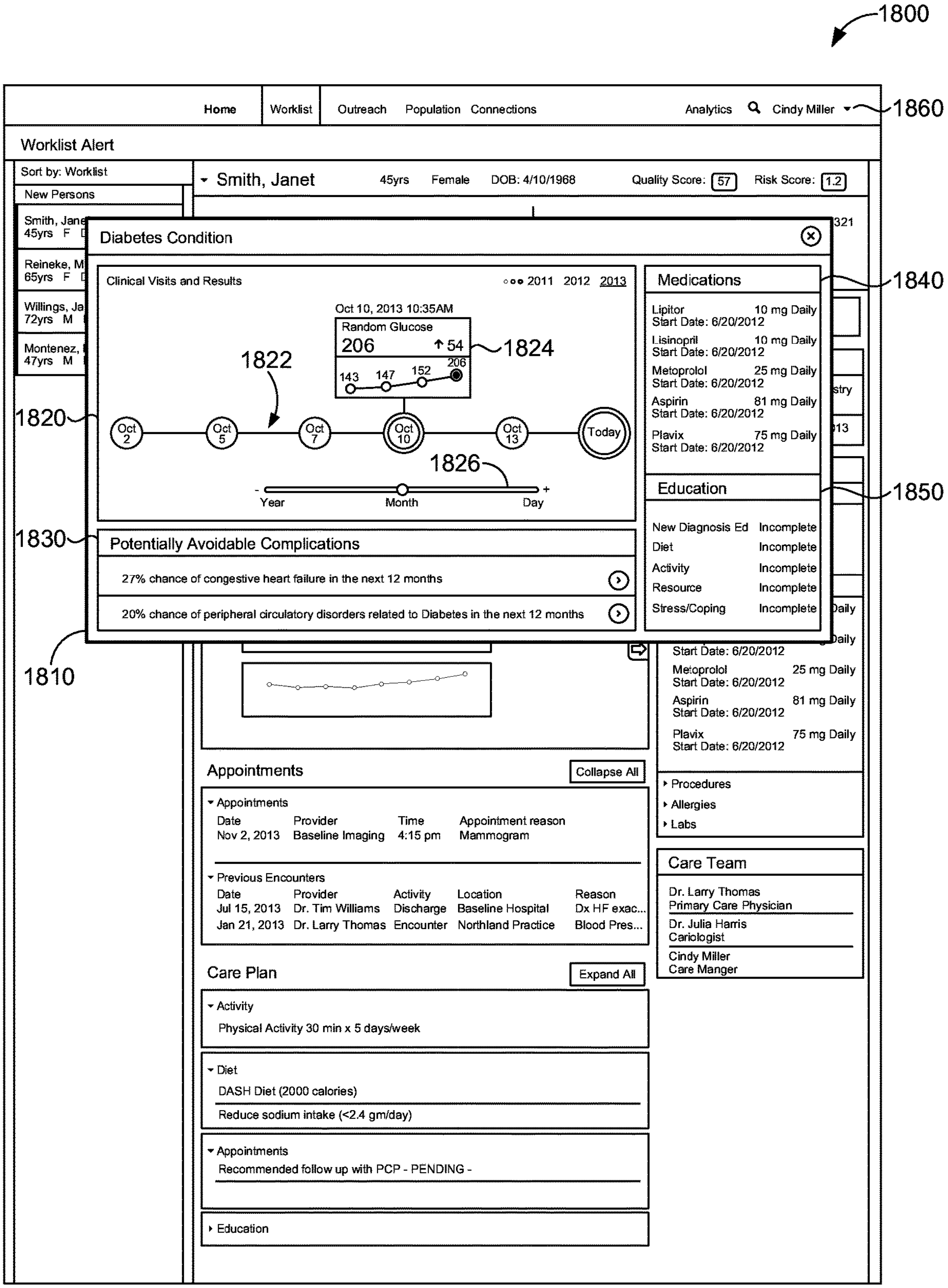

In embodiments, the worklist may be a standalone application and/or interface, e.g., the worklist may be available to end-users, e.g., healthcare providers, agnostic of EMRs or a transactional system. In certain embodiments, the worklist may comprise rows of patient names, columns to represent a variety of topics, and/or filtering capability to allow for individual use preferences. In such embodiments, examples of columns (which may be flexible based on the condition of interest) may include risk level, location, clinical issues/alerts, care planning, payer, demographics, medication information, and/or appointments. In addition to filtering, in embodiments, the worklists may facilitate linking, documentation, notes, and the like, all from a single source across venues. Exemplary worklists, which, in embodiments, may be at least partially created by the worklist component 266, are depicted in FIGS. 16, 17, and 18.

In embodiments, the situational component 268 can provide a patient specific preview that includes consolidated data across multiple providers, venues, and conditions to facilitate care by one or more healthcare providers. The situational component 268 may connect healthcare providers and/or end-users to a consistent flow of information from the population health management system 200, and may provide an efficient view of outputs without interrupting, and may enable cross-venue/cross-role communications. In embodiments, the situational component 268 may be patient-specific, but may consolidate and reconcile information across condition based programs.

In certain embodiments, the situational component 268 can capture and display time sensitive, patient-specific information within the purview of multiple, cross-continuum healthcare providers and may provide patient-specific information that has been generated from the population health management system 200.

In embodiments, the situational component 268 can provide a patient specific preview within a single view on a portion of a home page or viewing page. In one or more embodiments, the patient specific preview may operate across multiple programs/conditions while remaining patient-specific. In various embodiments, at least a portion of the consolidated information may be provided directly or indirectly from the consolidation component 264. In embodiments, the patient specific preview can provide alerts, notifications, registry identification, program enrollment, model predictions, and time sensitive events of interest for a patient. For example, in such embodiments, the preview may indicate that a patient was recently enrolled in a diabetes registry, provided an alert that the patient was admitted to skilled nursing without an appropriate diet order, that the patient has not received a flu shot, and that the patient has missed the last two appointments with an orthopedic surgeon. In various embodiments, one or more of the alerts, notifications, or other information may expire after a given time period so as to not crowd the situational view with untimely information. For example, in embodiments, a notification that the patient has not taken a flu shot will only be shown shortly before and during a flu season and will not be shown after the flu season. In another embodiment, information may be available for viewing over time and may not be eliminated from view once the first healthcare provider has seen the information.

In certain embodiments, the situational component 268 may indicate an event or situation has occurred, or may occur, and this information may sequentially reveal the time of events. In the same or alternative embodiments, the situational component 268 may allow for flagging of particular events of interest for communication with additional providers. An exemplary situational view, which, in embodiments, may be at least partially created by the situational component 268, is depicted in FIG. 17.

In embodiments, the natural language processing component 270 can extract information, e.g., clinical indicators, from at least a portion of one or more patient's health records, such as the health records associated with one or more EMRs 212. In such embodiments, the natural language processing component 270 can extract information from clinical data, which may include clinical impressions and/or clinical narratives from one or more healthcare providers. In embodiments, the clinical impressions and/or clinical narratives may be associated with one or more of: a patient's condition, a course of treatment for a patient, a plan of treatment for a patient, diagnostic tests, specialty studies, pathology reports, and operative reports. The natural language processing component 270 can utilize any natural language processing technology known to one skilled in the art, as long as such technology is capable of extracting information from clinical impressions and/or clinical narratives.

In certain embodiments, the natural language processing component 270 may extract, from healthcare data, one or more clinical indicators that may be associated with one or more chronic conditions. In such embodiments, the chronic conditions may include heart failure, acute kidney injury, chronic kidney disease, malnutrition, COPD, asthma, musculoskeletal diseases, cancer, acute infections, HIV, and/or autoimmune diseases. In various embodiments, by having extracted data, e.g., clinical indicators related to one or more chronic conditions, the population health server 250, e.g. via the stratifying component 256, may be able to stratify one or more patients into one or more clinical stages or classes of a chronic disease.

In certain embodiments, the natural language processing component 270 may qualify clinical assessments. This is because a clinical assessment from one healthcare provider may be more relevant than a clinical assessment from another healthcare provider. For example, a clinical assessment relating to heart failure can be weighted more when coming from a cardiologist compared to a heart failure assessment from an emergency room physician. In this regard, the natural language processing component 270 may parse subjective or judgment terms to non-discrete information such as clinical documentation or dictation (e.g., impression, course, plan, etc.) as well as interpretation of test results or diagnostics (e.g., x-ray, echocardiogram, electrocardiogram, pathology reports, stress test, pulmonary functions, operative reports, and the like). Accordingly, in embodiments, the natural language processing component 270 may provide a relevance rating to one or more clinical indicators extracted from the healthcare data. In such embodiments, the relevance rating may be based on the expertise of a healthcare provider that is associated with each of the extracted clinical indicators. These relevance ratings may be applied to such extracted information in order to better inform the appropriate healthcare provider when viewing such information. In certain embodiments, a clinical assessment from a physician that does not specialize in that particular field to which the assessment relates may be flagged as needing a second opinion or as needing validation by a particular specialist.

Generally, the antibiogram component 272 provides a flexible report that provides susceptibility rates based on selected populations. The cross venue or population based antibiogram allows providers to view susceptibility trends based on institution, physician practice, zip code, city, state, region, or country. Current antibiograms focus solely on inpatients or outpatients and do not take into account additional factors amongst patients that can impact the effectiveness of the more commonly prescribed antimicrobials. Prescribing an ineffective antimicrobial based on the overall population can lead to significant delays in the patient's recovery. Allowing the provider to see which antimicrobials will be most effective based on the patients circumstances and region allows for better prescribing practices. Currently, antibiograms are only available for a subset of patients and are limited in their ability to display results based on patient populations outside of the hospital.

The cross venue antibiogram is based on a data set that includes susceptibility results from testing performed on inpatients, outpatients, and results from patients within the community, outside of the hospital setting. This data set contains basic patient demographics, but does not include patient identifiers. Antibiogram reporting is available using this data set allowing the provider to filter the results returned by various demographic parameters. As described herein, these parameters may include, but not be limited to institution, physician practice, zip code, city, state, region, or country. Collectively, the information provided by the cross venue antibiogram allows the prescriber to more accurately prescribe medications, provides a broader view of susceptibility result trends overall, improve infectious disease outcomes, is powerful for use across venues and agencies, and includes public health implications.

In embodiments, antibiogram component 272 receives medications information from disparate data sources. The data sources may include multiple venues, multiple providers, or across multiple conditions. For example, medications information may be received from one or more EMRs 212, each of which may be independent from one another. As described herein, the EMRs 212 may span multiple applications, multiple providers, multiple patients, multiple conditions, multiple venues, multiple facilities, multiple organizations, and/or multiple communities.

Susceptibility results may be received based on testing associated with patient information provided by the disparate sources. The susceptibility results may also be received from the one or more EMRs 212. The susceptibility results may indicate, at a population level, culture results for bacteria, fungus, viruses, and the like, that are found in a particular population. In this regard, drug resistance, drug effectiveness, and drug utilization may be received.

A cross venue antibiogram may be created based on the medications information and the susceptibility results. The cross venue antibiogram enables the population health server 250 to create an antibiogram that is not restricted to a single institution or by stale data. Rather the cross venue antibiogram may be created in real-time based on the information received by various components of the population health server 250. This allows both a clinician and the population to see how to manage or identify increased resistant patterns, switch pharmacies (i.e., if one particular pharmacy is supplying an ineffective medication that is otherwise not identified in the increased resistant patterns), and the like.

The antibiogram may account for bacteria, fungus, viruses, and the like that are found in a particular community as well as the medications (e.g., antibiotics, antihypertensives, anticoagulants) that are most effective, those that are not effective, and susceptibility. The antibiogram may be stored in one or more antibiograms databases 235 and may be accessible via the network 210. The antibiogram includes antibiogram data relevant to a population of patients. The antibiogram databases 235 may be a networked storage or distributed storage including storage on servers located in the cloud. Thus, it is contemplated that for some embodiments, the information stored in the antibiogram databases 235 is not stored in the same physical location. The information within the antibiogram databases 235 may exist in a variety of standardized formats including, for example, narratives and other data. Information in the antibiogram databases 235 may be categorized or classified according to, for example, claims, diagnoses, wellness, satisfaction, population directories, and the like.

Each antibiogram may be used by, for example, a healthcare organization to manage or identify resistant patterns for a population segment. Each antibiogram may be condition specific. By way of example, a healthcare organization or clinician may manage diabetic patients within a proscribed geographic area. The condition in this case is diabetes mellitus and the antibiogram databases 235 may help the healthcare organization manage a population segment with this condition differently for a particular resistant pattern than another population.

In embodiments, filtering of the antibiogram enables reporting based on selected demographics. The selected demographics may include an institution, a practice associated with a clinician, a zip code, a county, a city, a state, a region, or a country. The selected demographics may further include a diagnosis, condition, or state associated with the patient. Selections can be made by a clinician, such as from device 240 (e.g., a clinician device). Upon making these selections, a filtered antibiogram may be presented on the device 240 in accordance with the selections. For example, a clinician may be treating a diabetes patient with a particular bacterial infection. The clinician may select demographics associated with the diagnosis, condition, location, and the like to enable the clinician to prescribe the most effective treatment based on the selections.

Generally, the medication advisor component 274 provides a prescriber focused tool that provides dosing, cost, susceptibility, and availability information for the prescriber to consider prior to placing a medication order. The comprehensive medication advisor is a prescriber order entry tool that provides more information face up to the prescriber that is important to evaluate before the medication order is entered. The advisor may be functional in all healthcare settings and may contain dosing recommendations for common disease states including but not limited to infectious diseases, coagulopathy, hypertension, and hyperlipidemia.

Current prescriber order entry tools are a valuable way to prevent medication errors and influence drug choice. However, the current tools lack the ability to provide a complete picture of additional factors such as cost and availability and, for antimicrobials, susceptibility data. By including cost, availability, and susceptibility data, the comprehensive medication advisor disclosed herein enables clinicians to prescribe the most appropriate medication for their patient.

The comprehensive medication advisor described herein provides information to clinicians when they are prescribing medication that may expedite the prescribing process and prevent prescribing errors. Providing cost, availability, and susceptibility information during the order entry process may expedite prescriber workflow, improve outcomes, prevent medication errors, and reduce drug expenditures.

When a prescriber opens the advisor for a specific disease state, the advisor may contain multiple appropriate medication options. The cost, availability, and susceptibility information (when appropriate) may also be available for the prescriber to view prior to prescribing a medication. Cost may be shown in the most appropriate format, including but not limited to relative cost, actual wholesale price, institution cost, or patient cost. Availability may be displayed using numerical amount or relative amount of drug in stock. Susceptibility data may be provided for antimicrobials by incorporating the most appropriate antibiogram data, such as may be provided by antibiogram component 272. As such, the susceptibility data may include information relevant to one or more of the individual patient, institution, physician practice, zip code, city, state, region, or country.

Information provided by the comprehensive medication advisor may expedite prescriber workflow by providing the clinician with the information necessary to accurately prescribe medications, preserve stock when drug shortages occur, reduce drug expenditures, improve infectious disease outcomes, and/or enable evidence based decision support for prescribing providers.

In embodiments, medication advisor component 274 receives a specific disease state for a patient. The specific disease state may be communicated by a clinician via a device 240, such as a clinician device. The specific disease state may be received automatically via an EMR 212. The disease state may be utilized to further filter the antibiogram, as described above, to help a clinician identify an antibiogram specific to the disease state associated with a particular patient.

In embodiments, related conditions, laboratory results, and allergy information for the patient are received, via one or more data sources (e.g., the EMR 212), by the medication advisor component 274. Each of the related conditions, laboratory results, and allergy information may further influence how the clinician filters the antibiogram to provide a patient-centric antibiogram. In an embodiment, each of the related conditions, laboratory results, and allergy information may be provided to the antibiogram component 272 automatically, via one or more data sources (e.g., the EMR 212), to create the patient-centric antibiogram that is displayed on the clinician device. Further information may include genomic information and may be similarly provided to the antibiogram component 272.

In embodiments, multiple medication options are provided for the patient. The medication options may include generic alternatives, cost, availability, and susceptibility information. In embodiments, the generic alternatives for a particular medication are provided to the clinician device. In embodiments, the cost for a medication or each of the generic alternatives is provided to the clinician device 240. The cost may include relative cost, actual wholesale price, institution cost, patient cost, or cost effectiveness. Cost effectiveness may factor in susceptibility information. In embodiments, availability of a medication is provided to the clinician device 240. The availability may include a numerical amount or relative amount of a drug in stock.

In embodiments, susceptibility information is provided to the clinician device. The susceptibility information is based on the antibiogram and may include information relevant to one or more of the patient, an institution, a practice associated with a clinician, a zip code, a county, a city, a state, a region, or a country. Each of these items of information provided to clinician device allows the clinician to identify, without influence (e.g., drug rep, etc.), the proper formulary of drug included within the ordering framework and provide the patient information that may help the clinician and patient select the most appropriate medication.

Generally, medication stewardship component 276 provides an ability to assess for inappropriate drug utilization as well as trends within a population of people at multiple levels. For example, an assessment can be made within a physician practice, an outpatient facility, a long term care facility, a community, a city, a state, and/or a country. In an embodiment, the medication stewardship component 276 is utilized to assess antibiotic use in an inpatient setting. In this regard, direct feedback may be provided to prescribers if a particular use is deemed inappropriate. The assessment may consider, in embodiments, susceptibility information is based on the antibiogram and may include information relevant to one or more of the patient, an institution, a practice associated with a clinician, a zip code, a county, a city, a state, a region, or a country. Additionally or alternatively, the assessment may consider specific clinical data relevant to a particular patient. This feedback may be utilized to reduce medication misuse, errors, and healthcare costs, while improving outcomes.

For example, in acute care settings, prescribing and patient monitoring oversight is frequently provided by a secondary healthcare provider such as a pharmacist or nurse. Prescribing guidance may also be provided via restricted formularies and prescribing guidelines. However, similar oversight in non-acute care settings is not possible because current healthcare systems are not able to account for patients in non-acute care settings taking multiple medications prescribed by different physicians and/or filled at separate pharmacies. Medication stewardship component 276 monitors each of these variables and provides feedback at the individual patient-level, as well as for entire populations of people for evaluation of medication misuse events as well as trends. In this regard, medication stewardship component 276 reduces medication misuse, medication errors, and healthcare costs.

In embodiments, trends of inappropriate medication use may be evaluated or monitored by medication stewardship component 276. Additionally, emerging trends in treatment failure or ineffectiveness (e.g., antimicrobial resistance) may quickly be identified by utilizing information received from other components of the population health server 250 (e.g., antibiogram component 272, medication advisor component 274, and the like). Patient adherence or lack thereof may also be monitored by medication stewardship component 276. Drug-drug interactions may be detected by medication stewardship component 276 for patients who use multiple pharmacies. Medication stewardship component 276 may assess if patients are being properly monitored and educated and may predict patient or clinician non-compliance as well as the need for additional education. Provider prescribing trends and effects of intervention may also be monitored by medication stewardship component 276.

In embodiments, medication stewardship component 276 monitors and flags inappropriate trends and may alert or notify medication stewards to intervene. In embodiments, medication stewardship component 276 flags and alerts medication stewards to intervene for development of antimicrobial resistance, unnecessary prescriptions, incorrect or more costly medications, neglecting to order follow up laboratories to monitor for adverse drug reactions, patients not refilling medications as prescribed, and/or drug interactions from patients using multiple pharmacies and/or providers.

In an embodiment, medication stewardship component 276 documents interventions via an automated messaging system. In another embodiment, interventions may be documented manually, such as via a device 240, and stored by the medication stewardship component 276. Outcomes of the interventions may be similarly documented or stored by medication stewardship component 276. In this regard, both trending and reporting is enabled by medication stewardship component 276. In addition to antimicrobials, medication stewardship component 276 may additionally monitor and improve utilization for antihypertensives, antihyperlipidemics, analgesics, and anticoagulants.

The management component 278 may provide information associated with managing a population of patients for a particular health system. In one or more embodiments, the management component 278 may utilize data from one or more EMRs 212, activity data 214, demographics 216, and/or care provider information 220 to consolidate, process, and analyze information, and alert a manager or healthcare provider to metrics that are not within a predetermined range. In addition, in such embodiments, the management component 278 may provide an overview of the health system and the population of patients associated therewith.

Figure 14:
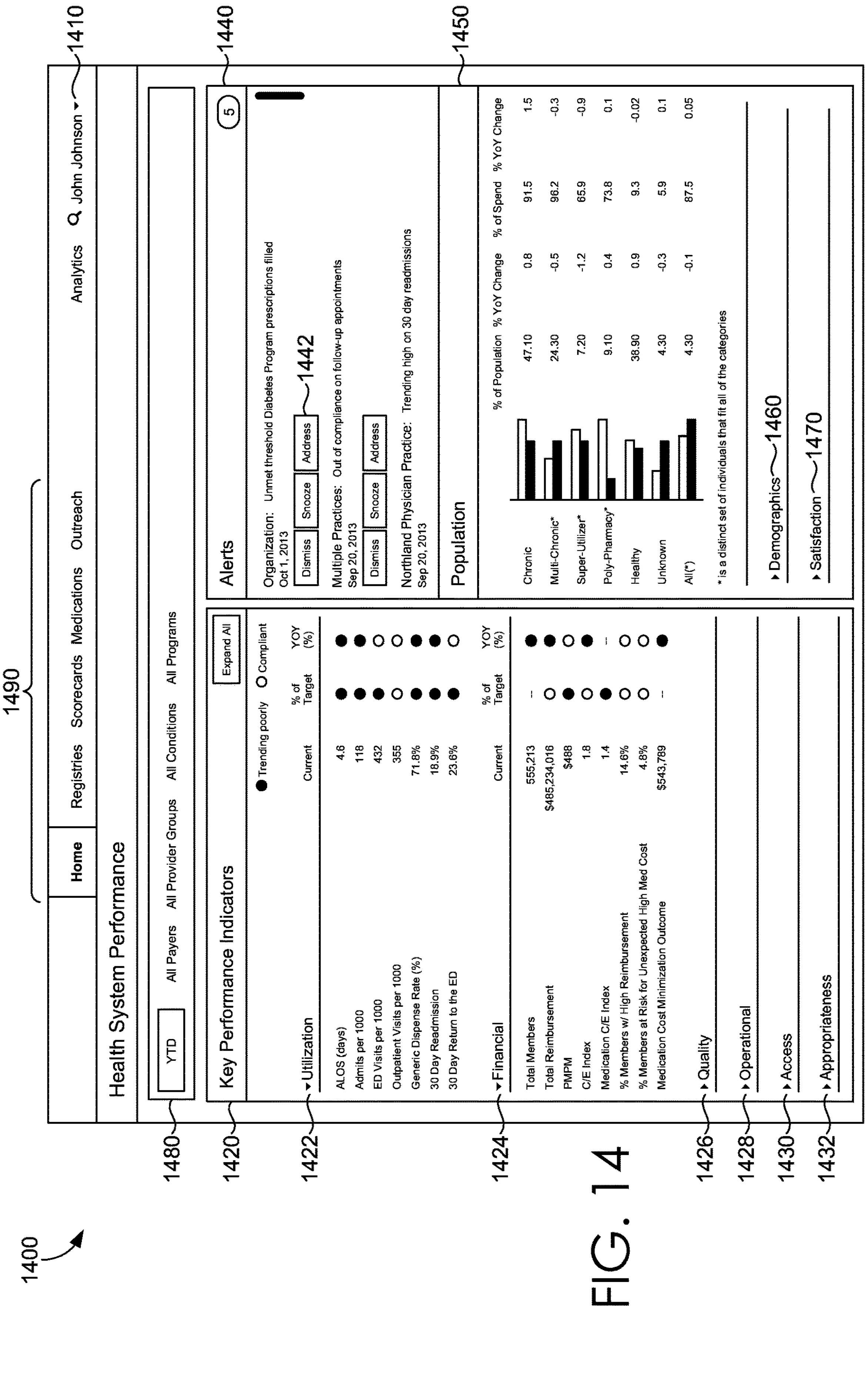
Figure 15:
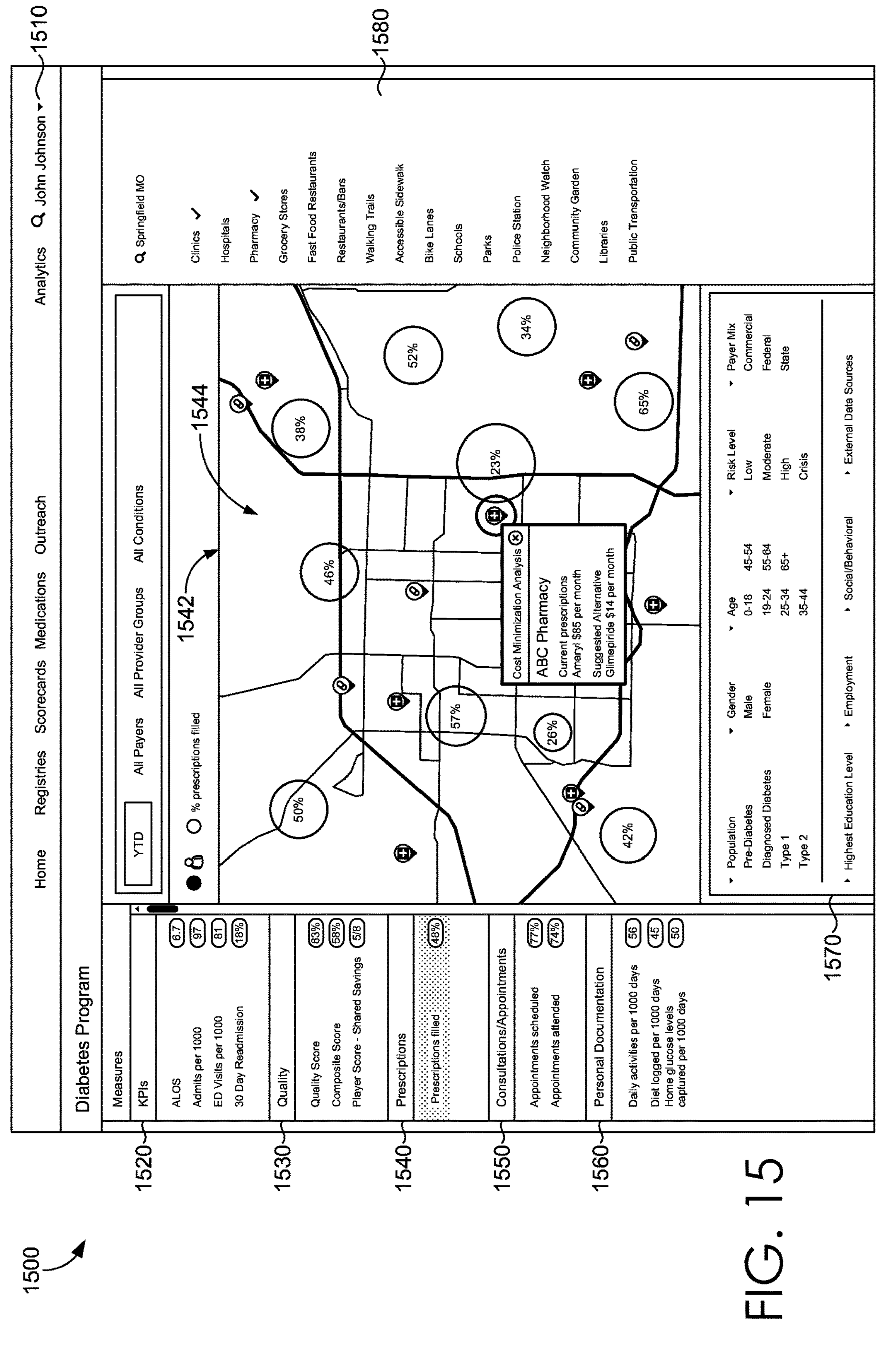

In certain embodiments, the management component 278 may provide information on the health system and/or on at least a portion of a population of patients within the health system. For example, in such embodiments, this information may include one or more metrics to assess utilization of the facilities and/or services associated with the health system. Further, in embodiments, this information may include any type of financial information associated with the health system. In one or more embodiments, the information may include an overview of various care programs operated by the health system. In certain embodiments, the information may include general population health metrics for the patients associated with the health system, such as the percentage of patients having chronic conditions, rate of readmissions, etc. In one or more embodiments, the information may include alerts to notify a manager or healthcare provider of issues to be addressed, such as low compliance with follow-up appointments, with getting prescriptions filled, etc. The information provided by the management component 278 may be presented in any fashion. Exemplary health system overviews that may be at least partly provided by the management component 278 are depicted in FIGS. 14 and 15.

In certain embodiments, the management component 278 may provide a proposed plan to help allocate health system and/or healthcare resources available for a population of patients. For example, in such embodiments, the management component 278 may find care provider resources, e.g., from the care provider information 220, that are available for a population of patients having a particular condition of interest. This may allow a healthcare provider and/or manager to better allocate resources as necessary to accommodate the population of patients of interest. In one embodiment, the management component 278 may utilize information associated with at least one output registry, such as an output registry stored in the output registries database 230, to provide a proposed plan to allocate health system and/or healthcare resources available for at least a portion of a population of patients.

In certain embodiments, the healthcare transition component 280 can facilitate transition care for one or more patients. For example, in one or more embodiments, the healthcare transition component 280 may utilize data from one or more EMRs 212, demographics 216, and/or care provider information 220 to facilitate the arrangement of transition care. In such embodiments, the healthcare transition component 280 may provide transition care information to a healthcare provider so that the healthcare provider can review the transition care arrangements with the patient during an appointment with the healthcare provider.

The healthcare transition component 280 can facilitate any type of transition care required for a patient. For example, in embodiments, the healthcare transition component 280 can schedule an appointment for a patient and/or arrange transportation services for the patient. In one embodiment, the healthcare transition component 280 can arrange for the delivery of prescriptions and/or arrange for prescription assistance. In various other embodiments, the healthcare transition component 280 may arrange follow-up services that may be needed for a patient, such as support groups, dietary requirements, etc., and provide information for a healthcare provider to educate the patient about such services. In certain embodiments, the healthcare transition component 280 may determine and notify a healthcare provider if a referral need exists for a certain patient. Further, in one or more embodiments, the healthcare transition component 280 can facilitate the assignment of a particular healthcare provider to a particular patient. Exemplary transition care processes, which, in embodiments, may be at least partially performed by the healthcare transition component 280, are described below with reference to FIGS. 5-8 and 11-13.

In embodiments, the condition module 282 may be specific to one medical condition and one patient and provide associated information across multiple venues. In such embodiments, the condition module 282 can provide a patient- and condition-specific overview to allow healthcare providers to monitor specific issues and see the story of the patient's condition. In embodiments, the story conveyed by the condition component 282 can include a longitudinal timeline of events related to that condition, such as the time of diagnosis, treatments, labs and diagnostics related to condition, and quality measures. In certain embodiments, the condition component 282 may account for venue and may display time relative information for more acutely collected data (i.e. for the hospitalized patient or acutely monitored patient).

In one or more embodiments, the condition component 282 may provide visibility to care teams involved, consultations, references, and/or quality measures as they relate to the condition of interest. In certain embodiments, the condition component 282 may provide a healthcare provider access to disparate EMR' s for more detailed information associated with the condition of interest while providing access to clinical decision support tools (such as care process maps, treatment nomograms, etc.) for the condition of interest. In embodiments, the condition component 282 can provide similar information across venues and healthcare providers so that all healthcare providers will be accessing similar condition information. In certain embodiments, the condition component 282 may include specialist specific views or information, which can account for more complex care issues. The ability to correlate and connect condition specific information from various systems for cross-continuum display may lessen the burden of potential errors, educate the community of providers responsible for this patient, and improve accuracy and efficiency for population management.

In certain embodiments, the condition component 282 can include a condition timeline or longitudinal record. In such embodiments, this longitudinal record can provide a timeline of events related to the particular condition of interest. The timeline of events may include laboratory results, medications, diagnostics, and/or interventions derived from the healthcare data from multiple venues, multiple providers, and across multiple conditions. In embodiments, the timeline can enable clinicians to quickly identify additional information about a patient with a particular condition of interest, even while reviewing data originating from multiple data sources, multiple venues, or multiple providers and even from multiple conditions.

In embodiments, the timeline may provide the clinician a longitudinal story for a patient with a particular diagnosis or condition. For example, a clinician may have a diabetic patient. The timeline of events may provide the clinician events related to diabetes over the last six months that have occurred. The clinician may initially see normal blood sugar and then identify, two weeks later, that the blood sugar was elevated. At this point, the clinician may identify that all other laboratory results were also high or off or find where the patient received an intervention with a specialist. Exemplary condition component information, which, in embodiments, may be at least partially provided by the condition component 282, are described below with reference to FIGS. 18, 21, and 22.

In embodiments, the patient portal component 284 can provide healthcare-related information for a particular patient. In certain embodiments, the patient portal component 284 can allow the patient to view their healthcare data and the outputs of any program algorithms, such as an identification algorithm and/or a stratification algorithm. In one or more embodiments, the patient portal component 284 can provide access to educational information and workshops relevant to the patient's health status or conditions. In certain embodiments, the patient portal component 284 can allow the patient to input information into their healthcare record, such as exercise, diet, personal device data, payment information, etc. An exemplary patient portal, which, in embodiments, may be at least partially provided by the patient portal component 284, is described below with reference to FIG. 27.

In certain embodiments, the baseline component 286 can consolidate basic information about a population, provider, or patient, and direct the identification and stratification of appropriate parameters to facilitate basic care operations. In one or more embodiments, the baseline component 286 can consolidate information associated with identified and/or stratified subsets of a patient population and can provide care planning, improve care transitions, optimize resource utilization; and/or contain costs. For example, in one embodiment, knowing that a patient is likely highly motivated for healthcare purposes and has a high compliance rate, the baseline component 286 can notify a healthcare provider and/or health system that they can rely on the patient to comply with their care and need not spend resources unnecessarily. In certain embodiments, the baseline component 286 can provide a holistic view of a population, provider and/or a patient and can address and/or predict underlying gaps in care, notify appropriate providers, patients, and family, and proactively manage these situations prior to penalties or crises.

The population health management system 200 is an open-loop system meaning that as a healthcare organization utilizes the output of the population health server 250, more organizational and patient data is generated which is fed back into the system 200 and used to update the various output registries 230, EMRs 212, and/or antibiograms 235. Further, the system 200 operates over and is compatible with existing electronic medical record systems associated with healthcare organizations, even if these electronic medical record systems are disparate in nature. Thus, a healthcare organization can utilize the system to manage population health without having to incur significant financial costs to reconfigure its already-existing electronic medical record system.

Figure 3:
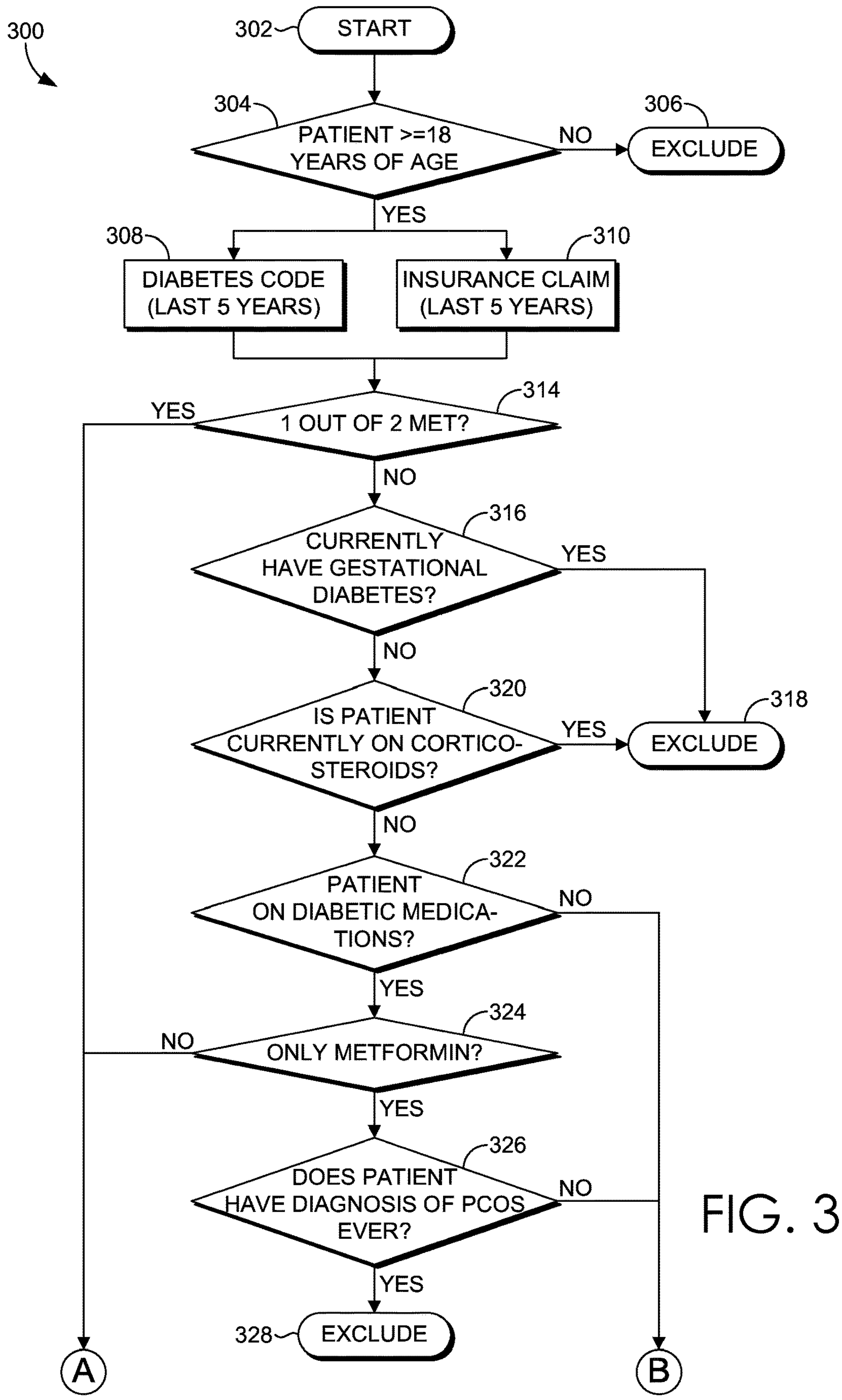
FIG. 3 is a flow diagram illustrating exemplary methods of utilizing an identification algorithm for registry population, in accordance with embodiments of the present invention.
Figure 3:
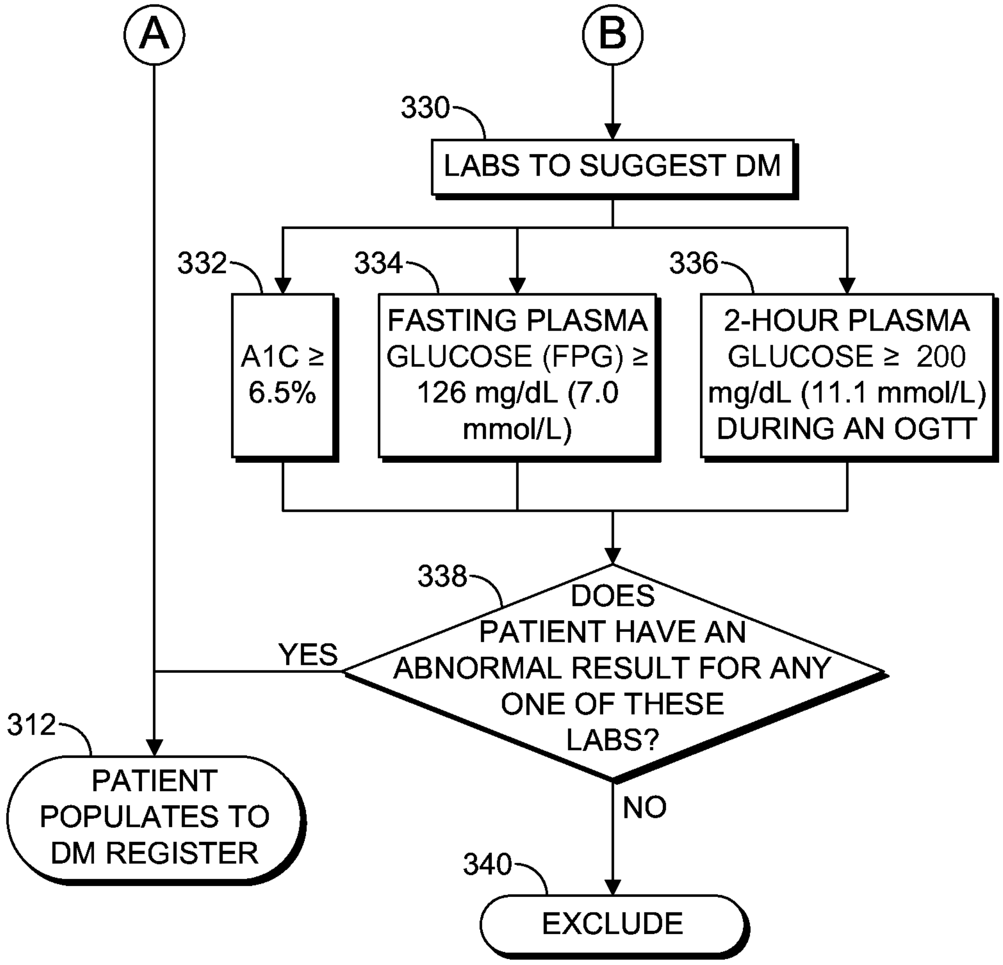

Turning now to FIG. 3, an exemplary identification algorithm 300 is depicted for identifying patients that have or may have diabetes. It should be understood that the specific steps and the order of the steps depicted in the algorithm 300 are only exemplary and that other steps and different orders of the steps may be user. In addition, it should be understood that other possible variations for the algorithm 300 are within the scope of the present invention.

In the embodiment depicted in FIG. 3, the identification algorithm 300 may include a start step 302, where data associated with one or more patients is received, and then at the step 304 the data is queried to determine if the patient is greater than or equal to 18 years old. If the patient is not greater than or equal to 18 years old, at step 306, the patient is excluded from the being populated in a diabetes registry. After a patient is determined to be greater than 18 years old the patient information is queried to determined, at steps 308 if there is a diabetes code, and at step 310, if there is an insurance claims present in the patient information. At step 314, if the one out the two criteria in steps 308 and 310 are present then at step 312, the patient is populated into a diabetes mellitus registry. In none of the two criteria in steps 308 and 310 are met, at step 316, it is determined if the patient currently has gestational diabetes. If so, then at step 318, that patient is excluded from being populated in the diabetes registry. If the patient does not currently have gestational diabetes, then at step 320, it is determined if the patient is currently on corticosteroids. If so, then, at step 318, the patient is excluded.

If the patient does not currently on corticosteroids then, at step 322, it is determined if the patient is on diabetic medications. If so, then it is determined, at step 324, if the patient is only on metformin, and if not, then the patient is populated in the diabetes mellitus registry. If the patient is not only on metformin, then at step 326, it is determined if the patient have ever been diagnosed with polycystic ovarian syndrome (PCOS). If so, then at step 328, the patient is excluded from being populated in the diabetes registry.

For a patient that is not on diabetic medications and has not been ever diagnosed with having PCOS, then, at step 330, it is determined if the patient has any clinical laboratory data to suggest that the patient has diabetes. For instance, at step 332 the patient information is queried to determine if there is laboratory data evidencing a A1C value greater than or equal to 6.5%. Further, at step 334, the patient information is queried to determine if there is laboratory data evidencing if the fasting plasma glucose concentration is greater than or equal to 126 mg/dL (7.0 mmol/L). In addition, at step 336, the patient information is queried to determine if there is laboratory data evidencing a 2-hour plasma glucose concentration of greater than or equal to 200 mg/dL (11.1 mmol/L) during an oral glucose tolerance test (OGTT). At step 338, it is determined if the patient has an abnormal result for any of the tests queried for in steps 332, 334, and 336. If so, then the patient populates to the diabetes registry at step 312. If not, at step 340, the patient is excluded from population in the diabetes registry.

Figure 4:
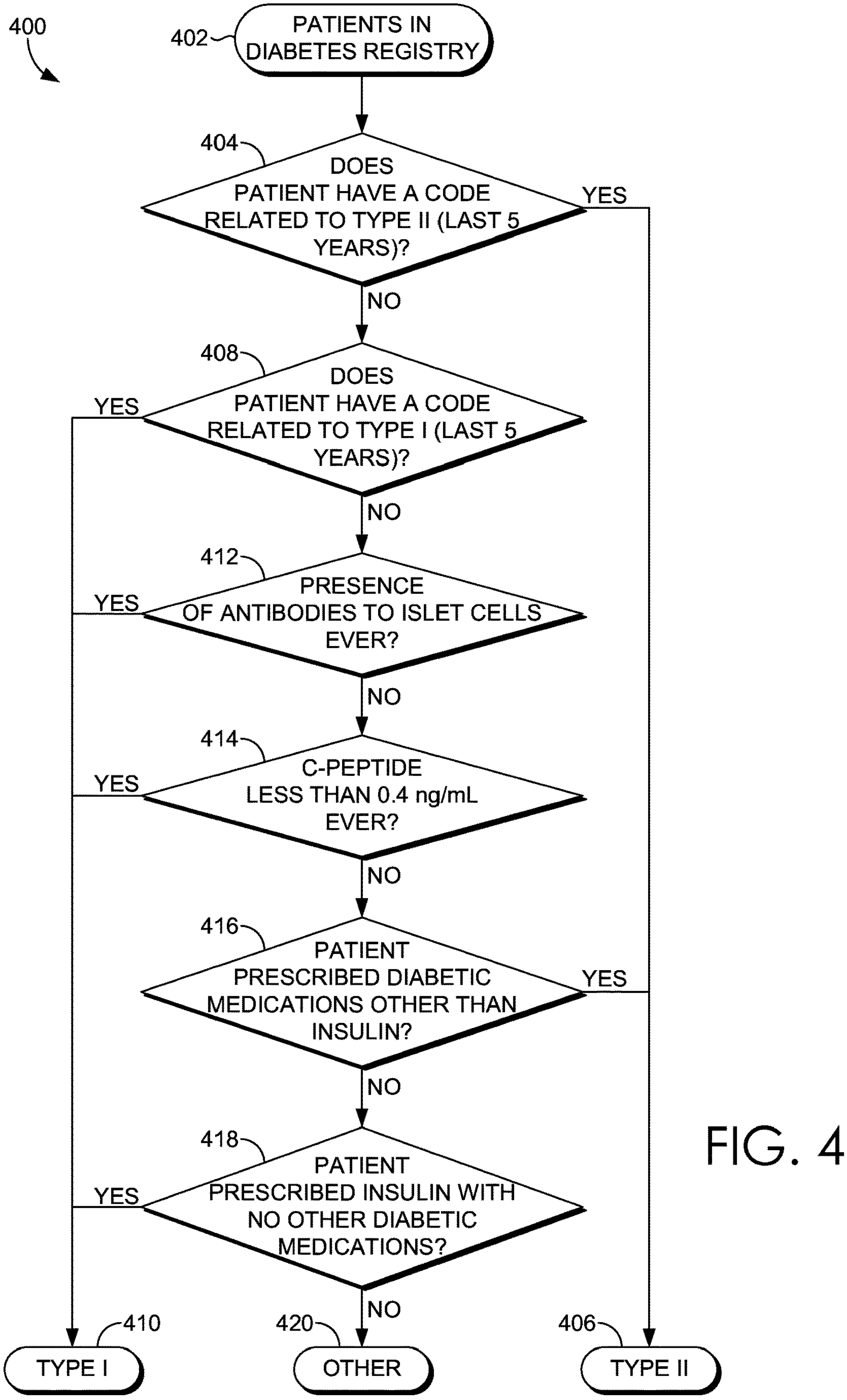
FIG. 4 is a flow diagram illustrating exemplary methods of utilizing a stratification algorithm for stratification one or more patients in a registry, in accordance with embodiments of the present invention.

FIG. 4 depicts an exemplary stratification algorithm 400 is depicted for stratifying one or more patients present in a diabetes registry. It should be understood that the specific steps and the order of the steps depicted in the algorithm 400 are only exemplary and that other steps and different orders of the steps may be user. In addition, it should be understood that there other possible variations for the algorithm 400 within the scope of the present invention.

At step 402, patient information associated with patients present in the diabetes registry is received. In certain embodiments, at the step 304, the information related to one or more patients in the diabetes registry is queried to determine if the patient information includes a code related to Type II diabetes within the last five years. If so, then at step 406, the patient is stratified to be associated with Type II diabetes. If the patient information does not include a code related to Type II diabetes within the last five years, at step 408, it is determined if the patient information includes a code related to Type I diabetes within the last five years. If so, then, at step 410, the patient is stratified to be associated with Type I diabetes. If the patient does not include a code related to Type I diabetes within the last five years, at step 412, it is determined if the patient information includes clinical data suggesting the presence of antibodies to islet cells. If so, then, at step 410, the patient is stratified to be associated with Type I diabetes. If the patient information does not include clinical data suggesting the presence of antibodies to islet cells, then at step 414, it is determined if the patient information includes clinical data that suggesting a C-peptide concentration of less than 0.4 ng/mL. If so, then, at step 410, the patient is stratified to be associated with Type I diabetes. If the patient information does not include clinical data that suggesting a C-peptide concentration of less than 0.4 ng/mL, then at step 416, it is determined if the patient has been prescribed diabetic medications other than insulin. If so, then at step 406, the patient is stratified to be associated with Type II diabetes. If the patient has not been prescribed diabetic medications other than insulin, then at step 418, it is determined if the patient has been prescribed insulin and no other diabetic medications. If so, then at step 410, the patient is stratified to be associated with Type I diabetes. If not, then the patient is placed in the "other category" which is does not include patients stratified to be associated with Type I or Type II diabetes.

Figure 5:
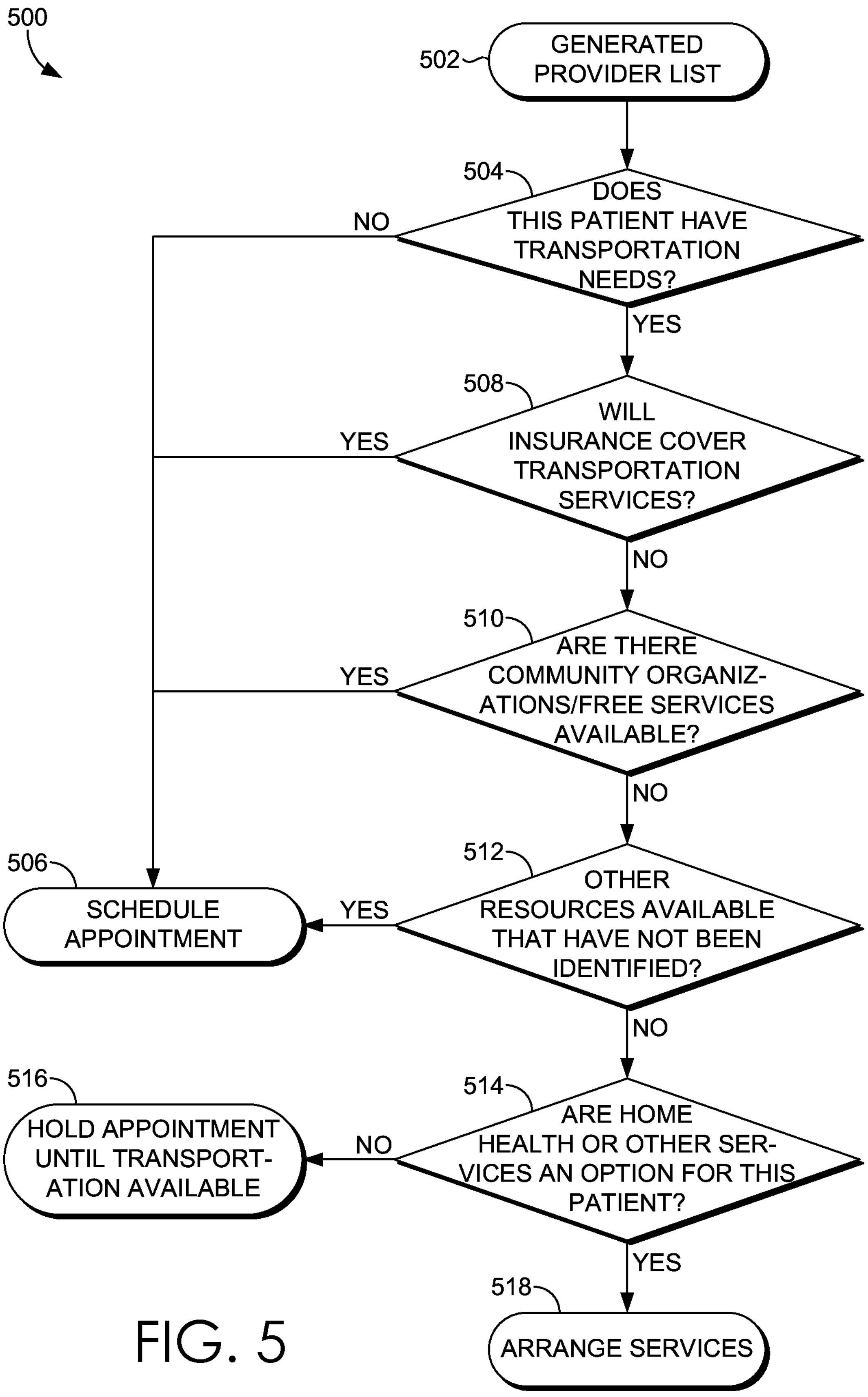
FIG. 5 is a flow diagram illustrating exemplary methods for utilizing an algorithm to provide transition management care, in accordance with embodiments of the present invention.

As discussed above, in certain embodiments, a population health management system, e.g., the population health management system 200 of FIG. 2, can aid in providing transition healthcare for one or more patients. For example, in certain embodiments, a population health server may provide transition management care associated with transportation of a patient to or from a healthcare venue for an appointment. FIG. 5 depicts one embodiment of an algorithm 500 that may be used to determine a need for transportation for an appointment and if, based on the transportation situation of patient if an appointment should be scheduled. It should be understood that the specific steps and the order of the steps depicted in the algorithm 500 are only exemplary and that other steps and different orders of the steps may be user. In addition, it should be understood that there other possible variations for the algorithm 500 within the scope of the present invention.

At step 502, a population health management system receives and/or generates a generated provider list that may include one or more patients in need of scheduling an appointment to see a healthcare provider and may or may not have transportation needs. At step 504, it is determined if the patient has transportation needs, and if not, then at step 506 an appointment is scheduled for the patient. If the patient does transportation needs, then at step 508, it is determined if the patient's insurance will cover transportation services for healthcare provider appointments. If so, then at step 506, an appointment is scheduled. If the patient's insurance will not cover transportation services then, at step 510, it is determined if there are community organizations or free services that can provide transportation. If so, then at step 506, an appointment is scheduled. If there are no community organizations or free services that can provide transportation, then at step 512, it is determined if there are other resources available that have not been identified. If so, then at step 506, an appointment is scheduled. If there are no other resources available, then at step 514 it is determined if there are home health or other service options for this patient. If so, then the home health or other services are arranged at step 518. If there is no home health or other service options available for the patient, then at step 516, the patients an appointment is put on hold until transportation services become available.

Figure 6:
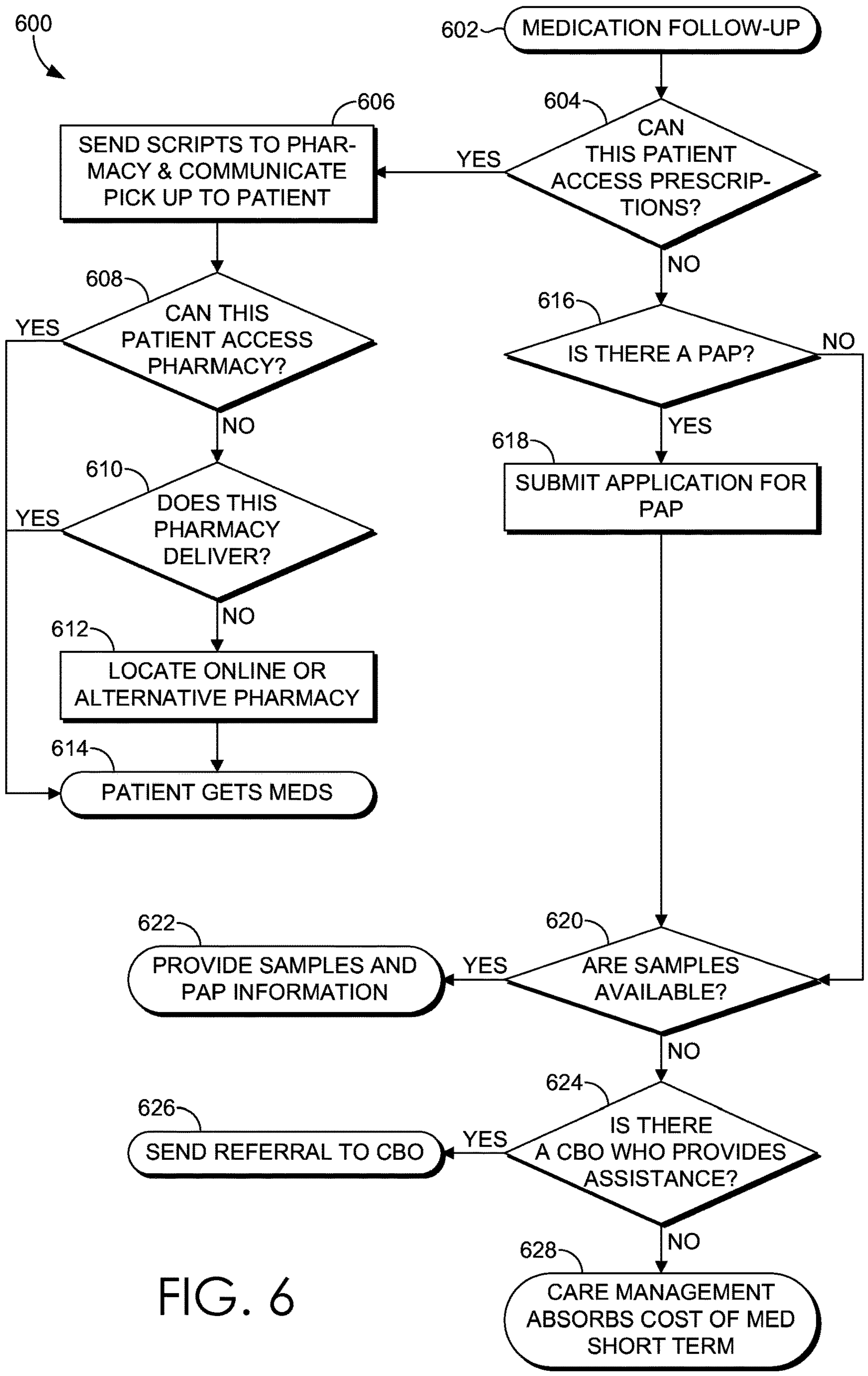
FIG. 6 is a flow diagram illustrating exemplary methods for utilizing an algorithm to provide transition management care, in accordance with embodiments of the present invention.

FIG. 6 depicts another embodiment of an algorithm 600 that may be utilized to provide transition care by facilitating the provision of medications to a patient. It should be understood that the specific steps and the order of the steps depicted in the algorithm 600 are only exemplary and that other steps and different orders of the steps may be user. In addition, it should be understood that there other possible variations for the algorithm 600 within the scope of the present invention.

At step 602, a population health management system, e.g., the population health management system 200 of FIG. 2, can determine that medication follow-up is needed for a patient. At step 604, it is determined if the patient can access prescriptions, and if so, then at step 606, a prescription is sent to a pharmacy and communication with the patient is initiated in order to arrange the pick-up of the medication. At step 608, it is determined if the patient can access the pharmacy for medication pick up, and if so, then at step 614, the patient receives the medication. If the patient cannot access the pharmacy, then at step 610, it is determined if the pharmacy can deliver the medication. If so, then at step 614, the patient receives the medication via delivery by the pharmacy. If the pharmacy does not deliver and the patient cannot access the pharmacy, then at step 612 an online pharmacy or a suitable alternative pharmacy is located, where at step 614, the patient will receive the medication.

If it is determined in step 604 that the patient cannot access the prescriptions, then at step 616, it is determined if there is a prescription assistance program (PAP) to help, and if so, at step 618 an application is submitted for the PAP. If a PAP is available to help and an application has been submitted at step 618, and/or if a PAP is not available to help, at step 620 it is determined if there are medication samples available. If there are samples available, then at step 622, samples are provided or arranged to be provided and PAP information is provided or arranged to be provided. If there are no samples to be provided, then at step 624 it is determined if there is a central billing office (CBO) that can provide medication assistance, and if so, at step 626, a referral is sent to the CBO. If there is not a CBO to provide assistance, then at step 628, the care management may absorb the cost of medications in the short term.

Figure 7:
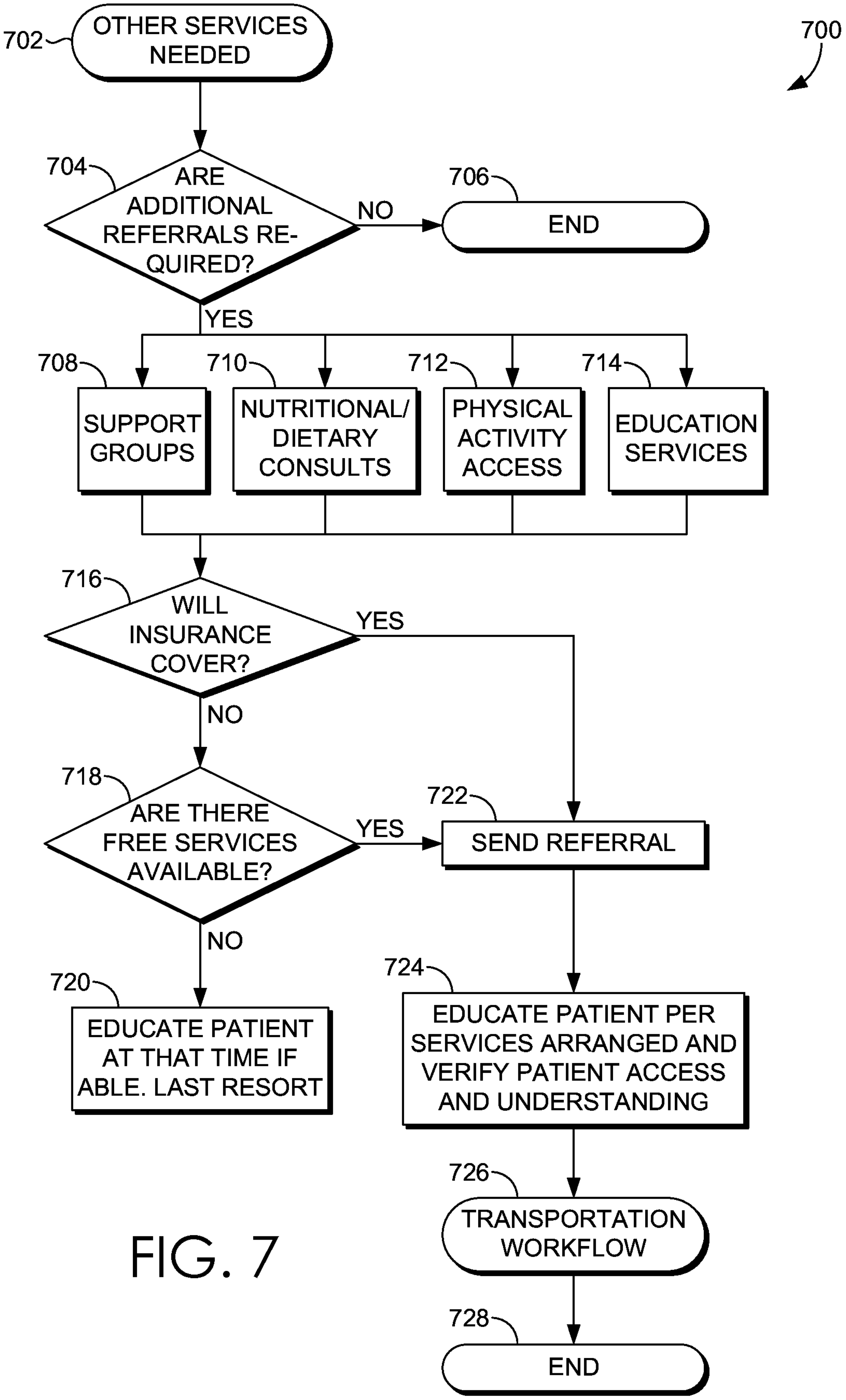
FIG. 7 is a flow diagram illustrating exemplary methods for utilizing an algorithm to provide transition management care, in accordance with embodiments of the present invention.

FIG. 7 depicts another embodiment of an algorithm 700 that may be utilized to provide transition care by facilitating the provision of additional services for a patient. It should be understood that the specific steps and the order of the steps depicted in the algorithm 700 are only exemplary and that other steps and different orders of the steps may be user. In addition, it should be understood that there other possible variations for the algorithm 700 within the scope of the present invention.

At step 702, it is determined that other services, such as follow up support, education, etc., may be necessary for the patient. At step 704, it is determined if additional referrals are required for the additional services, and if not, at step 706 the process stops. If additional referrals are required, it is determined if support groups, nutritional consultations, physical activity access, and education services are needed at steps, 708, 710, 712, and 714, respectively. If any of the services of steps 708, 710, 712, and 714 are needed, at step 716, it is determined if insurance will cover these services. If not, then at step 718, it is determined if there are free services available. If there are no free services available, then at step 720, as a last resort, the healthcare provider is directed to educate the patient at that time, if possible. If insurance will cover the services or there are free services available, then at step 722, a referral is sent. At step 724, the healthcare provider is directed to educate the patient regarding the arranged services and verify that the patient has access to and an understanding of the services. At step 726, a transportation workflow is initiated to facilitate transportation to the services, if necessary, and at step 728 the process ends.

Figure 8:
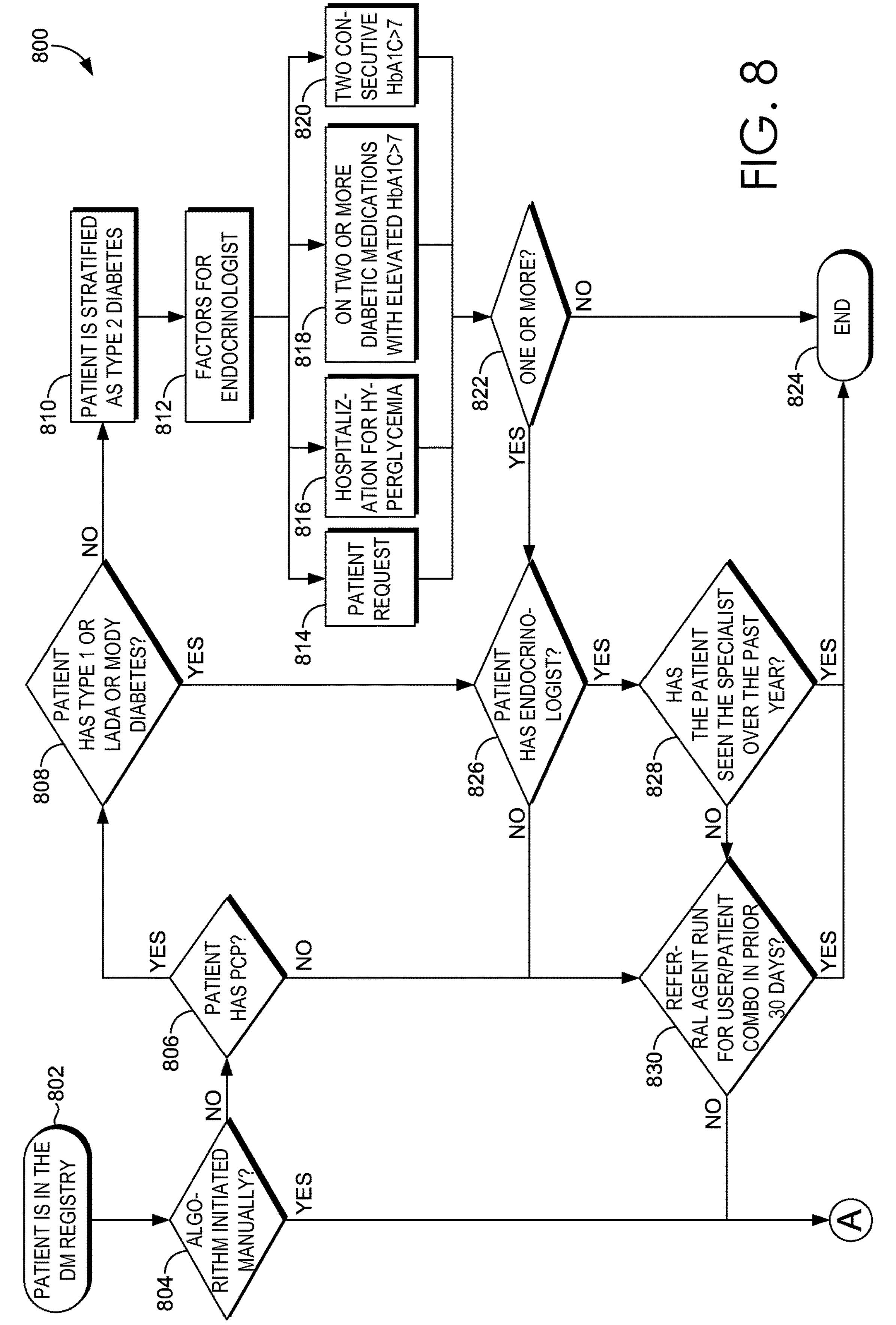
FIG. 8 is a flow diagram illustrating exemplary methods for utilizing an algorithm to provide transition management care, in accordance with embodiments of the present invention.
Figure 8:
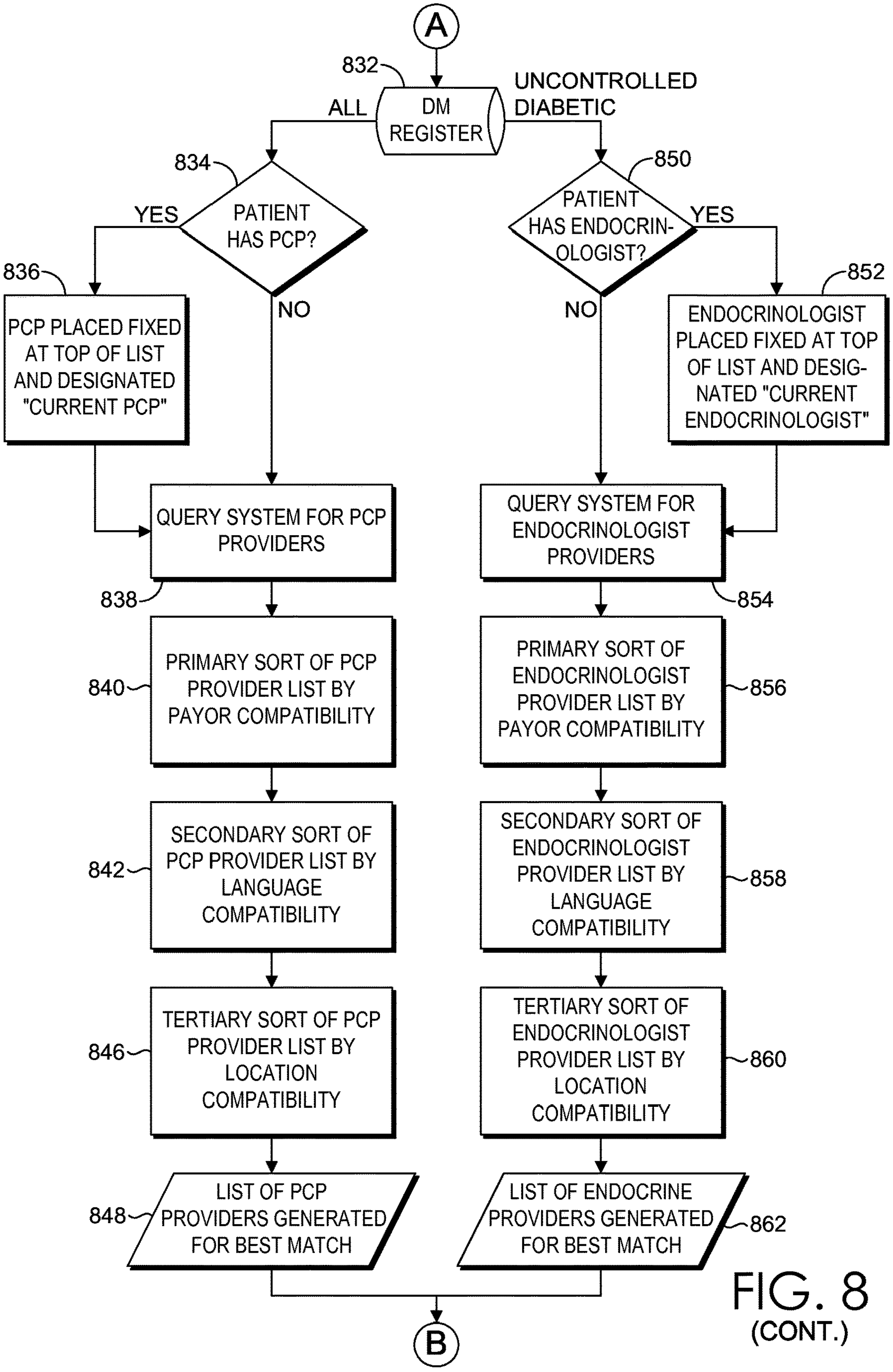
Figure 8:
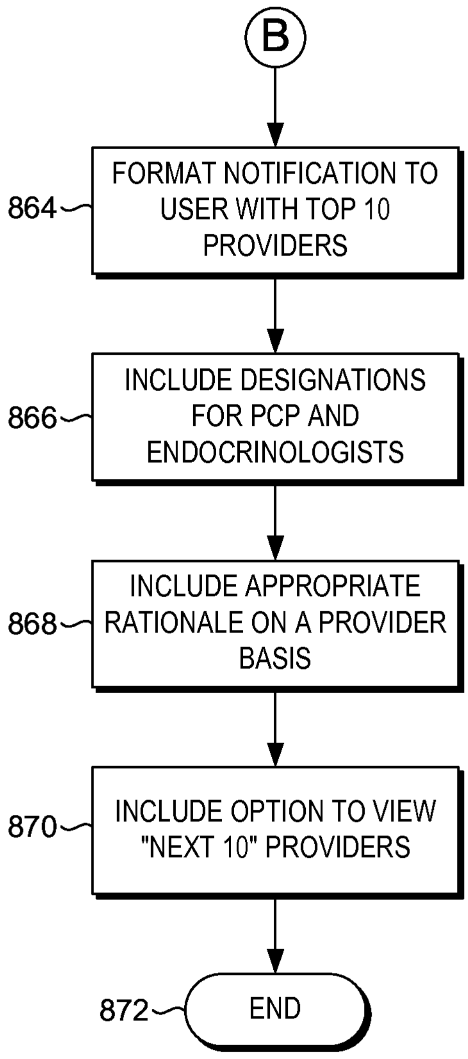

FIG. 8 depicts another embodiment of an algorithm 800 that may be utilized to provide transition management care, if necessary, by determining if a patient requires a referral. It should be understood that the specific steps and the order of the steps depicted in the algorithm 800 are only exemplary and that other steps and different orders of the steps may be user. In addition, it should be understood that there other possible variations for the algorithm 800 within the scope of the present invention.

At step 802, a population health management system, e.g., the population health management system 200 of FIG. 2, may generate or provide patients in a diabetes registry, e.g., an output registry in the registry database 230 of FIG. 2. At step 804, it is determined if the algorithm was initiated manually. If the algorithm was not initiated manually, then at step 806, it is determined if the patient has a primary care provider (PCP). If the patient has a PCP, then at step 808, it is determined if the patient has Type I diabetes, Latent autoimmune diabetes of adults (LADA), or Maturity onset diabetes of the young (MODY). If not, then at step 810, the patient is stratified as having Type II diabetes. Then at step 812, it is determined if there are factors that necessitate referral to an endocrinologist. Then at step 814, it is determined if there is a patient request for an endocrinologist, if the patient. At step 816, it is determined if the patient has been hospitalized for hyperglycemia. At step 818, it is determined if the patient is on two or more diabetic medications and has an elevated HbA1C value greater than 7%. At step 820, it is determined the patient has had two consecutive HbA1C values greater than 7%. At step 822, it is determined if one or more of the criteria determined in steps 814, 816, 818, and 820 are met, and if not, then at step 824, the process ends and a referral is not provided. If one or more of the criteria determined in steps 814, 816, 818, and 820 are met, or if the patient has Type I diabetes, LADA, or MODY, then at step 826 it is determined if the patient has an endocrinologist. If the patient does have an endocrinologist, then at step 828, it is determined if the patient has seen that specialist in the past year, and if so, then at step 824, the process ends and a referral is not provided. If the patient has not seen that specialist in the past year, or if the patient does not have an endocrinologist, then at step 830, it is determined if a referral agent has been run for the combination of the user/healthcare provider and the patient within the last 30 days. If so, then at step 824, the process ends and a referral is not provided. If a referral agent has not been run for the combination of the user/healthcare provider and the patient within the last 30 days, then at step 832 it is determined if the patient in the diabetes registry is an uncontrolled diabetic. If so, then at step 850, it is determined if the patient has an endocrinologist, and if so at step 852, the endocrinologist is placed fixed at the top of the list and is designated as the "current endocrinologist." After step 852, or if it is determined in step 850 that the patient does not have an endocrinologist, at step 854, the system is queried for endocrinologist providers. Then at step 856, a primary sort of an endocrinologist provider list by payor compatibility is performed. Then at step 858 a secondary sort of the endocrinologist provider list by language compatibility is performed. Then at step 860, a tertiary sort of the endocrinologist provider list by location compatibility is performed. Then at step 862, for the patients with uncontrolled diabetes, a list of endocrinologist providers is generated for the best match.

In addition, at step 834, for all the patients in the diabetes registry, it is determined if the patient has a PCP and if so, the PCP is placed fixed at the top of the list and designated as the "current PCP." Regardless of whether the patient has a PCP or not, at step 838, the system is queried for PCP providers. At step 840, a primary sort of a PCP provider list by payor compatibility is performed. Then at step 842 a secondary sort of the PCP provider list by language compatibility is performed. Then at step 846, a tertiary sort of the PCP provider list by location compatibility is performed. Then at step 848, for all the patients in the diabetes registry, a list of PCP providers is generated for the best match.

After steps 848 and 862, at step 864, a notification is formatted to the user and includes the top 10 providers. At step 866, designations for PCPs and endocrinologists are provided. Then at step 868, appropriate rationale on a provider basis is provided. At step 870, an option to view the next ten providers is provider, and at step 872, the process ends.

Figure 9:
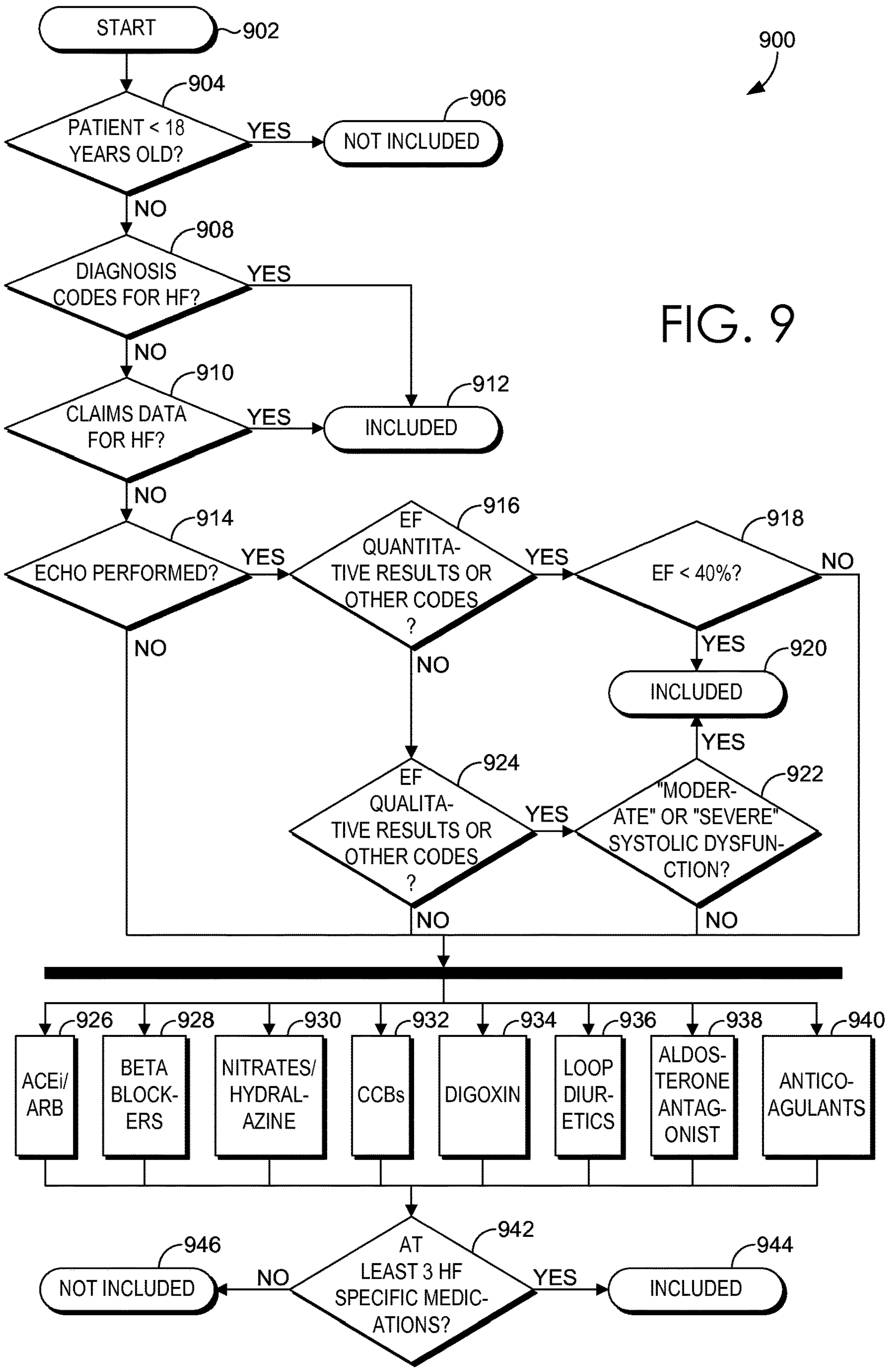
FIG. 9 is a flow diagram illustrating exemplary methods of utilizing an identification algorithm for registry population, in accordance with embodiments of the present invention.

FIG. 9 depicts an exemplary identification algorithm 900 that may be utilized by a population health management system, e.g. the population health management system 200 of FIG. 2, to identify patients that may have heart failure. It should be understood that the specific steps and the order of the steps depicted in the algorithm 900 are only exemplary and that other steps and different orders of the steps may be user. In addition, it should be understood that there other possible variations for the algorithm 900 within the scope of the present invention.

The identification algorithm 900 may include a start step 902, where data associated with one or more patients is received, and then at the step 904 the data is queried to determine if the patient is less than 18 years old. If not, then the patient is excluded from being identified with heart failure. If the patient is not less than 18 years old, then at step 908 it is determined if a diagnosis code for heart failure is present in the healthcare data. If so, then at step 912, the patient is included and identified as having or potentially having heart failure. If there is no diagnosis code for heart failure is present in the healthcare data, then at step 910, it is determined if there is claims data present that suggests the patient has or may have heart failure. If so, then at step 912, the patient is included and identified as having or potentially having heart failure. If the is no claims data present that suggests the patient has or may have heart failure, then at step 914, it is determined if there is data that shows that an echocardiogram was performed. If so, then at step 916, it is determined if there is data for an ejection fraction (EF) quantitative results or other codes associated with EF quantitative results. If there is such data or codes present, at step 918, it is determined if the EF is less than 40%. If the EF is less than 40%, then at step 920, the patient is identified as having or potentially having heart failure and is included in the heart failure registry. If the EF is not less than 40%, then at step 922, it is determined if there is data evidencing moderate or severe systolic dysfunction. If so, then at step 920, the patient is identified as having or potentially having heart failure and is included in the heart failure registry.

If there is no data evidencing moderate or severe systolic dysfunction, or if there is no EF quantitative results or other codes associated with EF quantitative results, or if no echocardiogram was performed, then the patient's data is queried for the presence of several medications. The patient's data is queried for the presence of: ACE inhibitors and angiotensin II receptor blockers at step 926; beta blockers at step 928; nitrates and hydralazine at step 930; calcium channel blockers at step 932; digoxin at step 934; loop diuretics at step 936; aldosterone antagonists at step 938; and anticoagulants at step 940. Then at step 942, it is determined if at least three of the heart failure medications queried in steps 926, 928, 930, 932, 934, 936, 938, and 940 are present, and if so, then at step 944 the patient is identified as having or potentially having heart failure and is included in the heart failure registry. If less than three of the heart failure medications are present, then at step 946, the patient is not identified as having heart failure and is not included in the registry.

Figure 10:
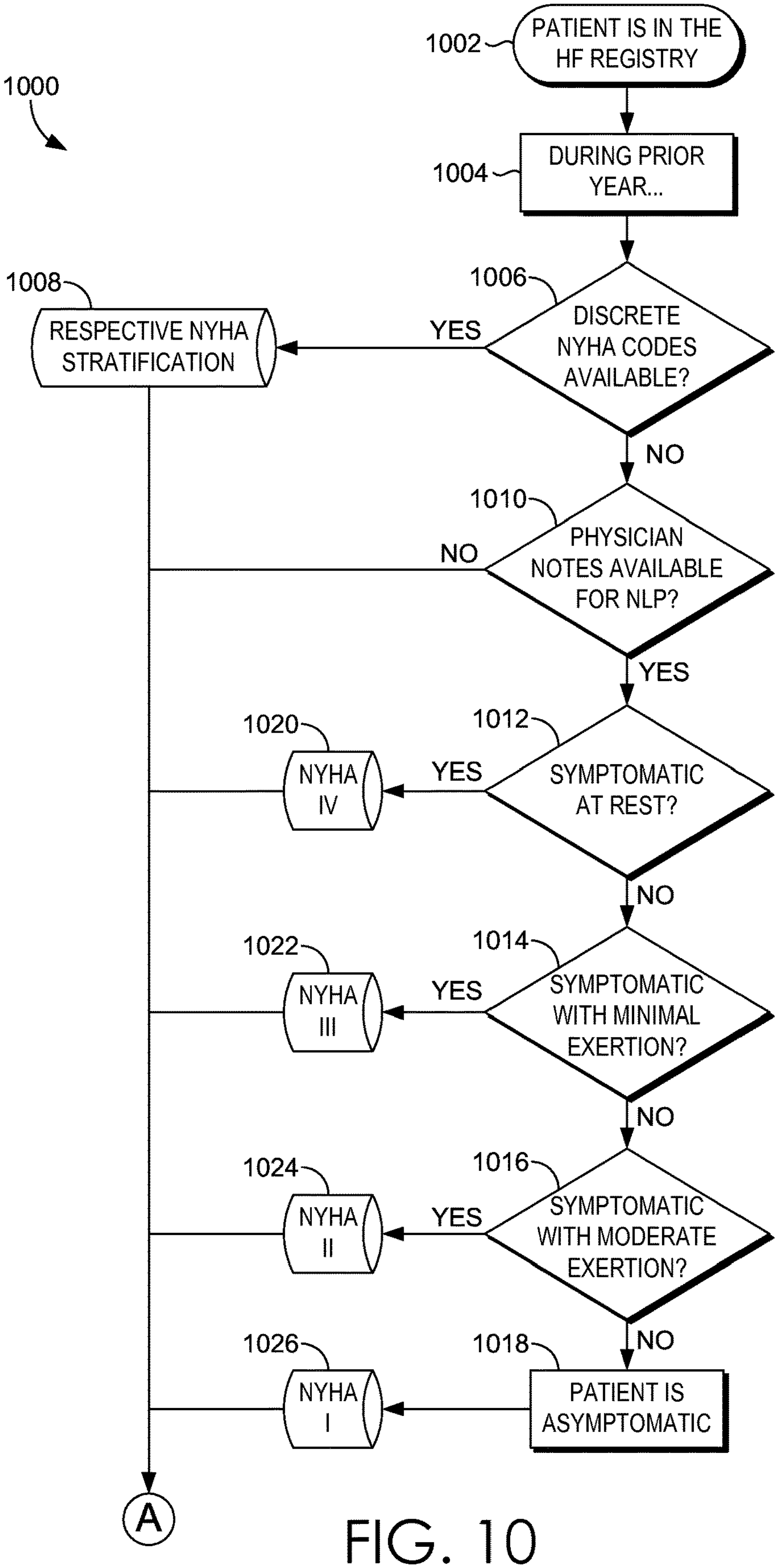
FIG. 10 is a flow diagram illustrating exemplary methods of utilizing a stratification algorithm for stratification one or more patients in a registry, in accordance with embodiments of the present invention.
Figure 10:
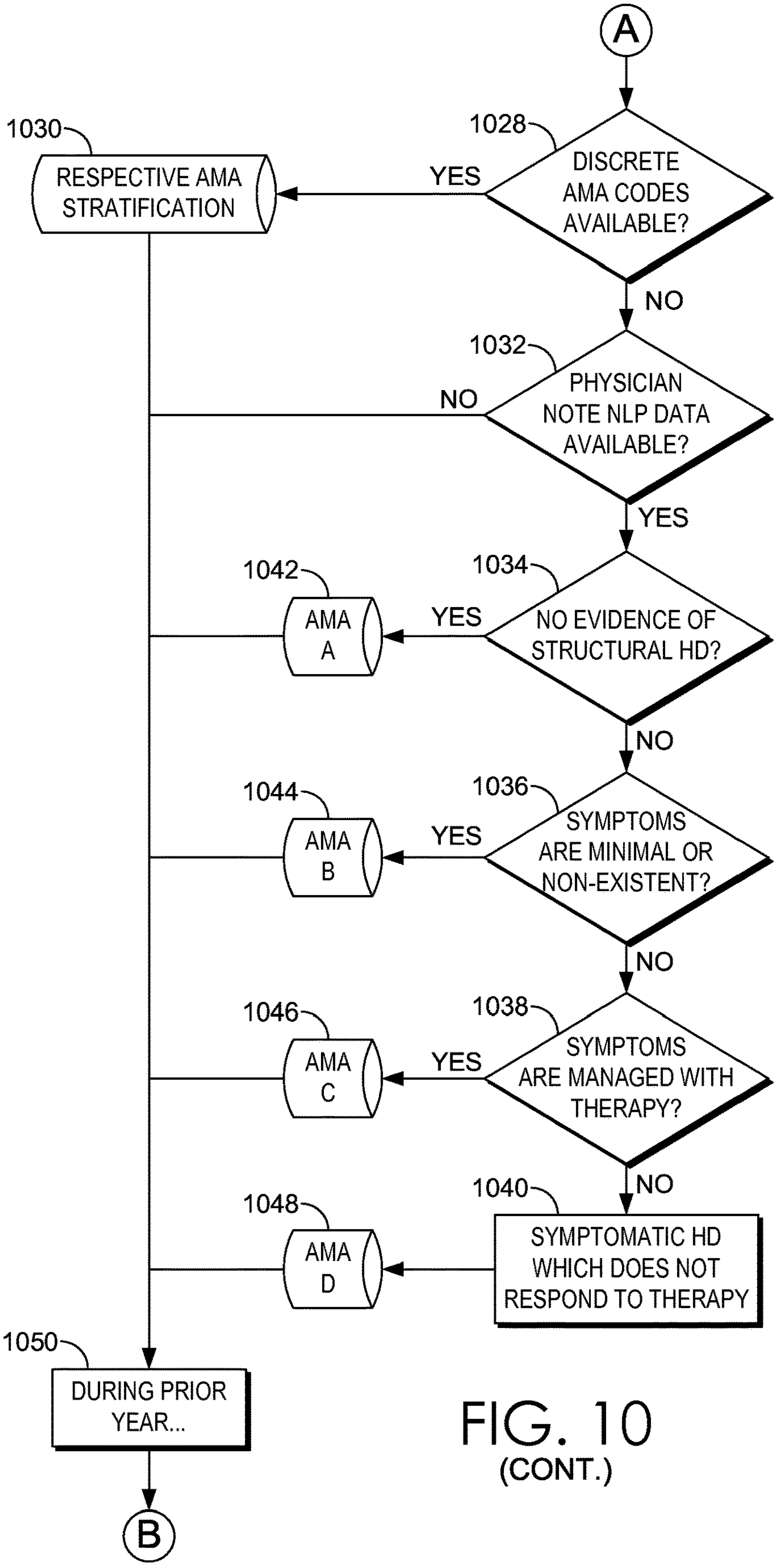
Figure 10:
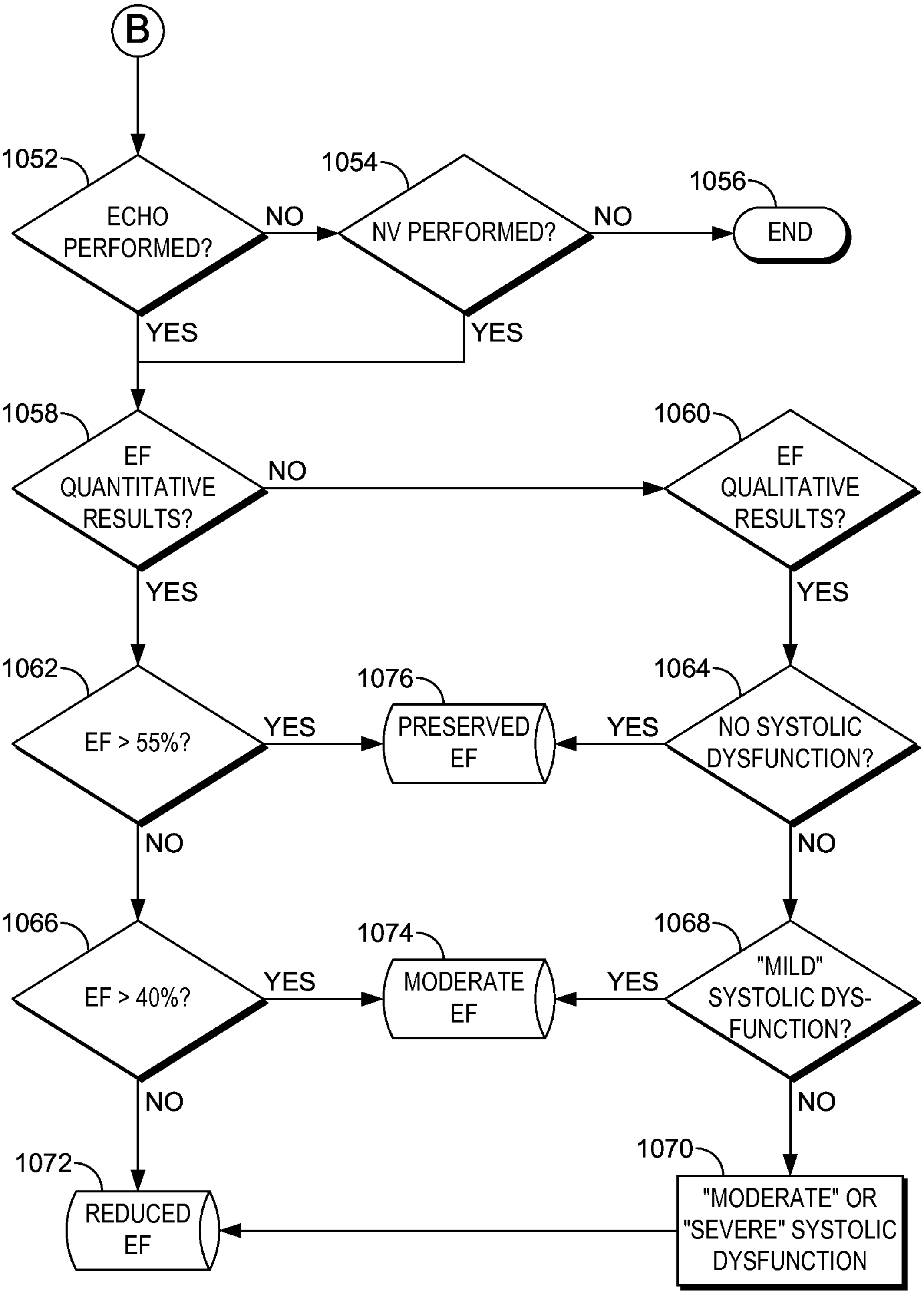

FIG. 10 depicts an exemplary stratification algorithm 1000 is depicted for stratifying one or more patients present in a heart failure registry. It should be understood that the specific steps and the order of the steps depicted in the algorithm 1000 are only exemplary and that other steps and different orders of the steps may be user. In addition, it should be understood that there other possible variations for the algorithm 1000 within the scope of the present invention.

At step 1002, data associated with the patients in the heart failure registry are received. At step 1004, data from the patients in the heart failure registry is filtered only to provide data within the past year, so that for steps 1006 through 1026, a New York Heart Association (NYHA) code can be determined or attempted to be determined for the patient. At step 1006, it is determined if discrete NYHA codes are available in the patient's healthcare data. If so, then in step 1008, the NYHA code is assigned to the patient. If not, at step 1010, it is determined if physician notes are available for natural language processing for determining an NYHA code. If so, then at step 1012, it is determined if the patient is symptomatic at rest, and if so, in step 1020, the patient is assigned the NYHA IV code. If the patient is not symptomatic at rest, then in step 1014, it is determined if the patient is symptomatic with minimal exertion, and if so, in step 1022, the patient is assigned the NYHA III code. If the patient is not symptomatic with minimal exertion, then in step 1016, it is determined if the patient is symptomatic with moderate exertion, and if so, in step 1024, the patient is assigned the NYHA II code. If the patient is not symptomatic with moderate exertion, then in step 1018, it is determined if the patient is asymptomatic, and if so, in step 1026, the patient is assigned the NYHA I code.

After assigning the NYHA code to the patient or not being able to assign an NYHA code to the patient, in step 1028, it is determined if American Medical Association (AMA) codes are available in the patient's healthcare data. If so, then in step 1030, the AMA code is assigned to the patient. If no AMA codes are available in the patient's healthcare data, then at step 1032, it is determined if there are physician notes available for natural language processing for determining an AMA code. If so, then in step 1034, it is determined if there is no evidence of structural heart damage. If so, then in step 1042, the patient is assigned the AMA code A. If there is not any evidence of structural heart damage, then in step 1036, it is determined if the patient's symptoms are minimal or nonexistent. If the symptoms are minimal and nonexistent, then in step 1044, the patient is assigned the AMA code B. If the symptoms are not minimal and nonexistent, then in step 1038, it is determined if the symptoms are managed with therapy. If the symptoms are managed with therapy, then in step 1046, the patient is assigned the AMA code C. If the symptoms are not managed with therapy, then in step 1040, it is determined if the patient has symptomatic heart disease that does not respond to therapy, and if so, in step 1048, the patient is assigned the AMA code D.

After assigning the AMA code to the patient or not being able to assign an AMA code to the patient, in step 1050, the data from the patients in the heart failure registry is filtered only to provide data within the past year, so that for steps 1052 through 1076, Ejection Fraction (EF) classifications can be determined. In step 1052, it is determined if an echocardiogram has been performed. If not, then at step 1054, it is determined if an NV test has been performed. If not, then the process ends and no EF classification is determined. If an NV test or an echocardiogram has been performed, then at step 1058, it is determined if there are EF quantitative results. If so, at step 1062, it is determined if the EF quantitative results reveal an EF greater than 55%. If so, then the patient is classified as having a preserved EF at step 1076. If the EF quantitative results do not reveal an EF greater than 55%, then at step 1066, it is determined if the EF quantitative results reveal an EF greater than 40%. If so, in step 1074, the patient is classified as having a moderate EF. If the EF quantitative results do not reveal an EF greater than 40%, then at step 1072, the patient is classified as having a reduced EF.

If there are no quantitative EF results, at step 1060, it is determined if there are EF qualitative results. If so, in step 1064, it is determined if there is no systolic dysfunction. If there is not systolic dysfunction, then in step 1076, the patient is classified as having a preserved EF. If it is determined that there is not no systolic dysfunction, then in step 1068, it is determined if the patient has mild systolic dysfunction. If so, then the patient is classified as having a moderate EF in step 1074. If it is determined that the patient does not have mild systolic dysfunction, then in step 1070, it is determined if the patient has moderate or severe systolic dysfunction. If so, the patient is classified as having a reduced EF.

Figure 11:
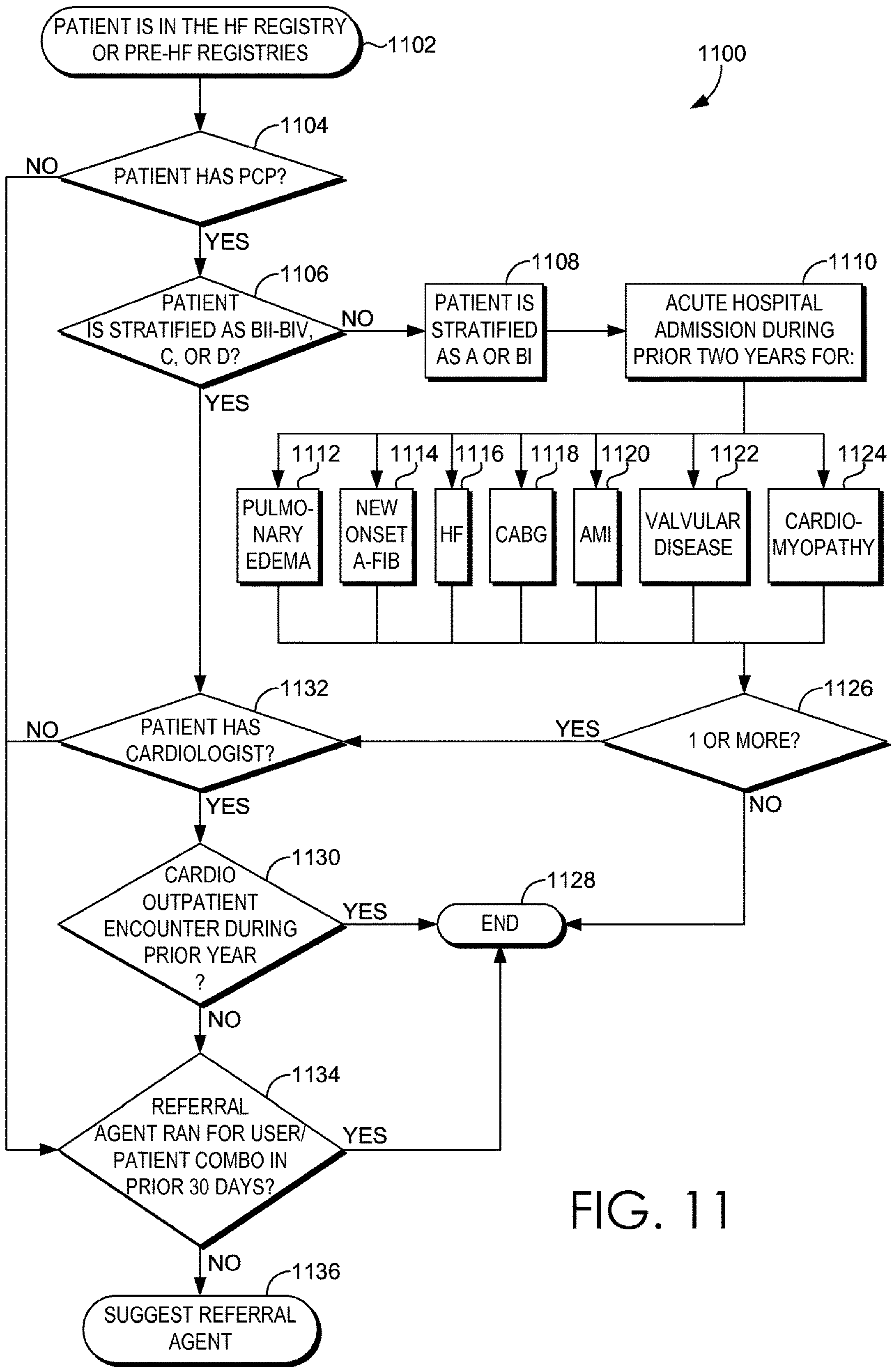
FIG. 11 is a flow diagram illustrating exemplary methods for utilizing an algorithm to provide transition management care, in accordance with embodiments of the present invention.

As discussed above, in certain embodiments, a population health management system, e.g., the population health management system 200 of FIG. 2, can aid in providing transition management care for one or more patients, such as determining if a referral is needed for a patient. FIG. 11 depicts one embodiment of an algorithm 1100 that may be used to determine whether a patient needs a referral or not. It should be understood that the specific steps and the order of the steps depicted in the algorithm 1100 are only exemplary and that other steps and different orders of the steps may be user. In addition, it should be understood that there other possible variations for the algorithm 1100 within the scope of the present invention.

At step 1102 data from the patients in the heart failure registry and/or the pre-heart failure registry is received. In step 1104, it is determined if the patient has a PCP. If so, then in step 1106, it is determined if the patient was stratified as having class BII-BIV, C, or D heart failure. If not, then in step 1108, it is determined if the patient was stratified as having class A or BI heart failure. If so, then in step 1110, it is determined if the patient had an acute hospital admission during the prior two years for specific diseases or treatments as determined in steps 1112-1124. The specific diseases are pulmonary edema, new onset atrial fibrillation, heart failure, coronary artery bypass grafting (CABG), acute myocardial infarction (AMI), valvular disease, cardiomyopathy for steps 1112, 1114, 1116, 1118, 1120, 1122, and 1124, respectively. At step 1126, it is determined if one or more of the diseases or treatments of determined in 1112, 1114, 1116, 1118, 1120, 1122, and 1124 occurred for the patient, If not, then the process ends and no referral is made. If the patient has had one or more of the diseases or treatments of determined in 1112, 1114, 1116, 1118, 1120, 1122, and 1124, or if the patient is stratified as having class BII-BIV, C, or D heart failure, in step 1132, it is determined if the patient has a cardiologist. If so, in step 1130, it is determined if the patient has had a cardiologist outpatient encounter within the last year. If so, in step 1128, the process ends and no referral is made. If the patient has not had a cardiologist outpatient encounter within the last year, at step 1134, it is determined if a referral agent was run for the healthcare provider and patient combination in the past 30 days. If so, in step 1128, the process ends and no referral is made. If not, then in step 1136, a suggestion is provided to the healthcare provider for the referral agent.

Figure 12:
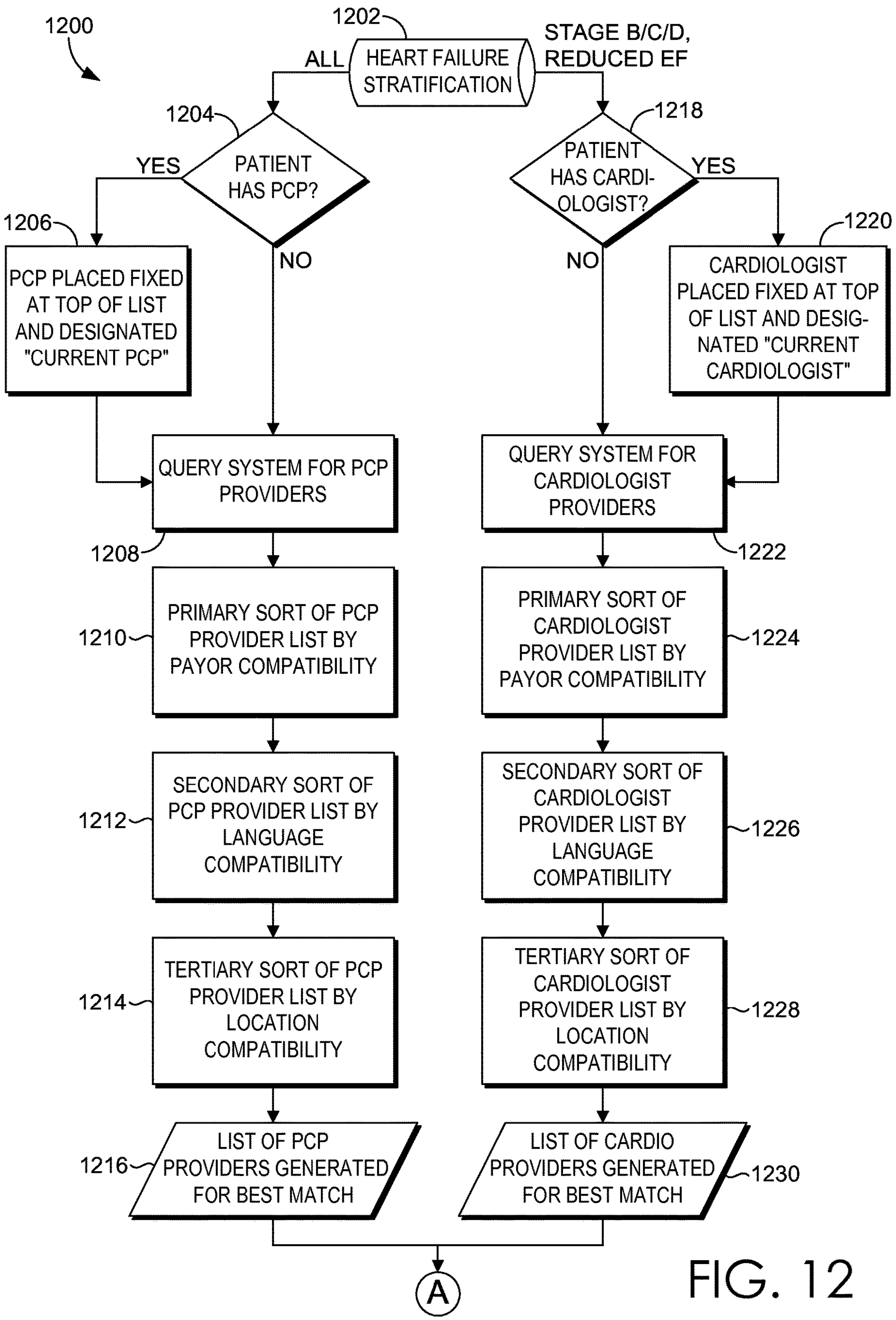
FIG. 12 is a flow diagram illustrating exemplary methods for utilizing an algorithm for assigning a physician to one or more patient in a heart failure registry, in accordance with embodiments of the present invention.
Figure 12:
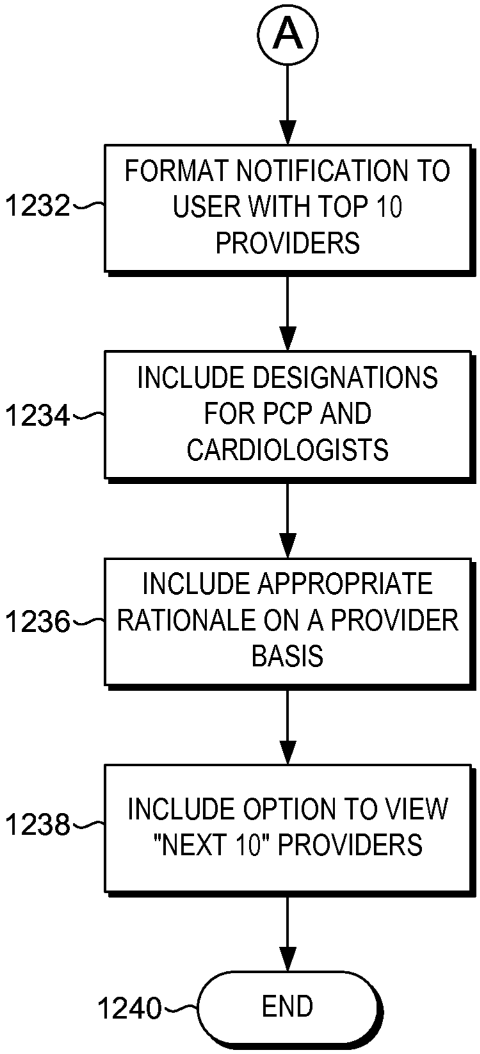

FIG. 12 depicts an algorithm 1200 for assigning a physician to one or more patient in a heart failure registry. It should be understood that the specific steps and the order of the steps depicted in the algorithm 1200 are only exemplary and that other steps and different orders of the steps may be user. In addition, it should be understood that there other possible variations for the algorithm 1200 within the scope of the present invention.

At step 1202, data from one or more patients in a heart failure registry is received. At step 1218, for one or more patients classified as having class B, C, D heart failure or reduced EF, it is determined if such a patient has a cardiologist. If so, then at step 1220, the cardiologist is placed fixed at the top of the list and is designated as the "current cardiologist." After step 1220, or if it is determined in step 1218 that the patient does not have a cardiologist, at step 1222, the system is queried for cardiologist providers. Then at step 1224, a primary sort of a cardiologist provider list by payor compatibility is performed. Then at step 1226 a secondary sort of the cardiologist provider list by language compatibility is performed. Then at step 1228, a tertiary sort of the cardiologist provider list by location compatibility is performed. Then at step 1230, for the patients having class B, C, D heart failure or reduced EF, a list of cardiologist providers is generated for the best match.

In addition, at step 1204, for all the patients in the heart failure registry, it is determined if the patient has a PCP and if so, the PCP is placed fixed at the top of the list and designated as the "current PCP" in step 1206. Regardless of whether the patient has a PCP or not, at step 1208, the system is queried for PCP providers. At step 1210, a primary sort of a PCP provider list by payor compatibility is performed. Then at step 1212 a secondary sort of the PCP provider list by language compatibility is performed. Then at step 1214, a tertiary sort of the PCP provider list by location compatibility is performed. Then at step 1216, for all the patients in the heart failure registry, a list of PCP providers is generated for the best match.

After steps 1216 and 1230, at step 1232, a notification is formatted to the user and includes the top 10 providers. At step 1234, designations for PCPs and cardiologists are provided. Then at step 1236, appropriate rationale on a provider basis is provided. At step 1238, an option to view the next ten providers is provider, and at step 1240, the process ends.

Figure 13:
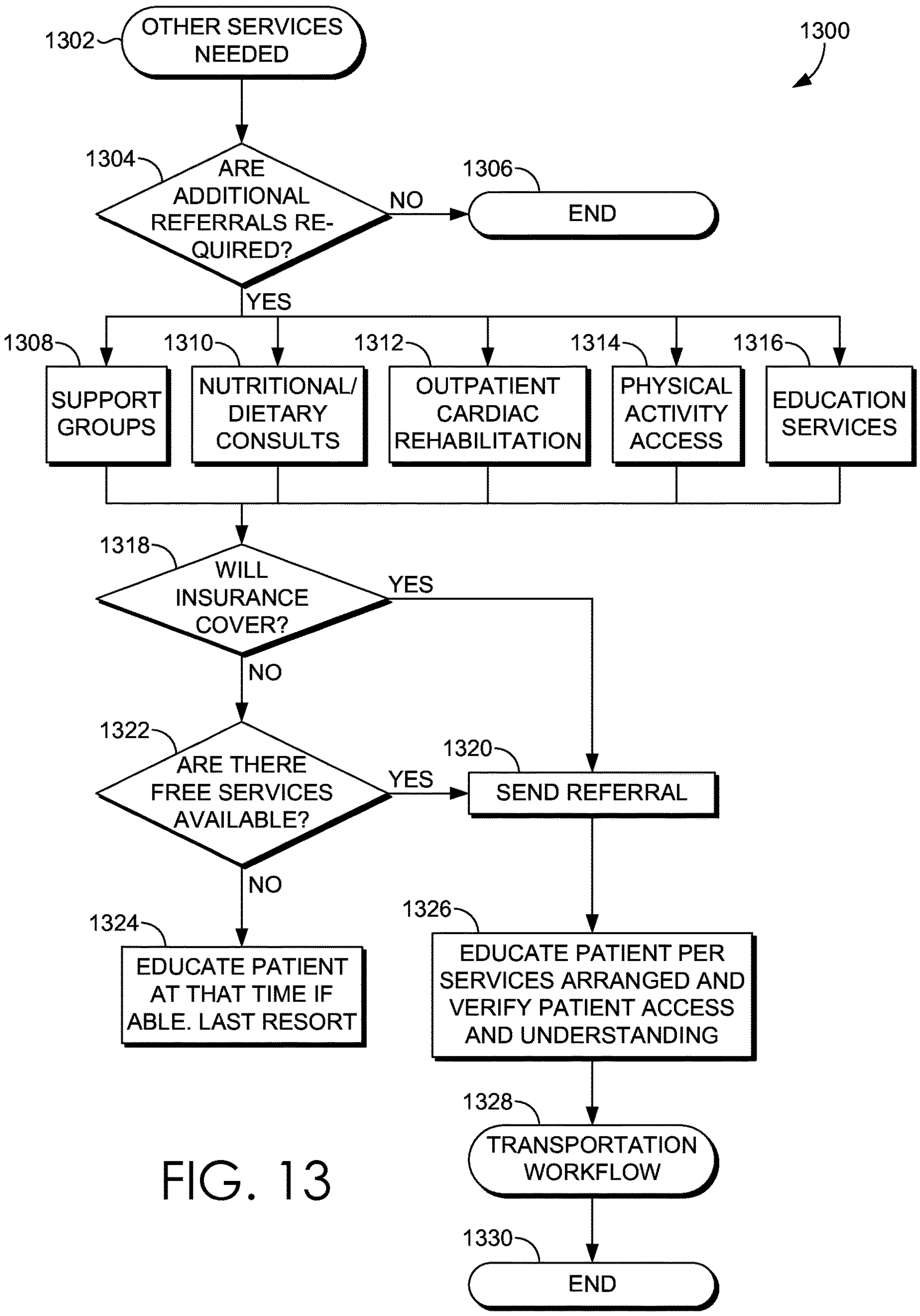
FIG. 13 is a flow diagram illustrating exemplary methods for utilizing an algorithm to provide transition management care, in accordance with embodiments of the present invention.

FIG. 13 depicts an algorithm 1300 that may be utilized to provide transition management care by facilitating the provision of additional services for a patient. It should be understood that the specific steps and the order of the steps depicted in the algorithm 1300 are only exemplary and that other steps and different orders of the steps may be user. In addition, it should be understood that there other possible variations for the algorithm 1300 within the scope of the present invention.

At step 1302, it is determined that other services, such as follow up support, education, etc., may be necessary for the patient. At step 1304, it is determined if additional referrals are required for the additional services, and if not, at step 1306 the process stops. If additional referrals are required, it is determined if support groups, nutritional consultations, outpatient cardiac rehabilitation, physical activity access, and education services are needed at steps, 1308, 1310, 1312, 1314, and 1316, respectively. If any of the services of steps 1308, 1310, 1312, 1314, and 1316 are needed, at step 1318, it is determined if insurance will cover these services. If not, then at step 1322, it is determined if there are free services available. If there are no free services available, then at step 1324, as a last resort, the healthcare provider is directed to educate the patient at that time, if possible. If insurance will cover the services or there are free services available, then at step 1320, a referral is sent. At step 1326, the healthcare provider is directed to educate the patient regarding the arranged services and verify that the patient has access to and an understanding of the services. At step 1328, a transportation workflow is initiated to facilitate transportation to the services, if necessary, and at step 1330 the process ends.

FIGS. 14-27 depict various aspects of a population health management system, e.g., the population health management system 200. The aspects of the population health management system depicted in FIGS. 14-27 are merely exemplary and it should be understood that additional aspects or variations on the aspects depicted in FIGS. 14-27 are within the scope of the present invention.

FIG. 14 depicts an overview 1400 of a health system that can be provided to a healthcare provider 1410. The healthcare provider 1410 can be any healthcare provider associated with the health system, such as a physician, physician's assistant, nurse, care manager, and/or administrator. The overview 1400 can be displayed on one or more devices, such as the devices 240 discussed above with reference to FIG. 2. In one or more embodiments, the overview 1400 may be generated, at least in part, by one or more components of a population health server, such as the population health server 250 discussed above with reference to FIG. 2.

In certain embodiments, the overview 1400 can include a key performance indicator module 1420. In such embodiments, the key performance indicator module 1420 can include various indicators that represent different features of a health system, such as health system utilization 1422, financial information 1424, healthcare quality of 1426, operational indicators 1428, health system access indicators 1430, and/or appropriateness of the healthcare 1432.

In one or more embodiments, the overview can include alerts 1440 associated with the health system. In certain embodiments, the alerts 1440 can include alerts for trends associated with a population of patients cared for by the health system. For example, as depicted in FIG. 14, the alerts 1440 can include information related to rate of readmissions, compliance issues, and/or rate or number of prescriptions being filled for a specific group of patients. In the embodiment depicted in FIG. 14, the healthcare provider 1410 has the option of addressing, dismissing, or snoozing one or more alerts 1440 from this overview 1400.

In certain embodiments, the overview 1400 can include patient population information 1450. In such embodiments, the patient population information 1450 may include general characterizations of the patient population in the health system. For example, in one embodiment, the patient population information 1450 can include the percentage of the patient population present in various classifications, such as being classified as having chronic conditions.

In various embodiments, the overview 1400 can include demographic information 1460 on the patient population present within the health system. In the same or alternative embodiments, the overview can include satisfaction metrics 1470 associated with the satisfaction of patients and/or employees of the health system.

In certain embodiments, the information associated with the overview 1400 can include information organized in various tabs, such as the tabs 1480. In such embodiments, the health care provider 1410 can view information associated with the payers or provider groups. In the same or alternative embodiments, the health care provider 1410 can view information associated with medical conditions or various health system programs.

In various embodiments, the overview 1400 can also include additional tabbed portions 1490 where the healthcare provider 1410 can view information associated with one or more registries, scorecards, medications, or outreach.

FIG. 15 depicts a program view 1500 for a specific program associated with a health system. The program view 1500 may be displayed on one or more devices, such as the devices 240 discussed above with reference to FIG. 2. In one or more embodiments, the overview 1500 may be generated, at least in part, by one or more components of a population health server, such as the population health server 250 discussed above with reference to FIG. 2.

In certain embodiments, the program view 1500 may be associated with a particular program offered by the health system. For example, in the embodiment depicted in FIG. 15, the program view 1500 includes a view of a diabetes program. In certain embodiments, a healthcare provider, e.g., the healthcare provider 1510, can navigate to the program view 1500 via a health system overview, such as the health system overview 1400 of FIG. 14. In such embodiments, a healthcare provider can navigate to the program view 1500 by clicking on a link 1442 to address an alert in the overview 1400 of FIG. 14.

Returning now to FIG. 15, in certain embodiments, the program view 1500 can include all available information related to a population of patients being treated for diabetes within the health system. For example, in such embodiments, the program view 1500 can include a column listing indicators or measures associated with the population of patients being treated for diabetes, such as one or more of: key performance indicators 1520; quality measures 1530; prescription information 1540; consultations/appointments attendance information 1550; and personal patient documentation 1560 (such as logging of diet and/or home glucose tests). In one or more embodiments, the program view 1500 can provide a main program view area 1542 of one or more of the indicators or measures 1520, 1530, 1540, 1550, and 1560.

In the embodiment depicted in FIG. 15, the main program view area 1542 provides information associated with the prescriptions filed measure 1540 from the column listing. In embodiments, the main program view 1542 may be formatted differently depending upon which indicators or measures 1520, 1530, 1540, 1550, and/or 1560 the healthcare provider 1510 is highlighting for display. As seen in the embodiment depicted in FIG. 15, a main program view area 1542 may display a map 1544 highlighting pharmacies and clinics. In such embodiments, the main program view area 1542 can illustrate the percentage of prescriptions filled at each of the pharmacies and clinics on the map 1544. In one or more embodiments, the main program view area 1542 can include a list 1580 of various types of entities to display on the map 1544.

FIG. 16 depicts a healthcare provider overview 1600 for a healthcare provider, such as the healthcare provider 1610. In embodiments, the healthcare provider 1610 can be any healthcare provider associated with the health system, such as, a physician, physician's assistant, nurse, care manager, and/or administrator. The healthcare provider overview 1600 may be displayed on one or more devices, such as the devices 240 discussed above with reference to FIG. 2. In one or more embodiments, the healthcare provider overview 1600 may be generated, at least in part, by one or more components of a population health server, such as the population health server 250 discussed above with reference to FIG. 2.

The healthcare provider overview 1600 can include any or all information associated with the healthcare provider 1610 for a particular health system. In such embodiments, the healthcare provider overview 1600 can include more than one potential display area. For example, in the embodiment depicted in FIG. 16, the healthcare provider overview 1600 can include the tabs 1660 to enable the healthcare provider 1610 to view information associated with various categories, such as worklist, outreach, performance, and connections. In one or more embodiments, the healthcare provider overview 1600 can include a home view option 1662 to view information from several categories at once. For example, in certain embodiments, the home view option 1662 of the healthcare provider overview 1600 can include a communications area 1620, a schedule area 1630, a performance area 1640, and/or a worklist area 1650. In the embodiment depicted in FIG. 16, the communications area 1620 can include: an inbox area 1622 that can display at least a representation of incoming messages, e.g., emails; a notification area 1624 that can display at least a portion of notifications relating to the healthcare provider's duties, and/or an announcement area 1626 to display announcements relating to the healthcare provider or the health system.

In one or more embodiments, the schedule area 1630 can include scheduling information associated with the healthcare provider's duties. For instance, the schedule area can include a daily schedule component 1632 of patient appointments for the healthcare provider 1610. In the same or alternative embodiments, the schedule area 1630 can include a reminders component 1634 to display reminders set up by or set up for the healthcare provider 1610.

In certain embodiments, the performance area 1640 can include information regarding the performance of the healthcare provider 1610 as it relates to various metrics associated with the patients under the care of the healthcare provider 1610. For example, in one or more embodiments, the performance area 1640 can include information related to the high risk population of patients 1642 seen by the healthcare provider 1610, the top 5 chronic conditions 1644 of the population of patients seen by the healthcare provider 1610, and/or the treatment trends 1646, e.g., out of network utilization, of the population of patients seen by the healthcare provider 1610.

In one or more embodiments, the worklist area 1650 may include alerts for one or more worklists associated with the healthcare provider 1610. In one embodiment, the worklist area 1650 can include any alerts for which a population health management system, such as the population health management system 200 of FIG. 2, has deemed relevant for the healthcare provider 1610 to be aware of. For example, in certain embodiments, the worklist area 1650 can include alerts and/or notifications for the healthcare provider 1610 to be aware of new people that have been added to a registry or program, e.g., the alert 1652. In the same or alternative embodiments, other alerts can be provided in the worklist area 1650, such as alerts relating to the patients seen by the healthcare provider 1610 that detail emergency room visits, hospital discharge, readmission risk, and/or home device alerts.

In certain embodiments, one or more of the areas 1620, 1630, 1640, and 1650 can include items that comprise links that lead to more expanded views or to another view. For example, in one or more embodiments, when the healthcare provider 1610 clicks and/or touches the registry/programs worklist (New Persons Qualify) tile 1652 in the worklist area 1650, a new view 1700 may be opened, which is depicted in FIG. 17.

In one or more embodiments, the view 1700 of FIG. 17 may be generated, at least in part, by one or more components of a population health server, such as the population health server 250 discussed above with reference to FIG. 2. In certain embodiments, a healthcare worker, e.g., the healthcare worker 1710, may choose to highlight information related to one of the patients provided on the worklist new persons list 1720, such as the patient 1748. In such embodiments, upon choosing to highlight a specific patient, a situational view 1730 may be provided. The situational view 1730 can include a patient information area 1738, a vitals and measurements area 1732, an appointments list area 1734, a care plan area 1736, an alerts area 1740, a longitudinal record area 1744, and/or a care team list 1746.

The patient information area 1738 may include background information on the patient 1748, such as age, contact information, and health insurance information. In certain embodiments, the vitals and measurements area 1732 can include data including blood pressure readings, height, weight, temperature, and/or heart rate. In the one or more embodiments, the appointments area 1734 may include a list of upcoming and/or previous medical appointments for the patient 1748. In one or more embodiments, the care plan information 1736 can include medication information, diet information, exercise information, medical condition education, and/or appointments, recommended by one or more healthcare providers.

In various embodiments, the alerts area 1740 can include alerts related to the patient 1748. In such embodiments, the alerts can include any information that a healthcare provider, e.g., the healthcare provider 1710, may find relevant for providing care to the patient, such as that the patient 1748 that has been newly added to a diabetes registry.

In certain embodiments, the longitudinal record area 1742 can include a list of any longitudinal records associated with one or more conditions of the patient 1748. In such embodiments, the healthcare provider 1710 can click and/or touch one or more of the listed longitudinal records to display the full longitudinal record. In the same or alternative embodiments, the longitudinal record area 1742 may include a list of medications that the patient 1748 is currently taking or is prescribed to be taking. In one or more embodiments, this list of medications may include medications that the patient is no longer taking. An exemplary longitudinal record is depicted in FIG. 18.

In one or more embodiments, the care team list 1746 can include a list of all the care team members, such as physicians, specialists, care managers, etc., associated with the patient 1748. In certain embodiments, the care team list 1746 can include links to contacting any or all of the individual care team members.

In the embodiment depicted in FIG. 18, the view 1800 is identical to the view 1700 discussed above with reference to FIG. 17 with the exception that the view 1800 includes an overlaid longitudinal record 1810. In embodiments, the longitudinal record 1810 may be associated with a patient, e.g., the patient 1748 of FIG. 17.

In certain embodiments, the longitudinal record 1810 may be presented in any form known to one skilled in the art. For example, in embodiments, the longitudinal record 1810 may be presented as a pop-up window overlaying another view, such as the view 1800. In one or more embodiments, the longitudinal record 1810 may be generated, at least in part, by one or more components of a population health server, such as the population health server 250 discussed above with reference to FIG. 2.

In certain embodiments, the longitudinal record 1810 can include a timeline view area 1820, a potential complications viewing area 1830, a medication list area 1840, and/or an education area 1850. In embodiments, the timeline view area 1820 can include a timeline view 1822 that provides all the medical information associated with a patient, e.g., the patient 1748, regarding at least one medical condition, and may include information across all providers and/or across all venues.

In one or more embodiments, the healthcare provider 1860 may interact with the timeline view 1822 to reveal all or a portion of the medical information related to a medical condition for a specified time. In one embodiment, the timeline view 1822 can allow a healthcare provider, e.g., the healthcare provider 1860, to view information related to all clinical visits and clinical results associated with a particular condition, e.g., diabetes, since the patient was diagnosed with the condition up until the present moment. For example, as can be seen in the embodiment depicted in FIG. 18, medical information window 1824 is displayed, which specifically details a random blood glucose measurement associated with Oct. 10, 2013 at 10:35 AM. In certain embodiments, the scale of the timeline view 1822 may be changed by a healthcare provider, e.g., the healthcare provider 1860, using the timeline scaling tool 1826.

In one or more embodiments, the potential complications viewing area 1830 can include a list of one or more potential complications associated with the medical condition of interest, such as diabetes. For example, the potential complications viewing area 1830 displays that there is a 27% chance of congestive heart failure in the next 12 months.

In certain embodiments, the medication list area 1840 can include a list of all medications that a patient, e.g., the patient 1748, is currently taking or is prescribed to take for any medical condition. In various embodiments, the medication list area 1840 may include a list of all the medications that a patient is currently taking or is prescribed to take that are related to the medical condition of interest, e.g., diabetes.

In various embodiments, the education area 1850 can include a list of education programs recommended by a healthcare provider, e.g., the healthcare provider 1860, for a patient related to the medical condition of interest. In the embodiment depicted in FIG. 18, the education area includes a list of the education programs recommended by a healthcare provider and additionally can include information on whether or not such education programs have been completed by the patient.

Figure 19:
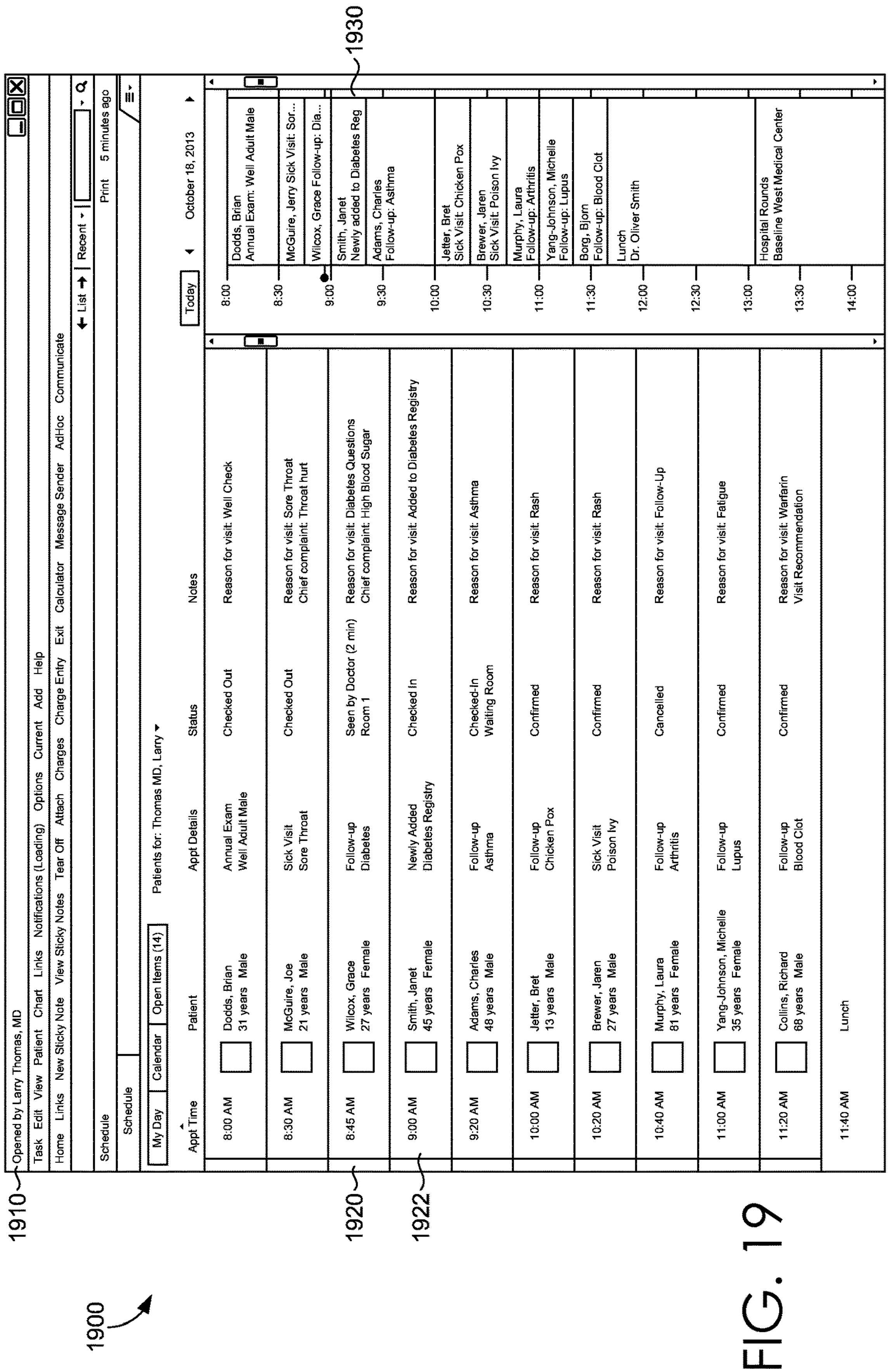

FIG. 19 depicts a schedule view 1900 for a healthcare provider 1910 in accordance with one embodiment of the present invention. The schedule view 1900 may include a patient appointment list 1920 for a specific day. In the same or alternative embodiments, the schedule view can include a column view 1930 that may include an abbreviated schedule for the healthcare provider 1910.

In various embodiments, the schedule view 1900 can include information that has been generated, at least in part, by one or more components of a population health server, such as the population health server 250 discussed above with reference to FIG. 2.

In certain embodiments, any or all of the components in the appointment list 1920 and/or column view 1930 can include links to further information about the appoint or patient associated with the appointment. For example, in one or more embodiments, the healthcare provider 1910 may click on an area associated with a particular patient appointment, such as the appointment for the patient 1922 to reveal relevant information about this patient, such as that depicted in the patient information view 2000 of FIG. 20.

Figure 20:
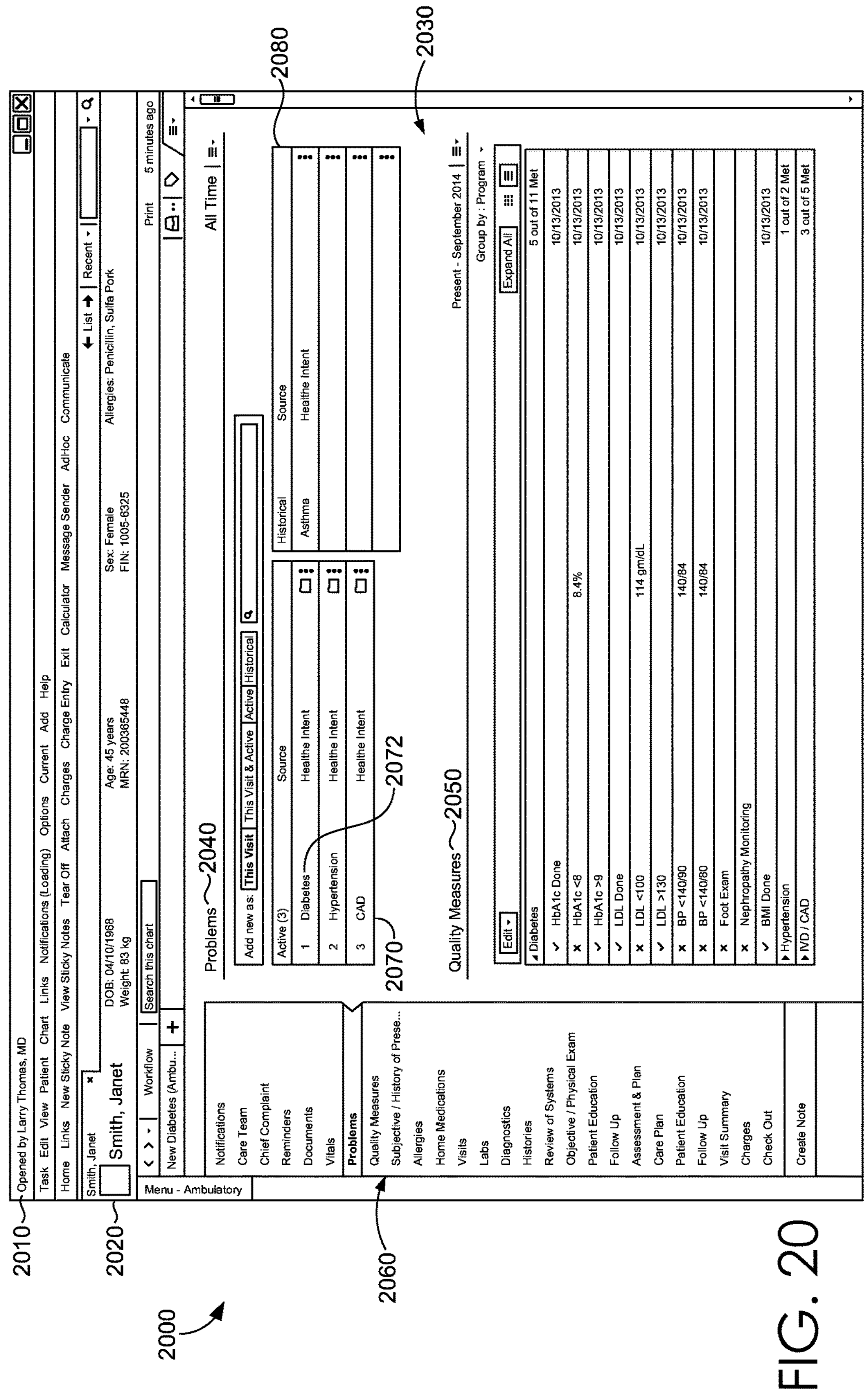

The patient information view 2000 depicted in FIG. 20 can include any or all of the relevant information related to a particular patient, such as the patient 1922 described above with reference to FIG. 19. In various embodiments, the patient information view 2000 can include information that has been generated, at least in part, by one or more components of a population health server, such as the population health server 250 discussed above with reference to FIG. 2.

In certain embodiments, the patient information view 2000 can include a general patient information area 2020, a main view area 2030, and a navigation area 2060. The patient information area 2020 may include general patient information that may be relevant to the healthcare provider 2010 when viewing medical problems associated with the patient, such as age, weight, and/or prescription allergies.

In certain embodiments, the navigation area 2060 may list various categories of information associated with the patient through which the healthcare provider 2010 may interact to view additional patient information. In certain embodiments, the additional patient information may be populated in the main view area 2030 and/or may appear as a pop-up window on top of the patient information view 2000.

In one or more embodiments, the main view area 2030 may include a problems area 2040 and a quality measures area 2050. In such embodiments, the problems area 2040 may include a list of active 2070 and historical 2080 problems for the patient, such as the active diabetes problem 2072 for the patient. Further, in such embodiments, the healthcare provider 2010 may click on and/or touch any or all of the active 2070 and/or the historical 2080 problems listed in the problems area 2040 to view additional information associated with that problem. For example, in one or more embodiments, when the healthcare provider 2010 clicks on and/or touches the diabetes problem 2072, a pop-up condition view may appear, such as that depicted in FIG. 21.

As can be seen in the embodiment depicted in FIG. 21, a pop-up condition view 2110 can display over a patient information view 2100. In the embodiment depicted in FIG. 21, the patient information view 2100 of FIG. 21 is substantially identical to the patient information view 2000 described above with reference to FIG. 20 except for the presence of the pop-up condition view 2110. In certain embodiments, the pop-up condition view 2110 can include a longitudinal record 2120 associated with a particular medical condition, e.g., a diabetes condition. In such embodiments, the longitudinal record 2120 may include all the properties and components as the longitudinal record 1810 discussed above with reference to FIG. 18. For example, in such embodiments, the longitudinal record 2120 may include a timeline view area 2130, a potential complications viewing area 2140, a medication list area 2150, and/or an education area 2160.

Figure 22:
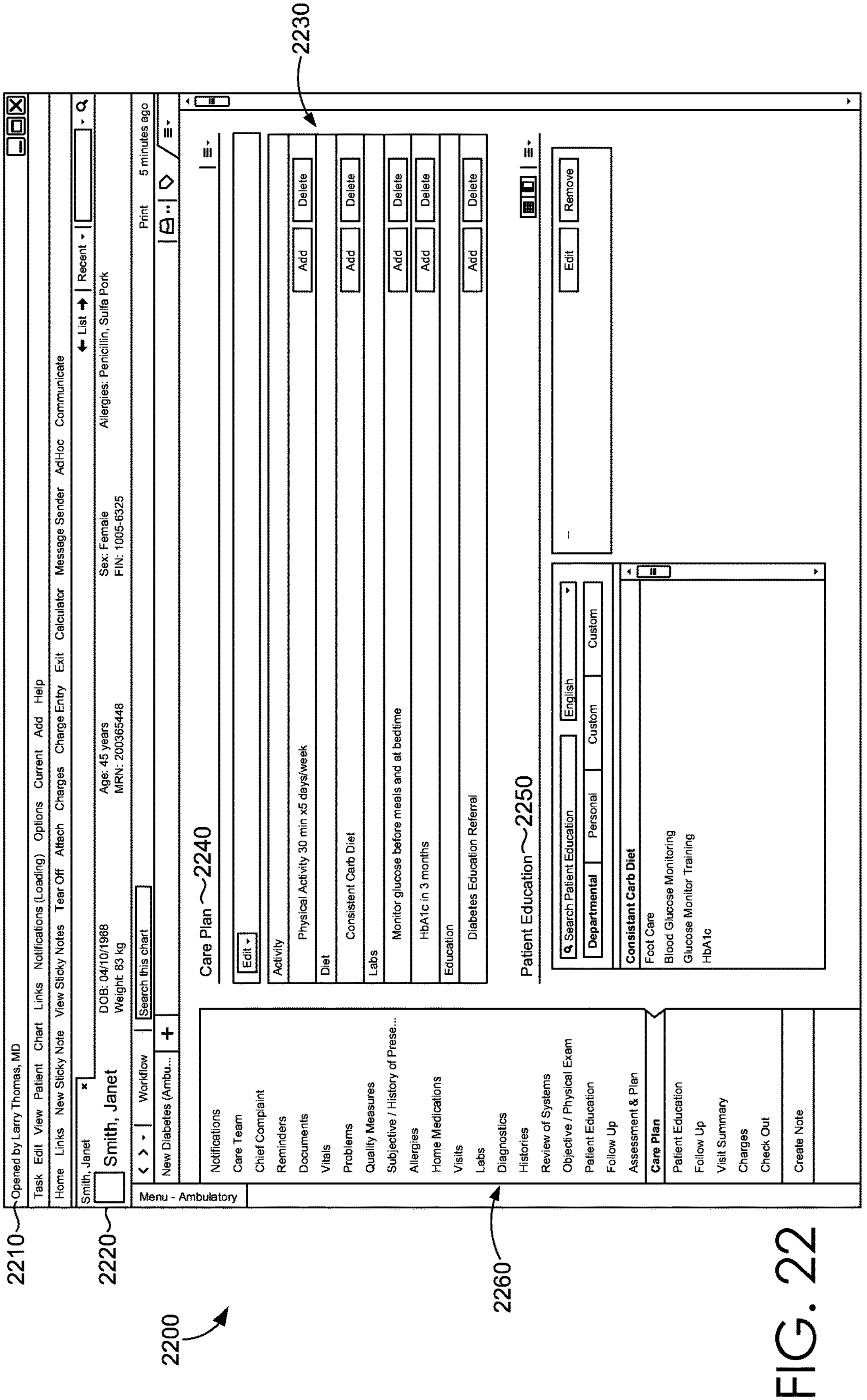

FIG. 22 depicts a patient workflow interface 2200 for a healthcare provider, e.g., the healthcare provider 2210. The patient workflow interface 2200 can include a patient information area 2220, a main area 2230, and a navigation area 2260. The patient information area 2220 may include pertinent patient information for a healthcare provider 2210 for recommending care to the patient, such as age, weight, and/or prescription allergies.

In certain embodiments, the navigation area 2260 can include a list of categories of information associated with the patient from which the healthcare provider 2210 may interact with to view additional information or take additional actions.

In one or more embodiments, the main area 2230 can include additional information related to one or more of the categories from the navigation area 2260 chosen by the healthcare provider 2210. In the embodiment depicted in FIG. 22, the main area 2230 can include a care plan recommendation interface 2240 and a patient education interface 2250. In certain embodiments, the care plan recommendation interface 2240 can be configured to provide care recommendations for one or more medial conditions. In such embodiments, the healthcare provider 2210 can have the option to add and/or remove care recommendations for the one or more medical conditions. In various embodiments, the patient education interface 2250 can be configured to allow a healthcare provider 2210 to search a patient education database and/or select patient education programs recommended for the patient.

FIG. 23 depicts a patient management interface 2300 for a healthcare provider, e.g., the healthcare provider 2310. In embodiments, the patient management interface 2300 can provide at least a portion of patient information associated with the patients that are under the care of the healthcare provider 2310. In one or more embodiments, the patient management interface 2300 may be generated, at least in part, by one or more components of a population health server, such as the population health server 250 discussed above with reference to FIG. 2.

In certain embodiments, the patient management interface 2300 can be configured to organize at least a portion of the patient information associated with the healthcare provider 2310 into multiple formats. For example, the patient management interface 2300 can include viewing tab options 2320 for the healthcare provider 2310 to choose when viewing the patient information. In the embodiment depicted in FIG. 23, the dashboard viewing option 2322 is selected. In the dashboard view, the patient management interface 2300, in certain embodiments, can include a patient population area 2330, a communications area 2340, and a categorical snapshot area 2360.

In certain embodiments, the patient population area 2330 can provide one or more metrics associated with the population of patients under the care of the healthcare provider 2310. For example, in the embodiment depicted in FIG. 23, the patient population area 2330 can include information related to the proportion of patients 2332 that are high risk, which may be presented in a graphical format. In the same or alternative embodiments, the patient population area 2330 can include a list 2334 of the top five chronic conditions among the population of patients under the care of the healthcare provider 2310 and/or a list of the persons or patients of interest 2336.

In one or more embodiments, the communications area 2340 can include a list of announcements 2342 and/or notifications 2344 for the healthcare provider 2310 in relation to the population of patients and/or in relation to the health system associated with the healthcare provider 2310.

In various embodiments, the categorical snapshot area 2360 may include tiles, e.g., the tiles 2362, 2364, and 2366, which can each provide a brief overview of the patient information organized in the various categories associated with the viewing tab options 2320. For example, in embodiments, the tile 2366 may include a brief overview of select information relating to medications.

Figure 24:
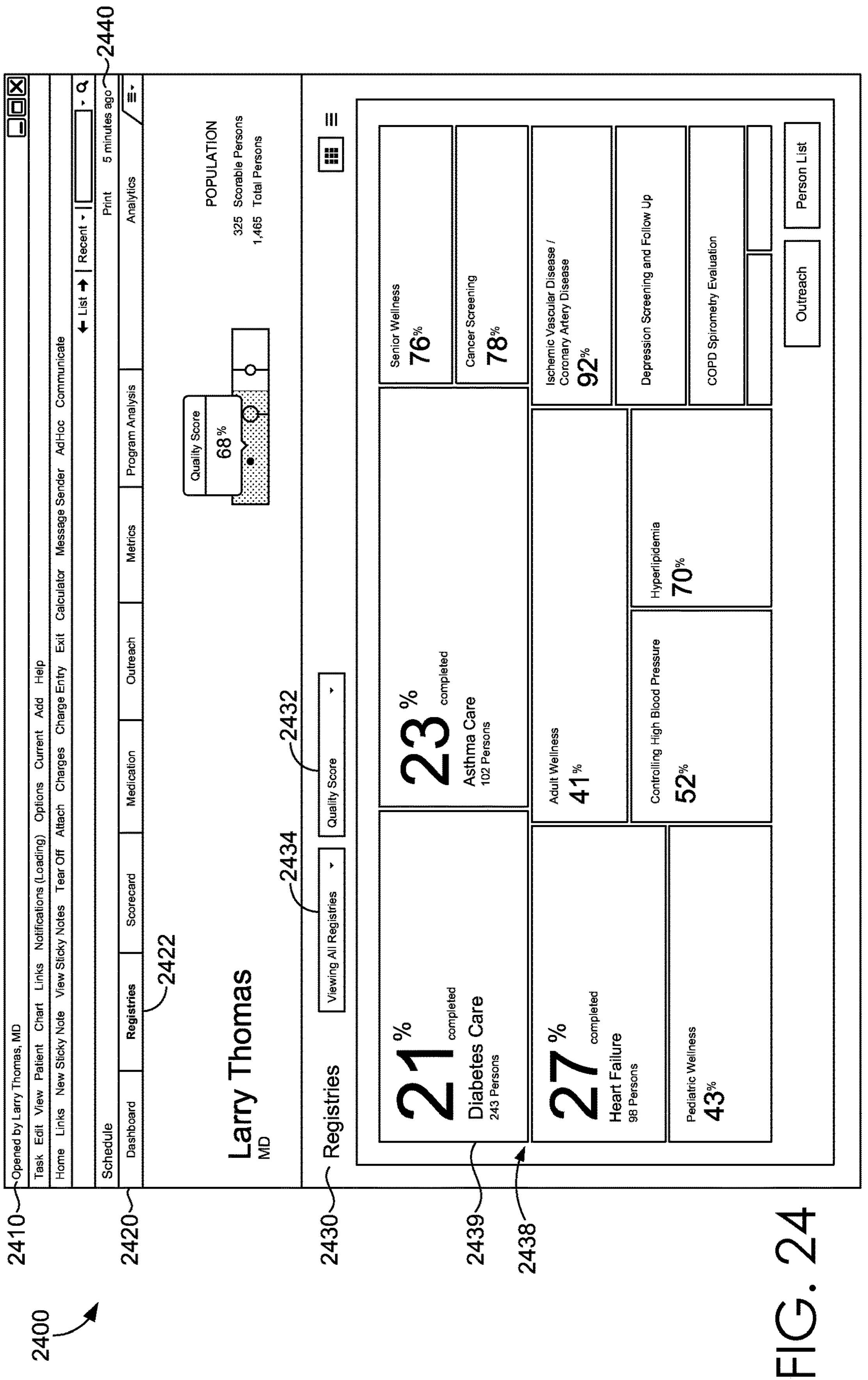

FIG. 24 depicts a patient management interface 2400 for a particular healthcare provider, e.g., the healthcare provider 2410. In embodiments, the patient management interface 2400 can provide at least a portion of patient information associated with the patients that are under the care of the healthcare provider 2410. In one or more embodiments, the patient management interface 2400 may be generated, at least in part, by one or more components of a population health server, such as the population health server 250 discussed above with reference to FIG. 2.

In certain embodiments, the patient management interface 2400 can be configured to organize at least a portion of the patient information associated with the healthcare provider 2410 in multiple formats. For example, the patient management interface 2400 can include viewing tab options 2420 for the healthcare provider 2410 to choose when viewing the patient information. In the embodiment depicted in FIG. 24, the registries viewing option 2422 is selected. In the registries viewing option 2422, the patient management interface 2400, in certain embodiments, can include a registry information interface 2430.

The registry information interface 2430 may include a depiction of various metrics for at least a portion of the registries associated with the population patients under the care of the healthcare provider 2410. For example, in the embodiment depicted in FIG. 24, the registry information interface 2430 can include a plurality of tiles 2438 which can depict what percentage of patients have received care associated with that registry. For example, as depicted in the tile 2439, 21% of the patients have received care related to their presence in the diabetes registry.

In certain embodiments, the registry information interface 2430 can be configured to provide the healthcare provider 2410 various viewing options for the registries. For instance, in such embodiments, the registry information interface 2430 can include a viewing option 2434 for viewing all registries or a specific registry. In the same or alternative embodiments, the registry information interface 2430 can include a viewing option 2432 for viewing specific information about the registries that are chosen for viewing, such as a quality score. In one embodiment, a quality score can depict the percentage of patients that have received care or a consultation with respect the condition associated with a particular registry and/or the percentage of patients that have received care or a consultation with respect a particular treatment associated with a particular population of patients in a particular registry.

In one or more embodiments, the patient management interface 2400 can include near real-time data that is supplied from a population health management system, such as the population health management system 200 discussed above with respect to FIG. 2. In such embodiments, the patient management interface 2400 may include an update indicator 2440 so that the healthcare provider 2410 can be aware how current the information is. As used herein, near real-time data can mean data that is available for viewing or processing by one or more components of a population health management system, such as the population health management system 200 discussed above with respect to FIG. 2, within at least about 1 minute, 10 minutes, 30 minutes, 60 minutes, 120 minutes, 240 minutes, or 480 minutes of being input into any component or portion of such a population health management system.

Figure 25:
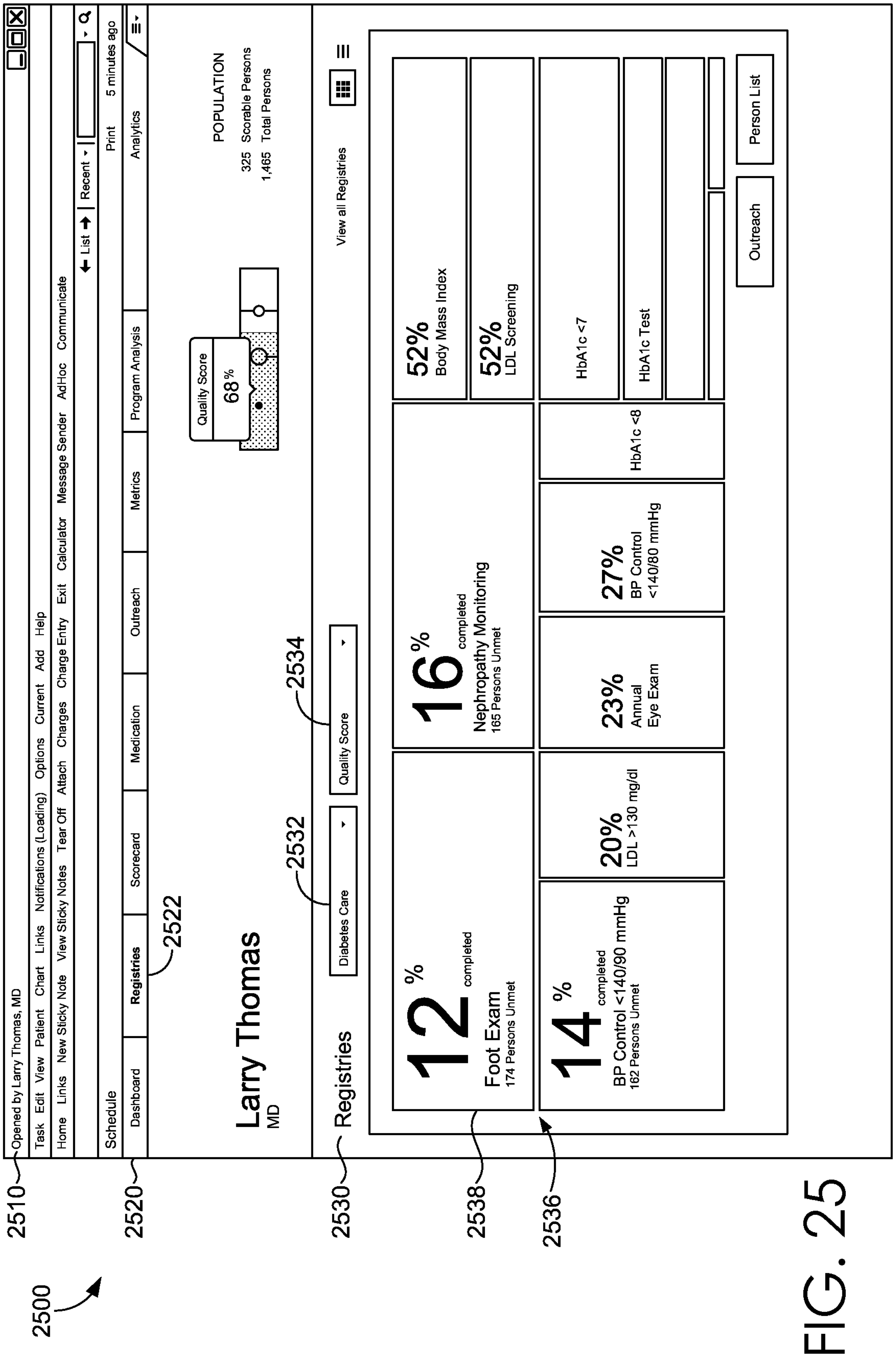

FIG. 25 depicts a patient management interface 2500 for a particular healthcare provider, e.g., the healthcare provider 2510. In embodiments, the patient management interface 2500 can provide at least a portion of patient information associated with the patients that are under the care of the healthcare provider 2510. In one or more embodiments, the patient management interface 2500 may be generated, at least in part, by one or more components of a population health server, such as the population health server 250 discussed above with reference to FIG. 2.

In certain embodiments, the patient management interface 2500 can organize at least a portion of the patient information associated with the healthcare provider 2510 in multiple formats. Further, in such embodiments, the patient management interface 2500 can include viewing tab options 2520 for the healthcare provider 2510 to choose when viewing the patient information. In the embodiment depicted in FIG. 25, the registries viewing option 2522 is selected. In the registries viewing option 2522, the patient management interface 2500, in certain embodiments, can include a registry information interface 2530.

Like the registry information interface 2430 discussed above with reference to FIG. 24, the registry information interface 2530 can provide the healthcare provider 2510 various viewing options for the registries. For instance, the registry information interface 2530 may include a viewing option 2532 for viewing all registries or a specific registry and/or a viewing option 2534 for viewing specific information about the registries that are chosen for viewing, such as a quality score. In the embodiment depicted in FIG. 25, the specific registry of diabetes care and the associated quality score were selected.

Further, like the registry information interface 2430 of FIG. 24, the registry information interface 2530 may include a depiction of various metrics for at least a portion of the population of patients in the diabetes care registry that are under the care of the healthcare provider 2510. For example, in the embodiment depicted in FIG. 25, the registry information interface 2530 can include a plurality of tiles 2536 which can depict what percentage of patients have received care for various treatment aspects associated with diabetes care. For example, as depicted in the tile 2538, 12% of these patients have received a foot exam.

Figure 26:
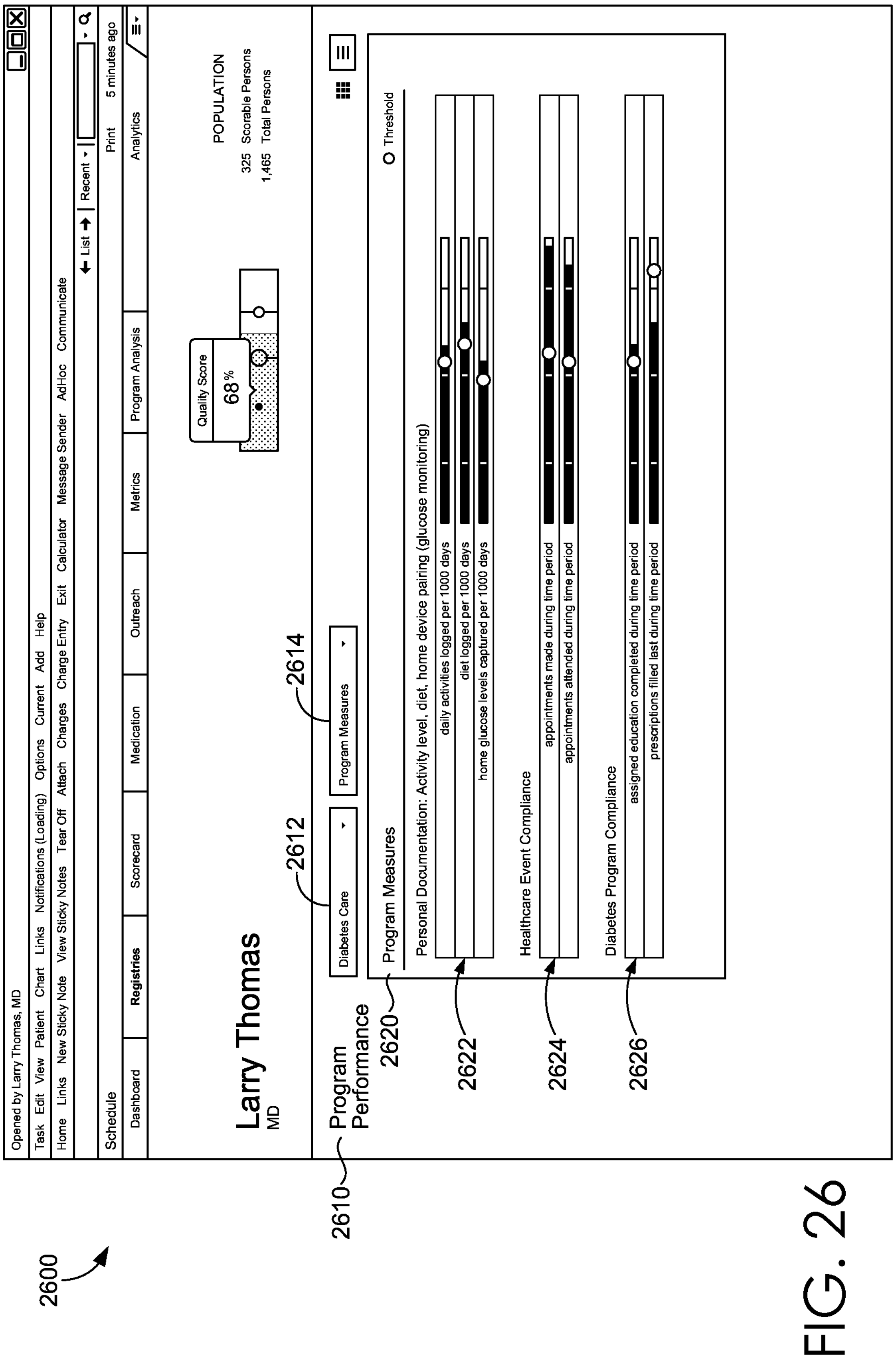

The patient management interface 2600 depicted in FIG. 26 is similar to the patient management interface 2500 discussed above with respect to FIG. 25, with the exception that the program measures viewing option 2614 was selected along with the diabetes care registry 2612 to populate the registry information interface 2610.

In the embodiment depicted in FIG. 26, the registry information interface can include a list 2620 of various program measures and may further include a graphical representation of the compliance level associated with those measures. For instance, as seen in the embodiment depicted in FIG. 26, the list 2620 can include personal patient documentation measure indicators 2622, healthcare event compliance measure indicators 2624, and/or diabetes program compliance measure indicators 2626.

Figure 27:
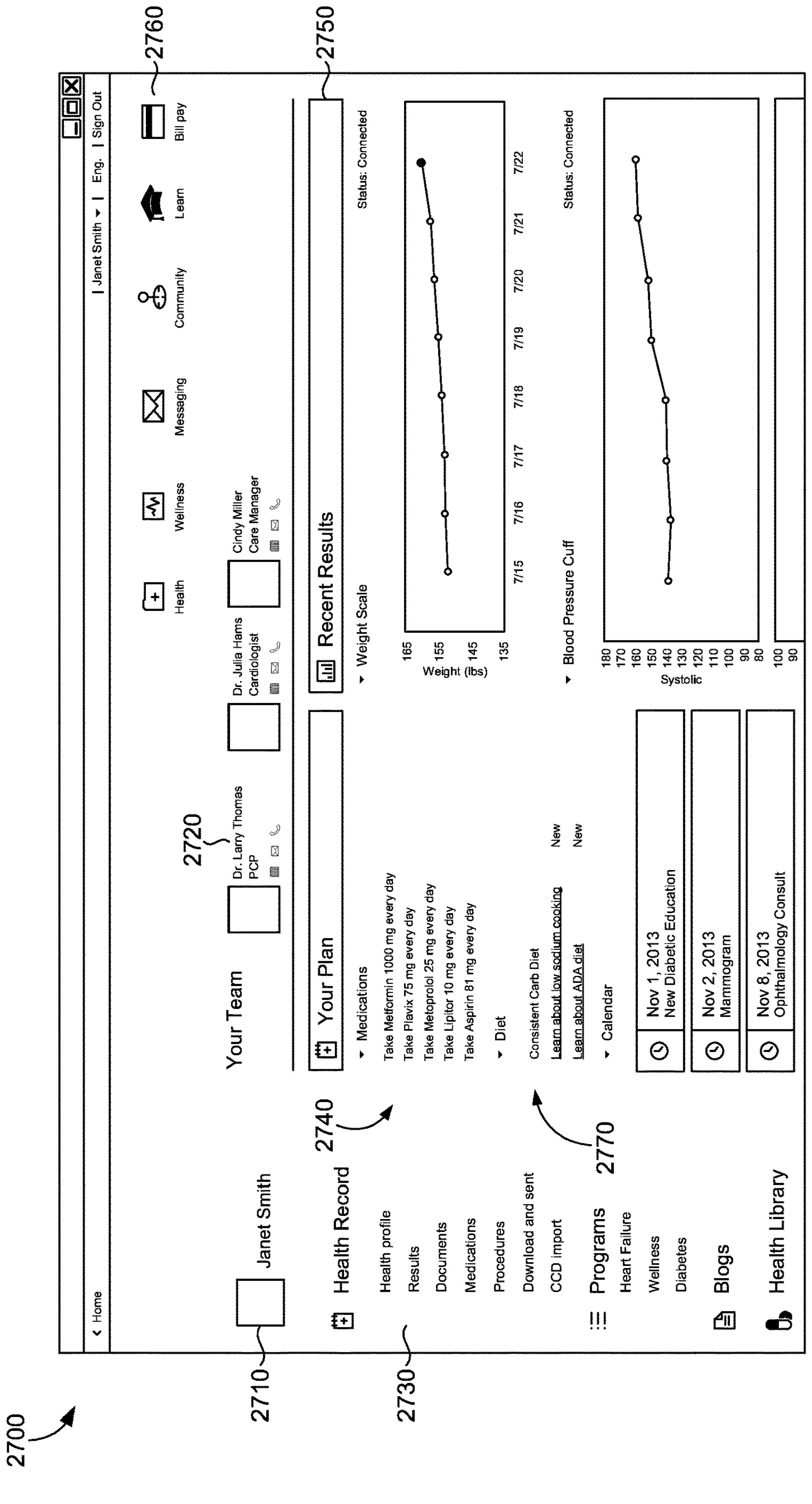

FIG. 27 depicts a patient interface 2700 where a patient, e.g., the patient 2710, may view and interact with information associated with any or all care programs associated with the patient's various medical conditions. In certain embodiments, the patient interface 2700 may include a list 2720 of associated healthcare providers, a navigation panel 2730, a main view area 2740, and a communication interface area 2760.

In certain embodiments, the navigation panel 2730 may include a list of various categories of information of which the patient 2710 may choose to view in the main view area 2740 and/or to open new windows for additional information associated with a particular category.

In the embodiment depicted in FIG. 27, the main view area 2740 can include a plan view area 2770, which may display various aspects of one or more care plans assigned to the patient 2710, such as medication, diet, and/or appointments. In the same or alternative embodiments, the main view area 2740 can include a recent results area 2750 that can display one or more results or data from a medical device, such as a weight scale or a blood pressure monitor.

In one or more embodiments, the communication interface area 2760 may be configured to allow the patient to contact or engage a number of various groups. For example, in such embodiments, the communication interface 2760 may include links so that the patient 2710 can contact or message one or more healthcare providers, contact or message a particular community of patients, pay a medical bill, or obtain additional wellness information.

Figure 28:
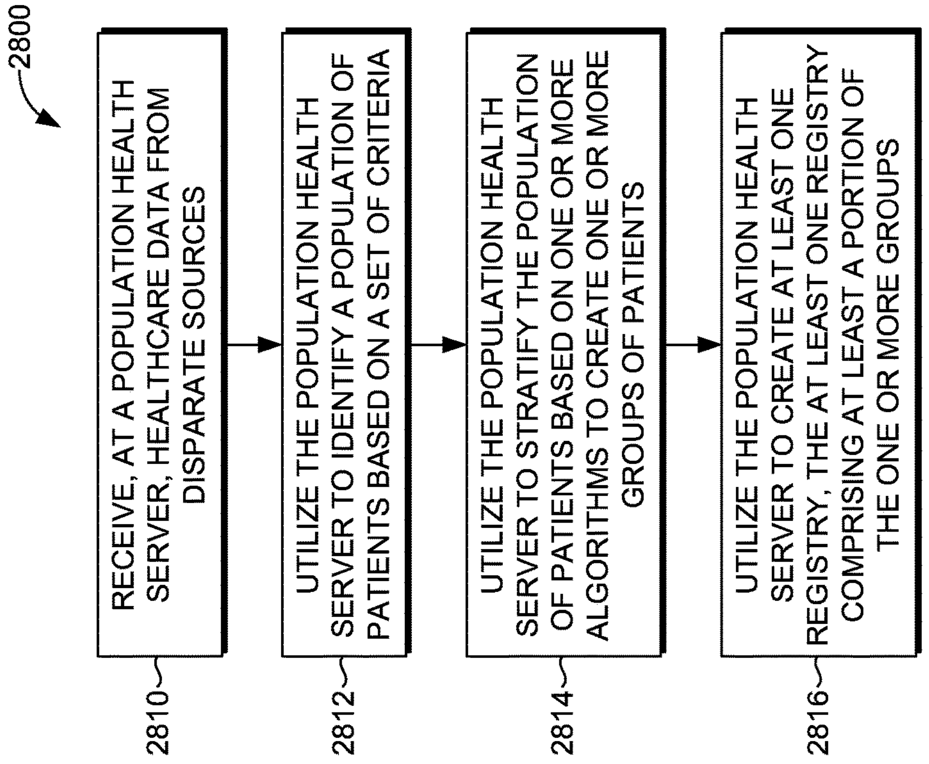
FIG. 28 is a flow diagram illustrating an exemplary method that facilitates designing and utilizing population health programs, in accordance with embodiments of the present invention.

FIG. 28 depicts an exemplary flow diagram for a method 2800 that facilitates designing and utilizing population health programs. Initially, at step, 2810 healthcare data from disparate sources can be received by a population health server. In one embodiments, the step 2810 may be performed at least partly by the receiving component 252 discussed above with reference to FIG. 2. In embodiments, the healthcare data may include any or all of the properties of the healthcare data discussed above with reference to the EMRs 212 of FIG. 2. In step 2812, the population health server can be utilized to identify a population of patients based on a set of criteria. In certain embodiments, the step 2812 may be performed at least partly by the identifying component 254 discussed above with reference to FIG. 2. In step 2814, the population health server can utilized to stratify the population of patients based on one or more algorithms to create one or more groups of patients. In certain embodiments, the step 2814 may be at least partly performed by the stratifying component 256 discussed above with reference to FIG. 2. In step 2816, the population health server can be utilized to create at least one registry, the at least one registry comprising at least a portion of the one or more groups. In one embodiment, the step 2816 may be performed at least partly by the creating component 258 discussed above with reference to FIG. 2. In one embodiment, the population health server of steps 2810, 2812, 2814, and/or 2816 can have any or all of the properties of the population health server 250 discussed above with reference to FIG. 2.

Figure 29:
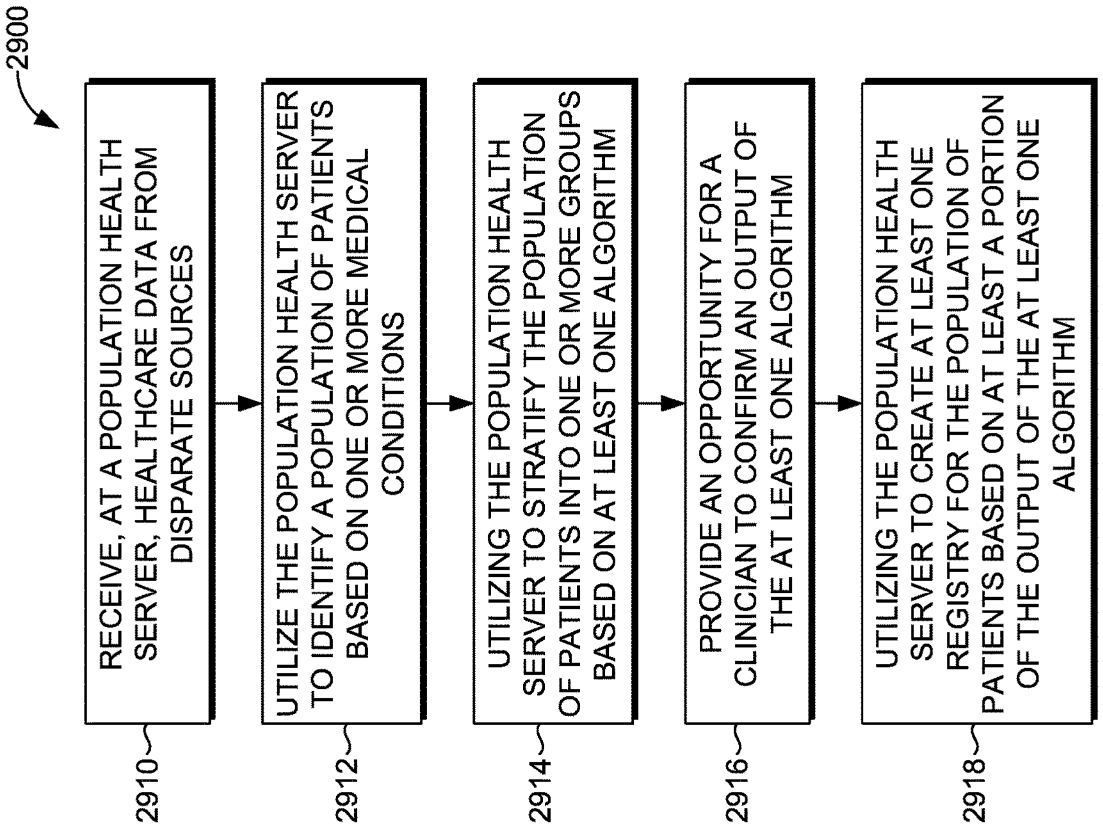
FIG. 29 is a flow diagram illustrating an exemplary method that facilitates designing and utilizing population health programs, in accordance with embodiments of the present invention.

FIG. 29 depicts an exemplary flow diagram for a method 2900 that facilitates designing and utilizing population health programs. In step 2910, healthcare data from disparate sources can be received by a population health server. In one embodiments, the step 2910 may be performed at least partly by the receiving component 252 discussed above with reference to FIG. 2. In embodiments, the healthcare data may include any or all of the properties of the healthcare data discussed above with reference to the EMRs 212 of FIG. 2. In step 2912, the population health server can be utilized to identify a population of patients based on one or more medical conditions. In certain embodiments, the step 2912 may be performed at least partly by the identifying component 254 discussed above with reference to FIG. 2. In step 2914, the population health server can be utilized to stratify the population of patients into one or more groups based on at least one algorithm. In certain embodiments, the step 2914 may be at least partly performed by the stratifying component 256 discussed above with reference to FIG. 2. In step 2916, an opportunity for a clinician to confirm an output of the at least one algorithm can be provided. In one embodiment, the step 2916 may be performed at least partly by the output component 260 discussed above with reference to FIG. 2. In step 2918, the population health server can be utilized to create at least one registry for the population of patients based on at least a portion of the output of the at least one algorithm. In one embodiment, the population health server of steps 2910, 2912, 2914, and/or 2918 can have any or all of the properties of the population health server 250 discussed above with reference to FIG. 2.

Figure 30:
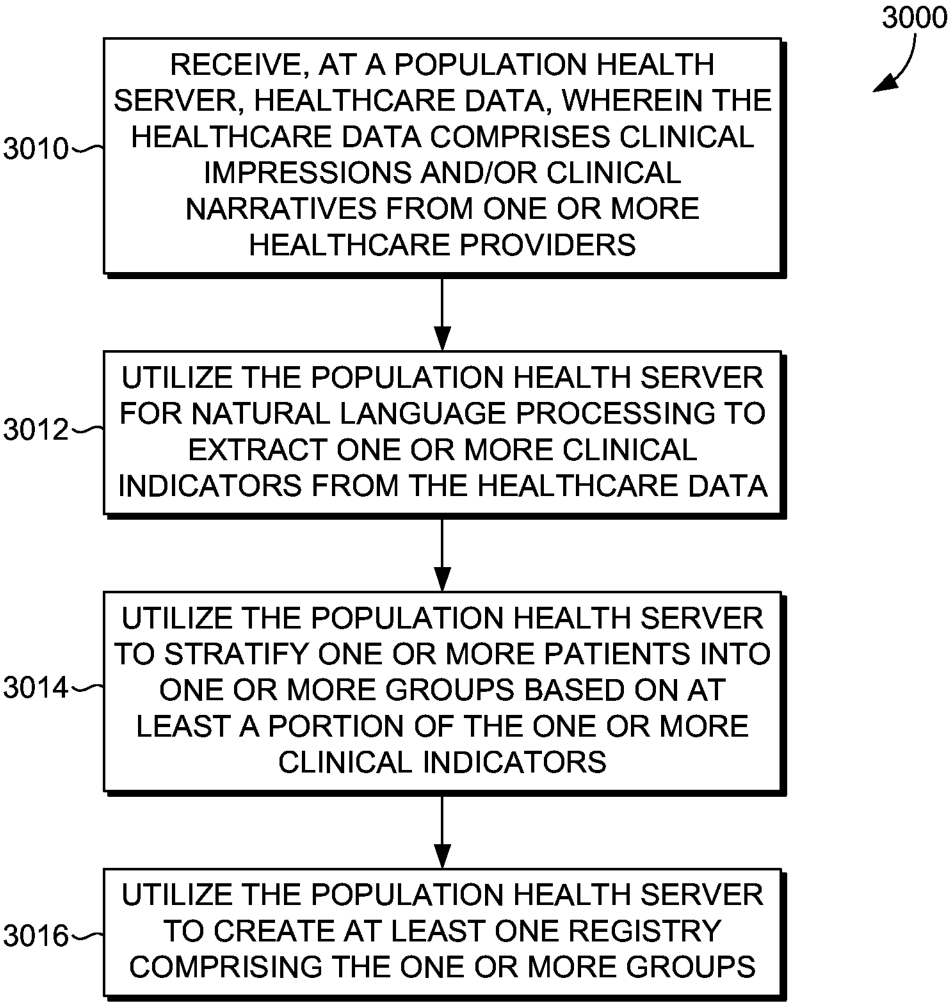
FIG. 30 is a flow diagram illustrating an exemplary method for stratifying one or more patients into one or more groups, in accordance with embodiments of the present invention.

FIG. 30 depicts an exemplary flow diagram for a method 3000 for stratifying one or more patients into one or more groups. In step 3010, healthcare data can be received by a population health server. The healthcare data may include clinical impressions and/or clinical narratives from one or more healthcare providers. In embodiments, the healthcare data may include any or all of the properties of the healthcare data discussed above with reference to the EMRs 212 of FIG. 2. In one embodiment, the step 3010 may be performed at least partly by the receiving component 252 discussed above with reference to FIG. 2. In step 3012, the population health server can be utilized for natural language processing to extract one or more clinical indicators from the healthcare data. In certain embodiments, the step 3012 may be at least partly performed by the natural language processing component 270 discussed above with reference to FIG. 2. In step 3014, the population health server can be utilized to stratify one or more patients into one or more groups based on at least a portion of the one or more clinical indicators. In one embodiments, the step 3014 may be at least partly performed by the stratifying component 256 discussed above with reference to FIG. 2. In step 3016, the population health server can be utilized to create at least one registry comprising the one or more groups. The at least one registry may account for one or more of: resources available to a patient; lifestyle and prognostic assets that can be used for prediction; and assets necessary for attribution, allocation, or measurement. In certain embodiments, the step 3016 may be at least partly performed by the creating component 258 discussed above with reference to FIG. 2. In one embodiment, the population health server of steps 3010, 3012, 3014, and/or 3016 can have any or all of the properties of the population health server 250 discussed above with reference to FIG. 2.

Figure 31:
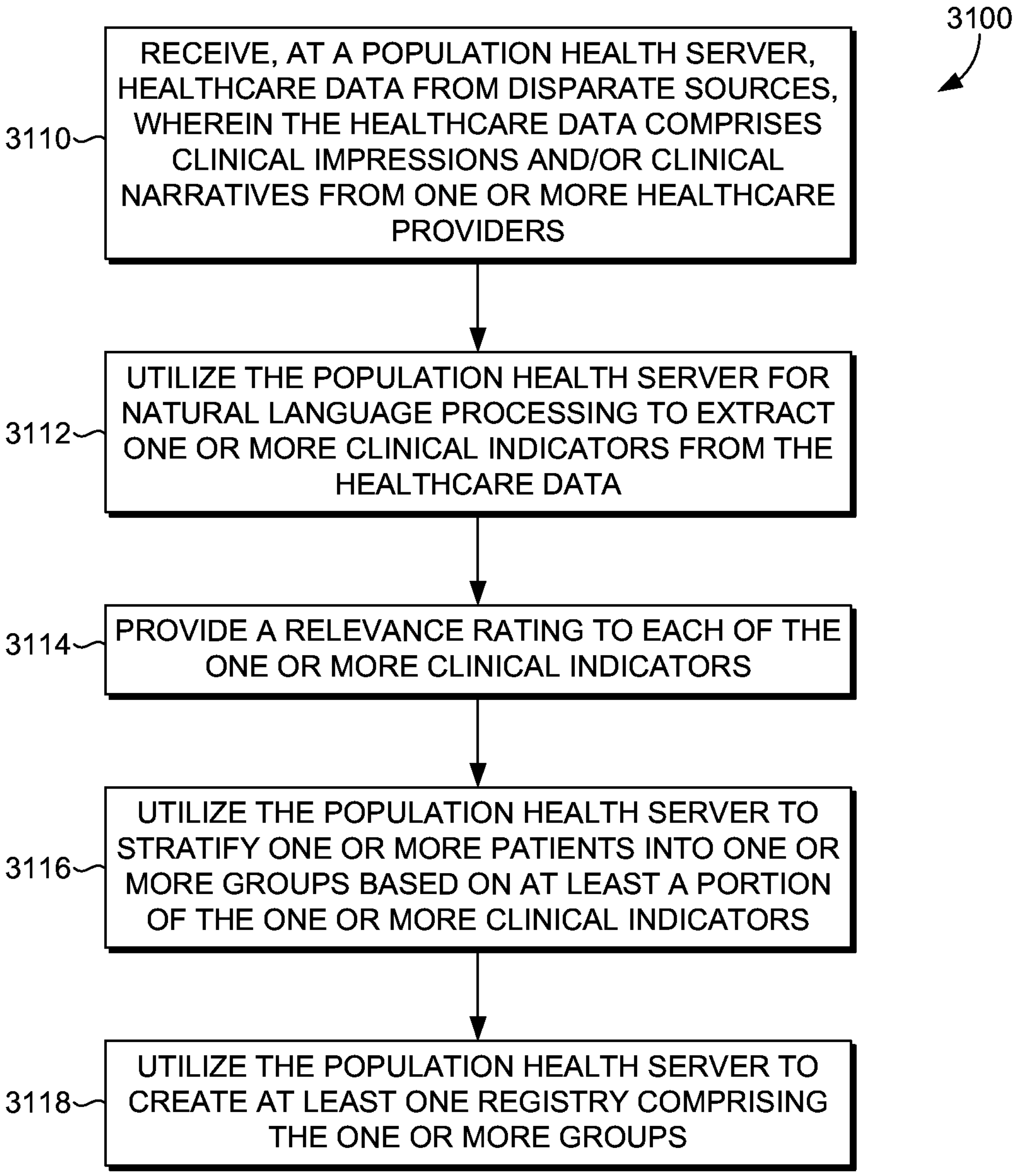
FIG. 31 is a flow diagram illustrating an exemplary method for stratifying one or more patients into one or more groups, in accordance with embodiments of the present invention.

FIG. 31 depicts an exemplary flow diagram for a method 3100 for stratifying one or more patients into one or more groups. In step 3110, healthcare data from disparate sources can be received by a population health server. The healthcare data may comprise clinical impressions and/or clinical narratives from one or more healthcare providers. In one embodiment, the step 3110 may be performed at least partly by the receiving component 252 discussed above with reference to FIG. 2. In embodiments, the healthcare data may include any or all of the properties of the healthcare data discussed above with reference to the EMRs 212 of FIG. 2. In step 3112, the population health server can be utilized for natural language processing to extract one or more clinical indicators from the healthcare data, where the one or more clinical indicators are associated with one or more chronic conditions. In certain embodiments, the step 3112 may be at least partly performed by the natural language processing component 270 discussed above with reference to FIG. 2. In step 3114, a relevance rating can be provided to each of the one or more clinical indicators. In one embodiments, the step 3114 may be at least partly performed by the natural language processing component 270 discussed above with reference to FIG. 2. In step 3116, the population health server can be utilized to stratify one or more patients into one or more groups based on at least a portion of the one or more clinical indicators. In one embodiment, the step 3116 may be at least partly performed by the stratifying component 256 discussed above with reference to FIG. 2. In step 3118, the population health server can be utilized to create at least one registry comprising the one or more groups. The at least one registry may account for one or more of: resources available to a patient; lifestyle and prognostic assets that can be used for prediction; and assets necessary for attribution, allocation, or measurement. In certain embodiments, the step 3118 may be at least partly performed by the creating component 258 discussed above with reference to FIG. 2. In one embodiment, the population health server of steps 3110, 3112, 3116, and/or 3118 can have any or all of the properties of the population health server 250 discussed above with reference to FIG. 2.

Figure 32:
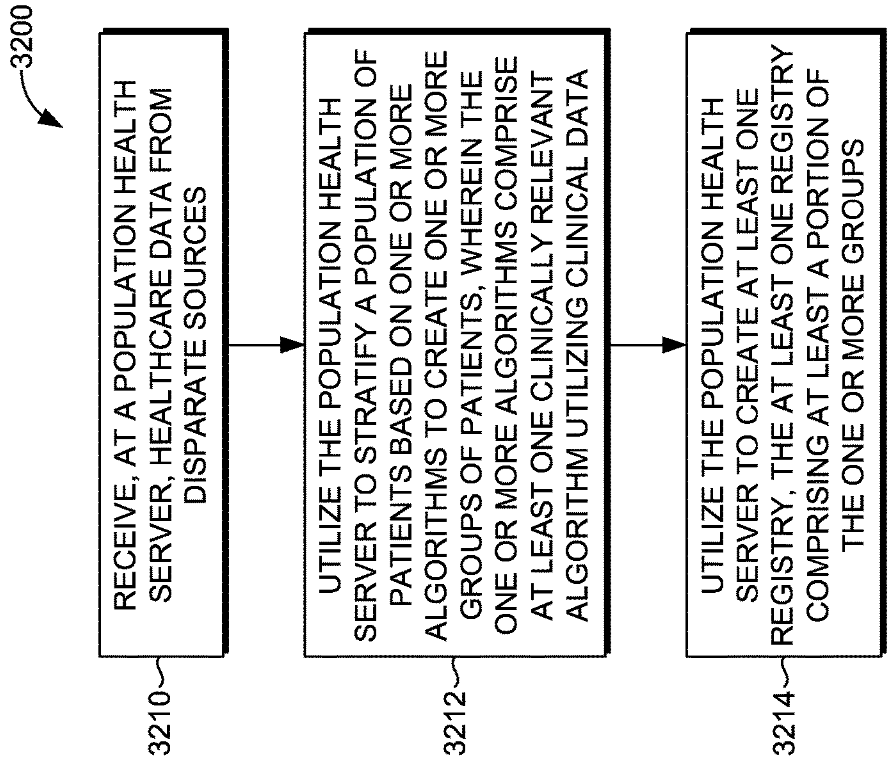
FIG. 32 is a flow diagram illustrating an exemplary method for facilitating the use of at least one clinically relevant algorithm in population health programs, in accordance with embodiments of the present invention.

FIG. 32 depicts an exemplary flow diagram for a method 3200 that facilitates using at least one clinically relevant algorithm in population health programs. In step 3210, healthcare data from disparate sources can be received by a population health server. In one embodiment, the step 3210 may be performed at least partly by the receiving component 252 discussed above with reference to FIG. 2. In embodiments, the healthcare data may include any or all of the properties of the healthcare data discussed above with reference to the EMRs 212 of FIG. 2. In step 3212, the population health server can be utilized to stratify a population of patients based on one or more algorithms to create one or more groups of patients, where the one or more algorithms comprise at least one clinically relevant algorithm utilizing clinical data. In one or more embodiments, the clinical data can have any or all of the properties of the clinical data discussed above with reference to the EMRs 212 of FIG. 2. In certain embodiments, the step 3212 may be performed at least partly by the stratifying component 256 discussed above with reference to FIG. 2. In step 3214, the population health server can be utilized to create at least one registry, the at least one registry comprising at least a portion of the one or more groups. In one embodiment, the step 3214 may be at least partly performed by the creating component 258 discussed above with reference to FIG. 2. In one embodiment, the population health server of steps 3210, 3212, and/or 3214 can have any or all of the properties of the population health server 250 discussed above with reference to FIG. 2.

Figure 33:
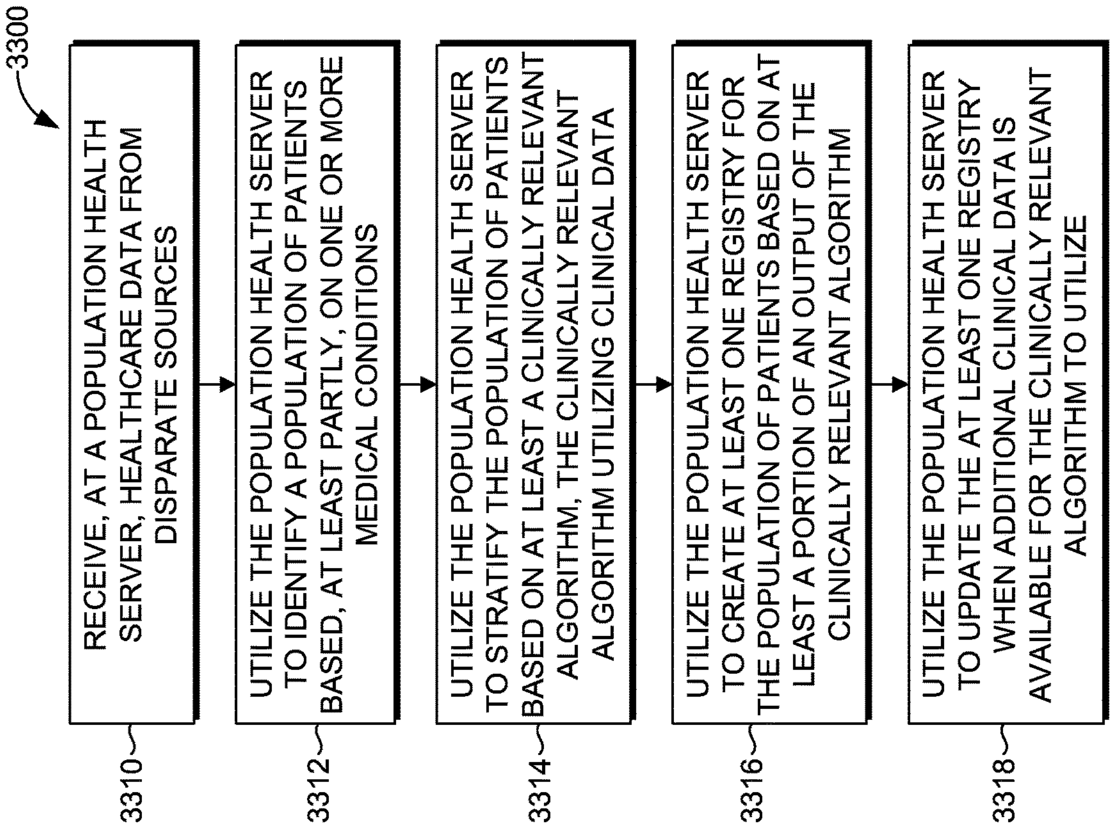
FIG. 33 is a flow diagram illustrating an exemplary method for facilitating the use of clinically relevant algorithms for registry population, in accordance with embodiments of the present invention.

FIG. 33 depicts an exemplary flow diagram for a method 3300 that facilitates utilizing clinically relevant algorithms for registry population. In step 3310, healthcare data from disparate sources can be received by a population health server. In one embodiment, the step 3310 may be performed at least partly by the receiving component 252 discussed above with reference to FIG. 2. In embodiments, the healthcare data may include any or all of the properties of the healthcare data discussed above with reference to the EMRs 212 of FIG. 2. In step 3312, the population health server can be utilized to identify a population of patients based, at least partly, on one or more medical conditions. In one embodiment, the step 3312 may be at least partly performed by the identifying component 254 discussed above with reference to FIG. 2. In step 3314, the population health server can be utilized to stratify the population of patients based on at least a clinically relevant algorithm, the clinically relevant algorithm utilizing clinical data. The clinical data including one or more of medication information, laboratory values, diagnostics, clinician narratives, and clinician assessments. In one or more embodiments, the clinical data can have any or all of the properties of the clinical data discussed above with reference to the EMRs 212 of FIG. 2. In certain embodiments, the step 3314 may be performed at least partly by the stratifying component 256 discussed above with reference to FIG. 2. In step 3316, the population health server can be utilized to create at least one registry for the population of patients based on at least a portion of an output of the clinically relevant algorithm. In one embodiment, the step 3316 may be at least partly performed by the creating component 258 discussed above with reference to FIG. 2. In step 3318, the population health server can be utilized to update the at least one registry when additional clinical data is available for the clinically relevant algorithm to utilize. In one embodiment, the step 3318 is at least partly performed by the receiving component 252, the stratifying component 256, and/or the creating component 258 discussed above with reference to FIG. 2. In one embodiment, the population health server of steps 3310, 3312, 3314, 3316, and/or 3318 can have any or all of the properties of the population health server 250 discussed above with reference to FIG. 2.

Figure 34:
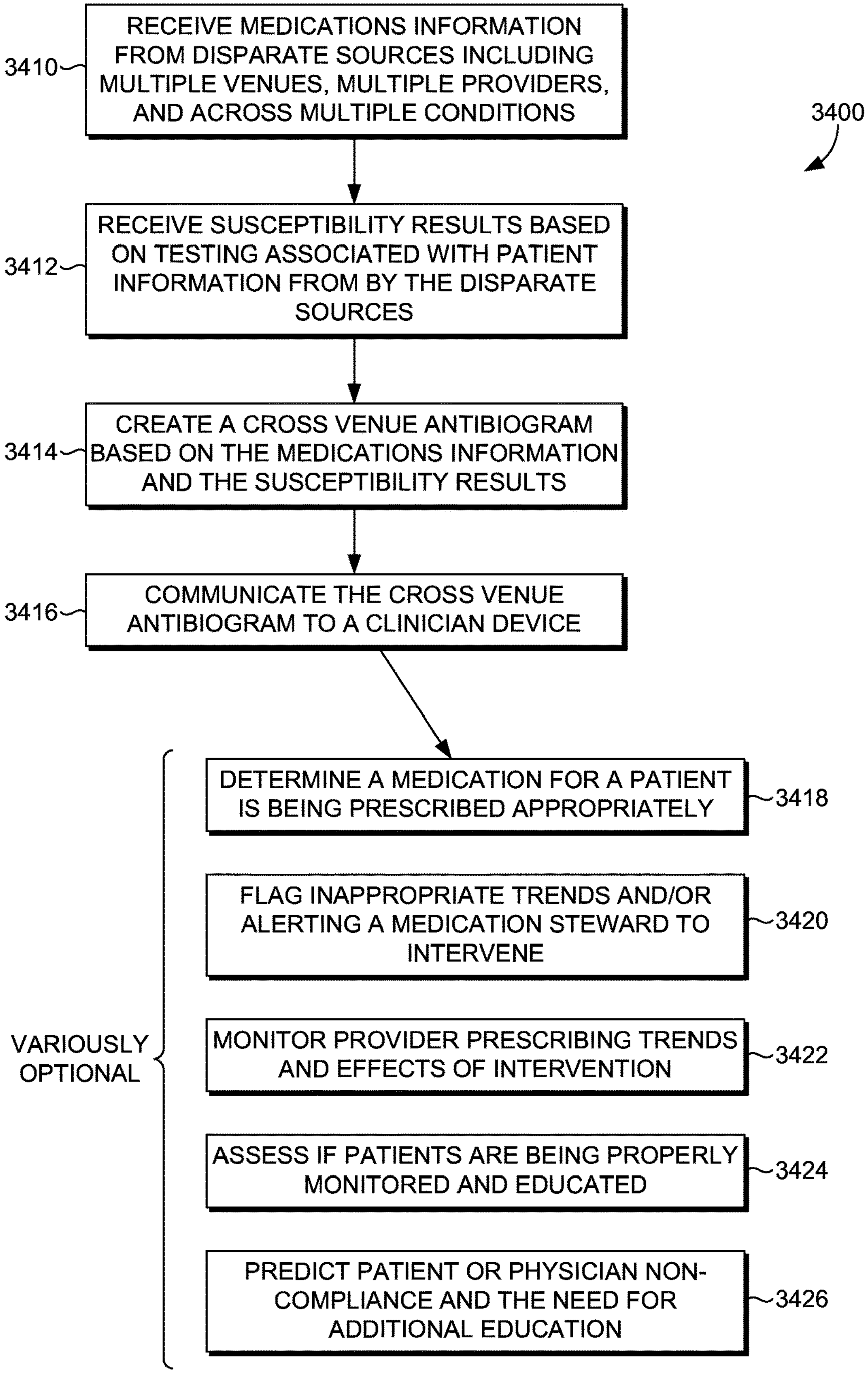
FIG. 34 is a flow diagram illustrating an exemplary method for providing a cross venue antibiogram, in accordance with embodiments of the present invention.

Referring now to FIG. 34, an exemplary flow diagram is depicted of a method 3400 of providing a cross venue antibiogram. Initially, at step 3410, medications information is received from disparate sources. The disparate sources may include multiple venues, multiple providers, and across multiple conditions (e.g., from more than one registry identifying more than one condition). Susceptibility results based on testing associated with patient information are received, at step 3412, from the disparate sources. The susceptibility results may include results from testing being performed on inpatients, outpatients, and patients within the community outside of a hospital setting (e.g., non-acute care settings). The susceptibility results may include patient demographics but does not include patient identifiers.

A cross venue antibiogram is created, at step 3414, based on the medications information and the susceptibility results. At step 3416, the cross venue antibiogram is communicated to a clinician device. The cross venue antibiogram allows the clinician to more accurately prescribe medications by providing information as to which medications will be most effective based on the patients circumstances and location or setting and provides a broad view of susceptibility result trends. In embodiments, one or more populations can be monitored, based on the cross venue antibiogram, for development of antimicrobial resistance, unnecessary prescriptions, incorrect or more costly medications, neglecting to order follow up labs to monitor for adverse drug reactions, patients not refilling medications as prescribed, drug interactions for patients using multiple pharmacies and/or providers.

In one embodiment, filtering of the antibiogram is enabled based on selected demographics. In this regard, a clinician can filter the antibiogram based on circumstances relevant to the patient to create a patient-specific antibiogram. The demographics may include an institution, a practice associated with a clinician, a zip code, a county, a city, a state, a region, or a country. A specific disease state may be selected for a patient or received from one or more data sources. Patient information including related conditions, laboratory results, and allergy information for the patient may additionally be received from one or more data sources. Multiple medication options for the patient may be provided based on the received information and the patient-specific antibiogram. The medication options may include dosing, generic alternatives, cost, availability, and susceptibility information, the cost including relative cost, actual wholesale price, institution cost, patient cost, or cost effectiveness, and/or the availability including a numerical amount or relative amount of a drug in stock.

In embodiments, the cross venue antibiogram can be further utilized to determine a medication for a patient is being prescribed appropriately, as shown at step 3418. For example, information from a data source may indicate the patient was prescribed a medication that is ineffective given the patient's condition or particular location. Similarly, the information may indicate a different medication is more effective. In these examples, it is determined that the medication is not being prescribed appropriately. In a situation where the information indicates the medication is the most effective given the patient's condition or particular location, it is determined that the mediation is being prescribed appropriately. In an embodiment, if it is determined that the medication is not being prescribed appropriately, inappropriate trends (i.e., the medication is not being prescribed appropriately) may be flagged at step 3420. Additionally or alternatively, a medication steward may be alerted to intervene. Inappropriate trends and/or interventions may be documented via an automated messaging system. Similarly, in one embodiment, interventions may be electronically captured for trending and reporting. Provider prescribing trends and effects of intervention may be monitored, at step 3422.

In embodiments, information from a data source may indicate the patient was prescribed a medication that requires a particular form of monitoring, follow-up, education, additional laboratories, and the like. Based on additional information from a data source that may indicate a requirement has or has not been fulfilled, in one embodiment, it is assessed, at step 3424, if the patient is being properly monitored and educated. In one embodiment, as shown at step 3426, patient or clinician non-compliance and the need for additional education is predicted. In one embodiment, any or all of the steps of method 2400 may be at least partly performed by one of various components of the population health server 250 discussed above with reference to FIG. 2.

Figure 35:
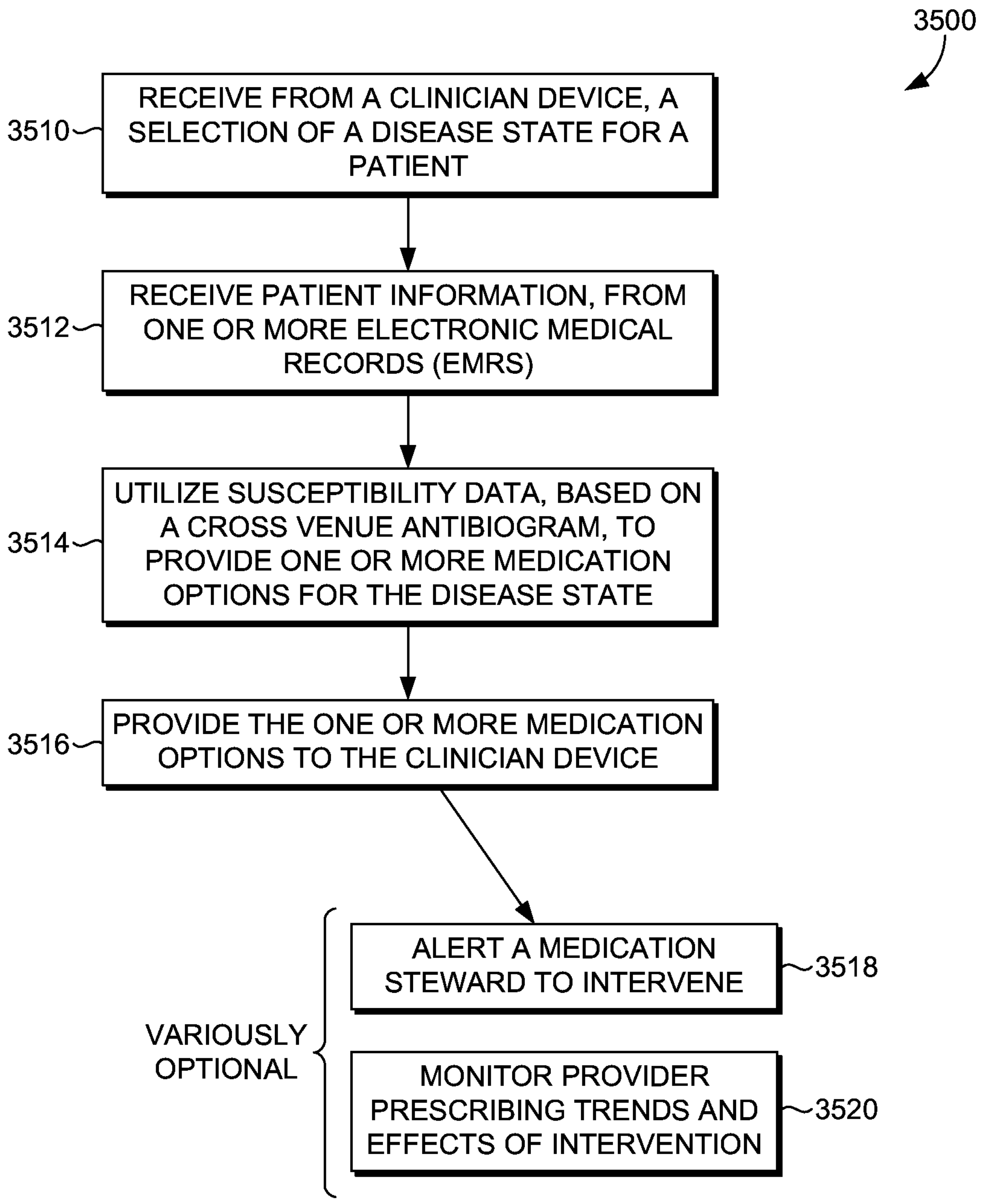
FIG. 35 is a flow diagram illustrating an exemplary method for providing a comprehensive medication advisor, in accordance with embodiments of the present invention.

Turning now to FIG. 35, an exemplary flow diagram is depicted of a method 3500 of providing a comprehensive medication advisor. Initially, at step 3510, a selection of a disease state is received from a clinician device. Patient information including related conditions, laboratory results, allergy information for the patient is received from one or more electronic medical records at step 3512. Utilizing susceptibility data, based on a cross venue antibiogram, one or more medication options are provided for the disease state, at step 3514. The medication options may include dosing, generic alternatives, cost, availability, and susceptibility information. The cost may include relative cost, actual wholesale price, institution cost, patient cost, or cost effectiveness. The availability may include a numerical amount or relative amount of a drug in stock. The susceptibility information may be based on the antibiogram and may include information relevant to one or more of the patient, an institution, a practice associated with a clinician, a zip code, a county, a city, a state, a region, or a country. The one or more medication options are provided to the clinician device, at step 3516. In one embodiment, as shown at step 3518, if a clinician prescribes a medication that is not one of the one or more medication options, a medication steward is alerted to intervene. Alternatively or additionally, prescribing trends and effects of intervention is monitored, in one embodiment, at step 3520. In one embodiment, any or all of the steps of method 3500 may be at least partly performed by one of various components of the population health server 250 discussed above with reference to FIG. 2.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer storage media storing computer-executable instructions that, when executed by one or more computing devices, cause the one or more computing devices to perform a method, the method comprising:

generating a cross-venue antibiogram that represents susceptibility of pathogens for a plurality of patients having different medical conditions, wherein the cross-venue antibiogram is generated from patient information for the plurality of patients obtained from acute and non-acute data sources that are associated with two or more independent electronic medical record (EMR) systems, wherein the acute and non-acute data sources are disparate data sources using distinct nomenclatures;

providing the disparate acute and non-acute data sources with real-time access to the cross-venue antibiogram by storing the cross-venue antibiogram on one or more cloud servers accessible by computing devices of the disparate acute and non-acute data sources, wherein the computing devices associated with the disparate acute and non-acute data sources are remote from the one or more cloud servers;

updating the cross-venue antibiogram in real time with additional patient information received from the disparate acute and non-acute data sources using the distinct nomenclatures;

receiving a selection of a specific disease state for a patient;

receiving patient-specific information for the patient including at least one of medical conditions, laboratory results, or allergy information;

creating a patient-specific antibiogram from the updated cross-venue antibiogram, wherein the patient-specific antibiogram is created using the susceptibility of pathogens represented in the updated cross-venue antibiogram for those of the plurality of patients that share the specific disease state of the patient;

providing a medication option for the patient based on the patient-specific antibiogram, the medication option including at least one of dosing, generic alternatives, cost, availability, or susceptibility information; and presenting a patient-specific preview of the patient-specific antibiogram on a user interface of a clinician device, the patient-specific preview consolidating the patient information for the plurality of patients obtained from the disparate acute and non-acute data sources that are associated with the two or more independent electronic medical record (EMR) systems, wherein the patient-specific preview is presented within a single view on the user interface.

2. The media of claim 1, wherein the cost includes relative cost, actual wholesale price, institution cost, patient cost, or cost effectiveness.

3. The media of claim 1, wherein the availability includes a numerical amount or relative amount of a drug in stock.

4. The media of claim 1, wherein the susceptibility information incorporates cross-venue antibiogram data obtained from one of: the patient, an institution, a practice associated with a clinician, a zip code, a county, a city, a state, a region, or a country.

5. The media of claim 1, where receiving the selection of the specific disease state for the patient further comprises receiving a clinician-input selection on the specific disease state from the clinician device.

6. The media of claim 1, wherein receiving the selection of the specific disease state for the patient further comprises automatically receiving the selection of the specific disease state via an EMR of the patient.

7. The media of claim 1, further comprising using the specific disease state to identify those of the plurality of patients that share the specific disease state of the patient.

8. The media of claim 7, further comprising using the specific disease state to identify the susceptibility of pathogens represented in the cross-venue antibiogram that correspond to those of the plurality of patients that share the specific disease state of the patient.

9. The media of claim 8, wherein the patient-specific preview of the patient-specific antibiogram presented on the user interface of the clinician device displays time-sensitive patient-specific information.

10. The media of claim 1, wherein the patient-specific antibiogram is further created from the patient information of those of the plurality of patients that have the same or similar genomic information as the patient.

11. The media of claim 1, wherein the susceptibility information is based on the patient-specific antibiogram and includes information relevant to one or more of the patient, an institution, a practice associated with a clinician, a zip code, a county, a city, a state, a region, or a country.

12. A computer-implemented method comprising:

generating a cross-venue antibiogram that represents susceptibility of pathogens for a plurality of patients having different medical conditions, wherein the cross-venue antibiogram is generated from patient information for the plurality of patients obtained from acute and non-acute data sources that are associated with two or more independent electronic medical record (EMR) systems, wherein the acute and non-acute data sources are disparate data sources using distinct nomenclatures;

providing the disparate acute and non-acute data sources with real-time access to the cross-venue antibiogram by storing the cross-venue antibiogram on one or more cloud servers accessible by computing devices of the disparate acute and non-acute data sources, wherein the computing devices associated with the disparate acute and non-acute data sources are remote from the one or more cloud servers;

updating the cross-venue antibiogram in real time with additional patient information received from the disparate acute and non-acute data sources using the distinct nomenclatures;

receiving a selection of a specific disease state for a patient;

receiving patient-specific information for the patient including at least one of medical conditions, laboratory results, or allergy information;

creating a patient-specific antibiogram from the updated cross-venue antibiogram, wherein the patient-specific antibiogram is created using the susceptibility of pathogens represented in the updated cross-venue antibiogram for those of the plurality of patients that share the specific disease state with the patient;

providing a first medication option for the patient based on the patient-specific antibiogram, the first medication option including at least one of dosing, generic alternatives, cost, availability, or susceptibility information, wherein the first medication option is provided to a first pharmacy;

based on the patient-specific antibiogram, determining that the first medication option is ineffective; and based on the first medication option being ineffective, providing a second medication option to a second pharmacy in real-time.

13. The method of claim 12, further comprising receiving a medical order for the patient.

14. The method of claim 13, further comprising determining whether the medical order specifies at least one of the multiple medication options provided.

15. The method of claim 14, further comprising when it is determined that the medical order does not specify at least one of the multiple medication options, providing an alert for intervention to a clinician.

16. The method of claim 12, wherein the patient-specific antibiogram is further created from the patient information of those of the plurality of patients that share allergy information with the patient.

17. The method of claim 12, wherein the patient-specific antibiogram is further created from the patient information of those of the plurality of patients that share one or more of the medical conditions of the patient.

18. The method of claim 12, wherein the patient-specific antibiogram is further created from the patient information of those of the plurality of patients having similar genomic information as the patient.

19. The method of claim 12, further comprising providing the patient-specific antibiogram to a clinician.

20. A computerized system comprising:

one or more processors; and one or more computer storage media storing computer-useable instructions that, when used by the one or more processors, cause the one or more processors to:

generate a cross-venue antibiogram that represents susceptibility of pathogens for a plurality of patients having different medical conditions, wherein the cross-venue antibiogram is generated from patient information for the plurality of patients obtained from acute and non-acute data sources that are associated with two or more independent electronic medical record (EMR) systems, wherein the acute and non-acute data sources are disparate data sources using distinct nomenclatures;

provide the disparate acute and non-acute data sources with real-time access to the cross-venue antibiogram by storing the cross-venue antibiogram on one or more cloud servers accessible by computing devices of the disparate acute and non-acute data sources, wherein the computing devices associated with the disparate acute and non-acute data sources are remote from the one or more cloud servers;

update the cross-venue antibiogram in real time with additional patient information received from the disparate acute and non-acute data sources using the distinct nomenclatures;

receive a selection of a specific disease state for a patient;

receive patient-specific information for the patient including at least one of medical conditions, laboratory results, or allergy information;

create a patient-specific antibiogram from the updated cross-venue antibiogram, wherein the patient-specific antibiogram is created using the susceptibility of pathogens represented in the updated cross-venue antibiogram for those of the plurality of patients that share the specific disease state with the patient;

determining the patient has been prescribed an inappropriate medication option for the patient based on the patient-specific antibiogram; and alerting a medication steward of the inappropriate medication option for the patient, wherein the alert is documented to determine inappropriate medication option trends within the plurality of patients.

* * * * *

UNITED STATES PATENT AND TRADEMARK OFFICE

CERTIFICATE OF CORRECTION

PATENT NO. : 10,922,774 B2
APPLICATION NO. : 14/586344
DATED : February 16, 2021
INVENTOR(S) : Hugh H. Ryan et al.

It is certified that error appears in the above-identified patent and that said Letters Patent is hereby corrected as shown below:

In the Claims

Column 52, Line 54: Please remove “where” and replace with --wherein--.

Column 52, Line 56: Please remove “on” and replace with --of--.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*